(12) United States Patent
Barenholz et al.

(10) Patent No.: US 10,722,599 B2
(45) Date of Patent: Jul. 28, 2020

(54) LIPID ASSEMBLIES AND USES THEREOF AND SOME PH AND ELECTROSTATIC MODULATING LIPIDS TO BE USED IN SAID ASSEMBLIES

(71) Applicant: Yissum Research Development Company of the Hebrew University of Jerusalem Ltd., Jerusalem (IL)

(72) Inventors: Yechezkel Barenholz, Jerusalem (IL); Rivka Cohen, Jerusalem (IL); Kirill Makedonski, Jerusalem (IL); Eylon Yavin, Jerusalem (IL); Andreas Ingemann Jensen, Frederiksberg (DK); Keren Turjeman, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/548,601

(22) PCT Filed: Feb. 4, 2016

(86) PCT No.: PCT/IL2016/050128
§ 371 (c)(1),
(2) Date: Aug. 3, 2017

(87) PCT Pub. No.: WO2016/125163
PCT Pub. Date: Aug. 11, 2016

(65) Prior Publication Data
US 2018/0043036 A1 Feb. 15, 2018

Related U.S. Application Data

(60) Provisional application No. 62/111,847, filed on Feb. 4, 2015, provisional application No. 62/111,861, filed on Feb. 4, 2015.

(51) Int. Cl.
| | | |
|---|---|---|
| *A61K 48/00* | (2006.01) |
| *A61K 9/127* | (2006.01) |
| *C07K 5/093* | (2006.01) |
| *C07C 271/22* | (2006.01) |
| *C07C 237/22* | (2006.01) |
| *C07D 233/60* | (2006.01) |
| *C07K 5/113* | (2006.01) |
| *C07C 69/40* | (2006.01) |
| *C07K 5/072* | (2006.01) |
| *A61K 47/24* | (2006.01) |
| *A61K 47/44* | (2017.01) |

(52) U.S. Cl.
CPC ........ *A61K 48/0033* (2013.01); *A61K 9/1272* (2013.01); *A61K 9/1277* (2013.01); *A61K 47/24* (2013.01); *A61K 47/44* (2013.01); *C07C 69/40* (2013.01); *C07C 237/22* (2013.01); *C07C 271/22* (2013.01); *C07D 233/60* (2013.01); *C07K 5/06104* (2013.01); *C07K 5/06113* (2013.01); *C07K 5/0819* (2013.01); *C07K 5/1021* (2013.01)

(58) Field of Classification Search
None
See application file for complete search history.

(56) References Cited

U.S. PATENT DOCUMENTS

| | | | | |
|---|---|---|---|---|
| 2005/0164963 A1* | 7/2005 | Essler | ............... | A61K 9/1271 514/44 A |
| 2008/0311181 A1* | 12/2008 | Endert | ............... | A61K 9/127 424/450 |
| 2009/0220584 A1* | 9/2009 | Goodwin | ............... | A61K 9/127 424/450 |
| 2013/0323298 A1 | 12/2013 | Goodwin et al. | | |

FOREIGN PATENT DOCUMENTS

| | | | | | |
|---|---|---|---|---|---|
| CN | 102391498 A | * | 3/2012 | ............ | C08G 65/48 |
| WO | 02/066012 A2 | | 8/2002 | | |
| WO | 2004/110499 A1 | | 12/2004 | | |
| WO | 2005/094783 A2 | | 10/2005 | | |

(Continued)

OTHER PUBLICATIONS

CAS SciFinder English language abstract of CN 102391498 A (Mar. 28, 2012).*

(Continued)

*Primary Examiner* — Brian J Davis
(74) *Attorney, Agent, or Firm* — Vorys, Sater, Seymour and Pease LLP

(57) ABSTRACT

Provided are modified lipid compounds and their use in the formation of lipid assemblies. Also provided are lipid assemblies including (a) an amphoteric lipid including in covalent association with (i) one or more acyl chains; (ii) one or more weak base moiety; (iii) one or more weak acid moiety; the lipid assembly also including (b) one or more additional lipids, at least one of which being a zwitterionic lipid. In some embodiments, the amphoteric lipid is a compound including (a) a tri-functional moiety; (b) two non-phosphate lipid chains associated with two of the functional moieties of said tri-functional moiety; (c) optionally a spacer moiety associated with the third of the functional moieties of said tri-functional moiety; and (d) a polyalkylamine optionally including a short peptide with one to several carboxylic acid residues. Further provided are the uses of the lipid assembly, inter alia, for transfection or cancer treatment.

10 Claims, 10 Drawing Sheets
Specification includes a Sequence Listing.

(56) References Cited

FOREIGN PATENT DOCUMENTS

| WO | 2007/064857 A2 | 6/2007 |
| WO | 2008/043575 A2 | 4/2008 |
| WO | 2009/047006 A2 | 4/2009 |
| WO | 2010/150004 A1 | 12/2010 |
| WO | 2011/003834 A1 | 1/2011 |

OTHER PUBLICATIONS

Adami et al., "An Amino Acid-based Amphoteric Liposomal Delivery System for Systemic Administration of siRNA", Molecular Therapy, vol. 19, No. 6, pp. 1141-1151, (2011).

Fridkin et al., "Systematic solid-phase synthesis of linear pseudooligolysines containing multiple adjacent Ch2NH amide bond surrogates: potential agents for gene delivery", J. Peptide Res., vol. 58, pp. 36-44, (2001).

Perttu et al., "Inverse-Phosphocholine Lipids: A Remix of a Common Phospholipid", J. Am. Chem. Soc., vol. 134, pp. 4485-4488, (2012).

Venditto et al., "Sulfated quaternary amine lipids: a new class of inverse charge zwitterlipids", Chem. Commun., vol. 50, pp. 9109-9111, (2014).

Walsh et al., "Synthesis and characterization of novel zwitterionic lipids with pH-responsive biophysical properties", Chem. Commun., vol. 48, 5575-5577, (2012).

\* cited by examiner

LIPID ASSEMBLIES AND USES THEREOF AND SOME PH AND ELECTROSTATIC MODULATING LIPIDS TO BE USED IN SAID ASSEMBLIES

SEQUENCE LISTING

The Sequence Listing submitted in text format (.txt) filed on Aug. 3, 2017, named "SequenceListing.txt", created on Aug. 3, 2017, 4.79 KB), is incorporated herein by reference.

TECHNOLOGICAL FIELD

The present disclosure generally provides modified lipids and uses thereof, e.g. in lipid-based delivery systems.

BACKGROUND ART

Fridkin, M. et al. J Pept Res. 58:36-44, 2001
Walsh, C. L. et al. Chem Commun. 48:5575-5577 2012;
Venditto, V. J. et al. Chem Commun. 50:9109-9111, 2013;
Perttu, E. K. et al. J Am Chem Soc. 134:4485-4488, 2012
International Patent Application Publication No. WO 02/066012;
International Patent Application Publication No. WO 04/110499;
International Patent Application Publication No. WO 05/094783;
International Patent Application Publication No. WO 07/064857;
International Patent Application Publication No. WO 08/043575;
International Patent Application Publication No. WO10/150004;
International Patent Application Publication No. WO 11/003834;
Adami R C et al. *An Amino Acid-based Amphoteric Liposomal Delivery System for Systemic Administrion of siRNA* Molecular Therapy 9(6):1141-1151 2011;

Acknowledgement of the above references herein is not to be inferred as meaning that these are in any way relevant to the patentability of the presently disclosed subject matter.

BACKGROUND

The use of nanoparticulate formulations based on lipids and polymers for drug delivery has been and is still heavily pursued as such systems have been shown to improve the bio-availability, the pharmacokinetics, and the tolerability profile of a broad spectrum of drugs from small hydrophobic ones (e.g. Amphotericin B) to macromolecules, such as peptides, proteins, and nucleic acids (i.e. DNA plasmids, siRNA, etc). In many situations, in order to be functional and non-toxic, the delivery system has to demonstrate the ability to change its surface pH and electrostatics; for example, to be passively charged for efficient loading of nucleic acids, but neutral when present in the blood. This need can be met by including amphoteric lipids which include weak acidic and weak basic moieties.

In this regard, amphoteric liposomes are typically composed of a mixture of positive and negative lipid-based materials that may or may not include neutral lipids and other amphiphiles/helper lipids/surfactants. Alternatively, such amphoteric liposomes are defined as those that change their overall charge as a function of pH and are almost charge-less at neutral pH. Such lipid-based materials may be highly advantageous in several aspects: (1) The overall charge of the liposome may be tuned according to the ratio between negative to positive lipids and/or moieties. The ability to modify and modulate surface pH and surface electrostatics may, in turn, improve the encapsulation efficiency of the agent/drug according to its physico-chemical characteristics such as size, charge and hydrophobicity; (2) Modulating the overall properties of the liposome's surface by controlling parameters such as charge distribution and hydrophilicity allows designing liposomes with improved pharmacokinetics profile and extended circulation in-vivo.

To date, most amphoteric liposomes reported were prepared by combining mixtures of cationic, anionic and neutral lipids or anionic peptides with lipids such as DOTAP. A different approach is based on using pH responsive lipids that are protonated at a lower pH (below pKa) and unprotonated at pHs above the pKa.

A different approach relies on the use of peptide-lipid hybrids as means of modifying the overall characteristics of the lipid-based delivery system. For example, amino acid-modified lipids were shown to improve transfection of nucleic acids into cells. Other approaches include the use of a receptor ligand that is conjugated to the lipid, lipid conjugation to positively charged peptides or adding anionic polymers to lipoplexes or polyplexes. Although these systems have shown promising data in terms of uptake efficiency in cells, their inherent positive charge may render them toxic both in-vitro and in-vivo. Such systems are mostly limited to encapsulate nucleic acids which are negatively charged molecules.

A report published in 2001 [Fridkin, M. et al. J Pept Res (2001), 58, 36-44] describes the synthesis of a reduced oligolysine on the solid support by the generation of a Schiff base followed by its reduction with $NaBH_3CN$.

Further, recent reports describe the synthesis of zwitterionic lipids that are pH-responsive [Walsh, C. L. et al. Chem Commun (2012), 48, 5575-5577; Venditto, V. J. et al. Chem Commun (2013), 50, 9109-9111; Perttu, E. K. et al. J Am Chem Soc (2012), 134, 4485-4488].

In addition, International Patent Application Publication No. WO 02/066012 describes amphoteric liposomes being stable at pH 4.2 and pH 7.5 and comprising at least one amphipathic cationic lipid, at least one amphipathic anionic lipid, and at least one neutral lipid. The amphoteric liposomes described in this publication also carry an active ingredient and are characterized by an isoelectric point of between 4 and 7.

International Patent Application Publication No. WO 04/110499 describes sphingolipids polyalkylamine conjugates for use in transfection.

International Patent Application Publication No. WO 05/094783 describes a serum-stable amphoteric liposomal formulation comprising a liposome with an aqueous interior and at least one active substance in the aqueous interior, wherein the liposomes comprise 10-60 mole % neutral lipids, 30-50 mole % cholesterol, and, as charged lipids, either 5-30 mole % amphoteric lipids or a maximum of 50 mole % of a mixture of cationic and anionic lipids, and wherein the active substance comprises at least one oligonucleotide.

International Patent Application Publication No. WO 07/064857 describes DNAi oligonucleotides sequestered by amphoteric liposomes for the treatment of cancer. The amphoteric liposomes are described as having an anionic or neutral charge at physiological pH and a cationic charge at an acidic pH of about 4.

International Patent Application Publication No. WO 08/043575 describes the use of amphoteric liposomes for targeting nucleic acids encoding CD40 to thereby modulate the expression of CD40.

International Patent Application Publication No. WO10/150004 describes oligomer analogues and their use in oligonucleotide-based therapies. More specifically, the invention concerns oligonucleotides carrying lipid molecules and their use as potential inhibitors of gene expression.

International Patent Application Publication No. WO 11/003834 describes lipid assemblies or liposomes that comprise both negatively charged lipids having a carboxylic or phosphate head group and positively charged lipids having imino or guanido moieties or derivatives thereof in the respective polar regions.

Adami R C et al. describes natural and modified dialkylated amino acid-based upon arginine for development of an efficient small interfering RNA (siRNA) delivery system [Molecular Therapy vol. 9(6) 1141-1151 2011].

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

GENERAL DESCRIPTION

Figure 1A:
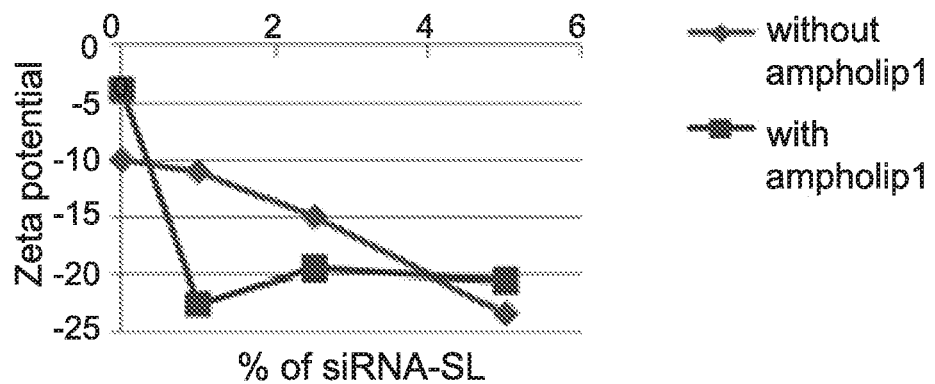
FIGS. 1A-1B are graphs showing the analysis of zeta potential in DOPC/10% Ampholip formulations loaded with different concentrations of PLK1 siRNA-SL (FIG. 1A) or RAC1 (FIG. 1B) siRNA-Chol. The diamonds/triangles line (FIG. 1A and FIG. 1B, respectively) and the squares or x line (FIG. 1A and FIG. 1B, respectively) show the formulations without and with 10% Ampholip1, respectively.

Liposomes specifically address challenges involved with the transit of drugs, such as oligonucleotides into cells, namely bio-distribution, cellular uptake and endosomal release. In addition, aggregate formation with serum components and relatively short circulation lifetimes represent major challenges of these carrier systems for systemic applications.

With the aim of providing a delivery system with an effective bio-distribution and cellular uptake, the inventors have developed several platforms for the synthesis of a variety of modified lipids that include various functional groups that are modulated by the surrounding pH. These modified lipids constituted a first broadest aspect of the present disclosure, herein after the "modified lipid aspect". According to this modified lipid aspect, lipids could be either modified with (1) acidic moieties (e.g. a short peptide that is rich in acidic groups such as carboxylic acids of Asp and Glu) or (2) a combination of both acidic and basic moieties for generating amphoteric lipids. The acidic or amphoteric lipids may then be finely tuned by changing the pH, thereby providing a simple approach to improve the encapsulation of a variety of molecules according to their overall interaction with such lipids as primarily dictated by the electrostatic interactions, which are modulated by pH. In addition, as such lipids are not highly positively charged (and in most cases neutral or slightly positively/negatively charged), such liposomes are expected to be less toxic.

Within this aspect, the inventors have developed several synthetic approaches aimed for the development of novel lipids that are responsive to changes in the external pH of the medium. Such modified lipids are suitable for insertion into nanoparticulate drug delivery systems (DDSs) such as liposomes, micelles, emulsions, cubic phases and others, either during or after self-assembly. These DDSs encapsulate a variety of molecules which association with the nanoparticles may or may not be based on the interactions of these molecules with the modified lipid. When the loading is based on the interaction with the modified lipids, the extent of the interaction is determined at least in part by the surface pH and electrostatics which may be fine-tuned by altering the pH of the medium.

The novel lipids of the invention may be generally described as combining two main structural features with at least one other feature, as disclosed herein.

The several synthetic approaches are described herein below under Schemes 1 to 6, each constituting separate embodiments of the present disclosure.

In accordance with another of its broadest aspect, herein the "lipid-based delivery system aspect", the present disclosure provides, lipid-based systems that can associate with active principles and suitably deliver these active principles into the target site. In this regard, it is noted that most amphoteric lipid-based delivery systems reported hitherto, such as liposomes, were prepared by combining mixtures of cationic, anionic and neutral lipids or anionic peptides with lipids such as DOTAP (1,2-dioleoyl-3-trimethylammonium-propane). A different approach forming the basis of the present invention is based on using pH-responsive lipids that are protonated at a lower pH.

Turning now to the modified lipid aspect, the present disclosure provides a compound comprising: (1) a tri-functional moiety, such as glycerol; (2) two non-phosphate lipid chains, e.g., alkyl chains associated with two of the functional moieties of said tri-functional moiety; (3) optionally a spacer moiety associated with the third of the functional moieties of said tri-functional moiety; and (4) a polyalkylamine optionally comprising a short peptide that comprises one to several carboxylic acid residues.

In some embodiments, the present disclosure provides a compound of the general formula (I):

$$D\text{-}Sp\text{-}T\text{-}L_2 \qquad (I)$$

wherein

T is a moiety comprising three functional groups, each being independently suitable for conjugation or association or coupling with another of the chemical entities in the compound, e.g., each of the functional groups may be independently selected from amine, carboxyl or a carboxyl derivative (such as ester, thioester, amide, carbamate, etc), NHS esters or other activating groups, sulfhydryl, carbonyls, hydroxyl, azide (also via Azide alkyne Huisgen cycloaddition), —CN, —O—, —S—, —NH—, —C(=O)— and —S—S—;

$L_2$ represents two of the same or different non-phosphate lipid groups (each being referred to as "L"), each lipid group being associated to one of said three functional moieties in T;

Sp represents a spacer group or atom which may or may not be present; and

D is a polyalkylamine group comprising at least one negatively charged moiety and at least one positively charged moiety.

The trifunctional moiety designated "T" is a chemical moiety comprising three functional groups, each being selected as above. The three moieties may all be the same or all different or two of the three moieties may be the same and the other may be different. The three moieties are selected to provide connectivity to two non-phosphate lipid moieties (designated L) and optionally to a spacer moiety (Sp) or to a polyalkylamine (D) in case the spacer moiety is not present.

In some embodiments, the trifunctional moieties comprise three identical functional groups. In some embodiments, each of the functional groups is different. In further embodiments, two of the three functional groups are the same and the third is different.

In some embodiments, the trifunctional moiety is derived from a triamine or a triol. As may be understood, for example, where the functional groups are hydroxide groups (—OH), once associated with the lipid moieties or the spacer moiety or the polyalkylamine, such association being via the oxygen —O— atom.

In some embodiments, the trifunctional group is derived from a triol. In some embodiments, the trifunctional is derived from glycerol.

The non-phosphate lipid moiety designated "L" is a lipid moiety not comprising a phosphate moiety or any derivative of a phosphate moiety. The lipid moiety is an alkyl chain having between 5 and 24 carbon atoms ($C_5$-$C_{24}$), which may be associated with the trifunctional moiety T via a heteroatom of the T, e.g., such as an oxygen atom (to form acyl chain) or a nitrogen atom. In other embodiments, the lipid moiety is derived from a fatty acid having at least 6 carbon atoms. The fatty acid being generally of the structure $C_5$-$C_{24}C(O)$—, wherein the oxygen atom is associated, bonded or conjugated to the functional group of L. In some embodiments, the alkyl chain of the fatty acid may be linear or substituted, and may or may not comprise one or more double or triple bonds.

In some embodiments, one L is a $C_5$-$C_{24}$ alkyl, e.g., associated to an oxygen atom of the glycerol moiety and another of the L groups is a $C_5$-$C_{24}C(O)$— group.

In some embodiments, the lipid moiety is a fatty acid moiety, as defined, comprising between 6 and 25 carbon atoms. In some embodiments, the lipid moiety is a fatty acid moiety, as defined, comprising between i to ii, wherein i in any integer between 7 to 25 and ii is, independently from i, an integer from 7 to 25, and ii is always larger than i.

In some embodiments, where the trifunctional moiety is derived from glycerol, the fatty acid is a diglycerolipid of the structure -T-L$_2$, wherein T is a triol derived from glycerol and L$_2$ represents two same or different fatty acids, each connected to a different oxygen atom of the glycerol moiety (the third oxygen atom being associated with the spacer moiety or the polyalkylamine).

In some embodiments, the compound of the present disclosure is an amphoteric compound of the structure (IIa) or (IIb):

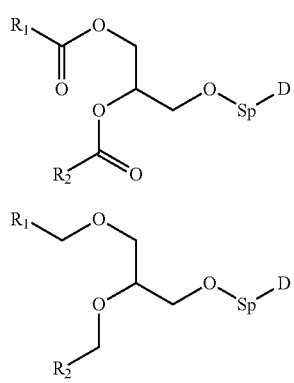

(IIa)

(IIb)

wherein in each of structure (IIa) and (IIb), independently of the other:

each of R$_1$ and R$_2$, independently of the other, represents a carbon chain, specifically, a C$_5$-C$_{24}$ carbon chain and wherein Sp and D are each as defined.

In this connection, it is to be understood that the above (IIa) or (IIb) also encompass the combination (IIc)

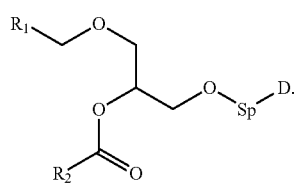

(IIc)

The spacer moiety designated "Sp" is a linker moiety connecting a functional group of the trifunctional moiety, e.g., oxygen of the glycerol moiety, and the polyalkylamine group D.

These compounds of formula IIa, IIb or IIc are referred to herein, at times, as glycerolipids.

In some embodiments, the compound of the present disclosure is a glycerolipid of the structure (IIa).

The spacer moiety designated "Sp" is a linker moiety connecting a functional group of the trifunctional moiety, e.g., an oxygen of the glycerol moiety, and the polyalkylamine group D.

In some embodiments, the spacer moiety is a group selected to have between 3 and 10 carbon atoms. In some embodiments, the spacer moiety constitutes a single atom.

In some embodiments, the spacer moiety is derived from a difunctional group such as a diamine, a diol, a dithiol or a dicarboxylic acid or any derivative thereof.

The spacer moiety may be associated with a functional group of the trifunctional moiety, at one end, and with the polyalkylamine, at the other end, via a bond selected from an ester group, an amide group, a carbonate group, a thioester group, a maleimide group, a triazole group, a urea, a carbamate group, and others.

In some embodiments, where a spacer moiety is present, it may be selected from any carbonyl or carbonyl containing spacer, and from any of the following:

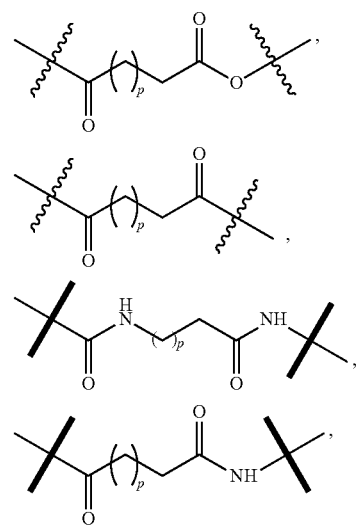

wherein p is an integer between 0 and 7.

In some embodiments, p is an integer between 1 and 5.

In some embodiments, the compound of the present disclosure is of the general structure III:

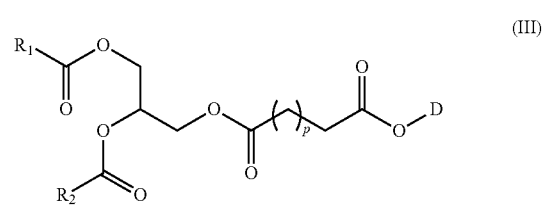

(III)

wherein R$_1$, R$_2$, p and D are as defined herein.

In some embodiments, the compound of the present disclosure is of the general structure IV:

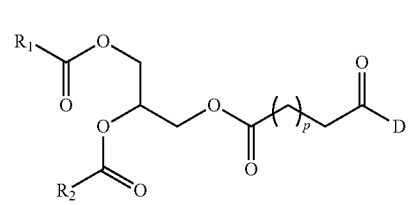

(IV)

wherein each of R$_1$, R$_2$, p and D are as defined herein.

In some embodiments, the compound of the present disclosure is of the general structure V:

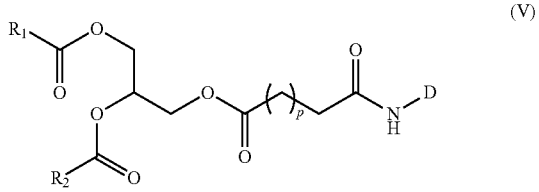

(V)

wherein each of $R_1$, $R_2$, p and D are as defined herein.

In some embodiments, the compound of the present disclosure is of the general structure VI:

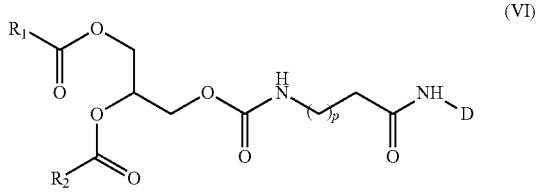

(VI)

wherein each of $R_1$, $R_2$, p and D are as defined herein.

In some embodiments, the spacer is absent and the polyalkylamine D is directly connected to the aforementioned functional group.

The polyalkylamine designated "D" is a carbon chain interrupted by a plurality of N atoms. The polyalkylamine comprises at least one negatively charged moiety, designated D(−), and at least one positively charged moiety, designated D(+).

As used herein, the negatively charged moiety (D(−)) is a carbon moiety comprising one or more functional groups capable of carrying a negative charge or being transformable into a moiety carrying a negative charge. Such group may be a carboxylate group and a carboxylic group. In some embodiments, the functional groups capable of carrying a negative charge may be pendant groups on the carbon chain.

In some embodiments, the carbon chain is a short peptide comprising between 2 and 6 amino acids, at least one of said amino acids bearing a group capable of carrying a negative charge, e.g., a carboxylic acid or a carboxylate.

In some embodiments, the negatively charged moiety (D(−)) comprises or consists between 2 and 6 amino acids, at least one of which being selected from aspartic acid and/or glutamic acid.

In some embodiments, the negatively charged moiety (D(−)) comprises a plurality of aspartic acid and/or glutamic acid. In some embodiments, one or more of the amino acids is histidine.

In some embodiments, the negatively charged moiety (D(−)) is directly associated, at one end, with the spacer moiety or with the trifunctional moiety, where the spacer moiety is absent, and at the other end with the positively charged moiety.

In some embodiments, the compound of the present disclosure is of the general structure VII:

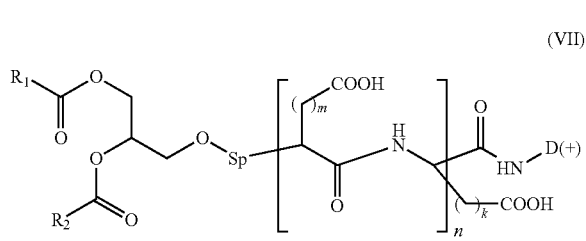

(VII)

wherein $R_1$, $R_2$, D(+) and Sp are each as defined herein, n is an integer defining the number of amino acids in the negatively charged moiety; said n being between 0 and 3 (where n equals 0, the negatively charged moiety comprises a single amino acid, being the end chain amino acid in the compound of formula VII); m is the number of carbon atoms in the acid side chain, and is selected from 1 and 2; and k is an integer equal to 1 or 2.

In some embodiments, a compound of formula VII is a compound of formula VIII:

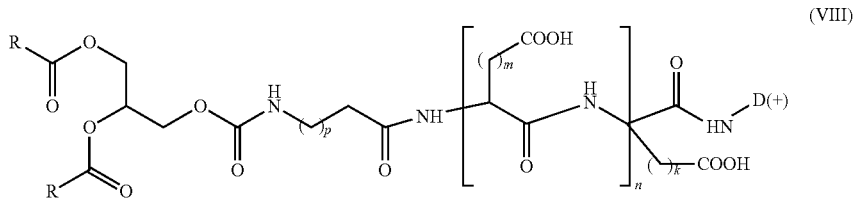

(VIII)

wherein each of $R_1$, $R_2$, D(+), p, m, n and k are as defined herein.

The positively charged moiety (D(+)) is a carbon moiety comprising one or more functional groups capable of carrying a positive charge. The functional group capable of carrying a positive charge is selected from ammonium, amine, secondary amine, a tertiary amine and others. In some embodiments, the positively charged moiety (D(+)) is an aliphatic chain interrupted by one or more nitrogen atoms.

In some embodiments, the moiety is selected from spermidine, spermine, norspermidine, bis-ethylspermine, thermospermine, and a polyamide derived from the reduction of a peptide.

Each of the aliphatic chains interrupted by one or more nitrogen atoms may be end-chain substituted by at least one capping group, at least one protection group, at least one labile (hydrolizable) group or by a hydrogen atom. In some embodiments, the end-chain substitution is by hydrogen, an alkyl, an ester, a ketone, a carboxylic acid, an aldehyde, an acyl, a carbamate and others.

In some embodiments, the positively charged moiety is selected from spermidine and spermine, which may or may not be end-chain substituted.

In some embodiments, the positively charged moiety is spermine.

In some embodiments, the compound of the present disclosure is of the general structure IX:

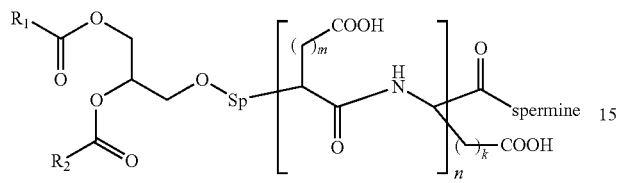

(IX)

wherein each of $R_1$, $R_2$, Sp, m, k, and n are as defined herein.

In some embodiments, in a compound of structure IX, Sp is selected from carbonyl-comprising groups or is any one of

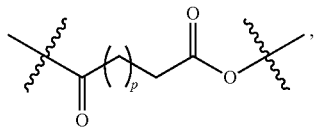

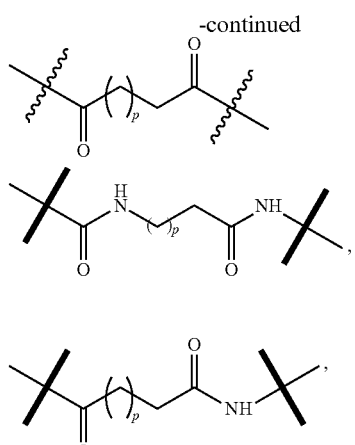

wherein each p is as defined herein.

In some embodiments, in a compound of structure IX, each of $R_1$ and $R_2$ are the same.

In some embodiments, the compound of any of structures I to IX is in a charged form. In some embodiments, the compounds of the present disclosure comprise one or more counter-ion (cation or anion). In some embodiments, the counter-ion is organic.

In some specific embodiments, the present disclosure provides a compound of the formula (X):

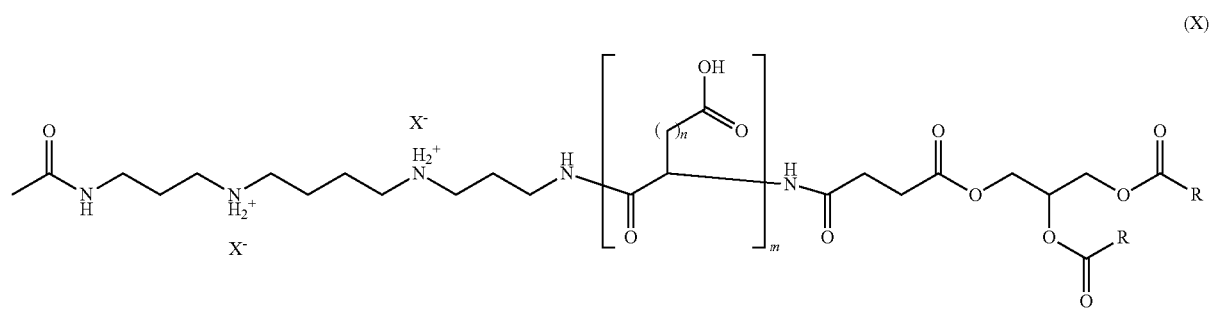

(X)

wherein n is 1 or 2 and m is between 1 and 4, and wherein the counter ion X– is selected from halides (Br⁻, I⁻, Cl⁻) and $CF_3COO^-$.

This compound is an amphoteric compound suitable for the construction of lipid assemblies for API delivery, as further described below.

In some embodiments, the present disclosure provides a negatively charged compound of any one of formulae (I) through (X).

In some further embodiments, the present disclosure provides a positively charged compound of any one of formulae (I) through (X).

The present disclosure provides a charged compound of any one of formulae (I) through (X), wherein at least one of the atoms is negatively charged and at least one other atom is positively charged.

The present disclosure further provides di-glutamate-di-stearoyl glycerol carbamoil spermine, or a salt thereof, a compound having the structure:

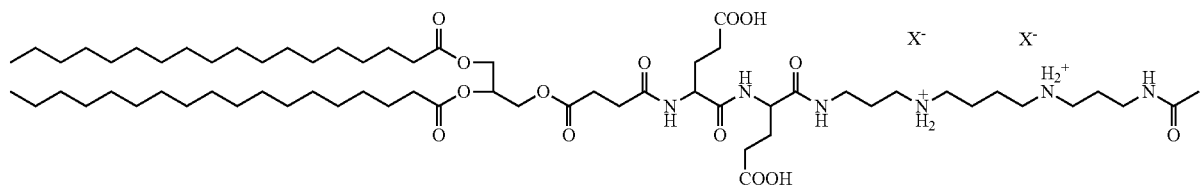
X: CF$_3$COO$^-$, CH$_3$COO$^-$ or Cl$^-$
The present disclosure further provides any compound selected from the following, each constituting a separate embodiment of the present disclosure:
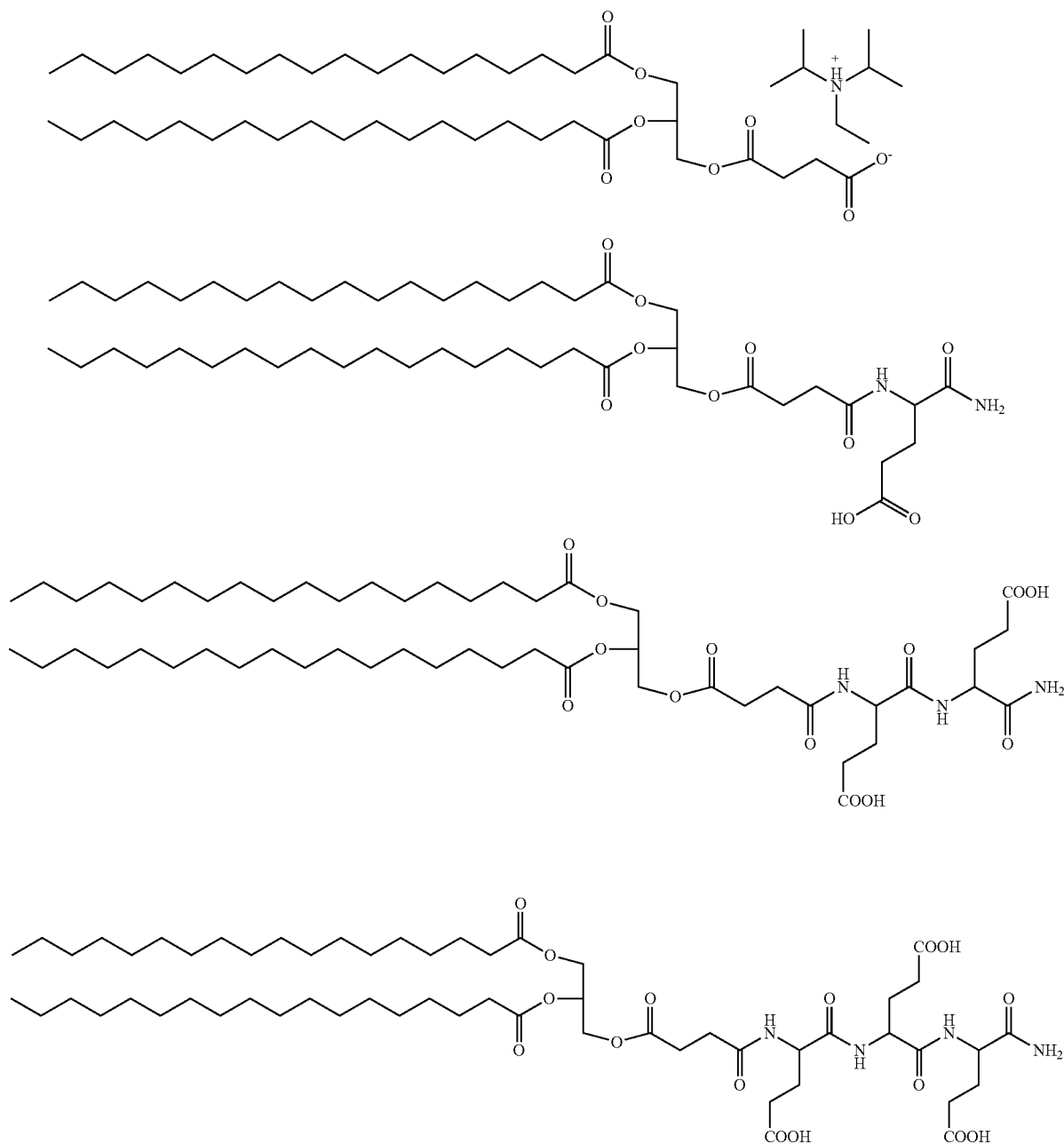

-continued

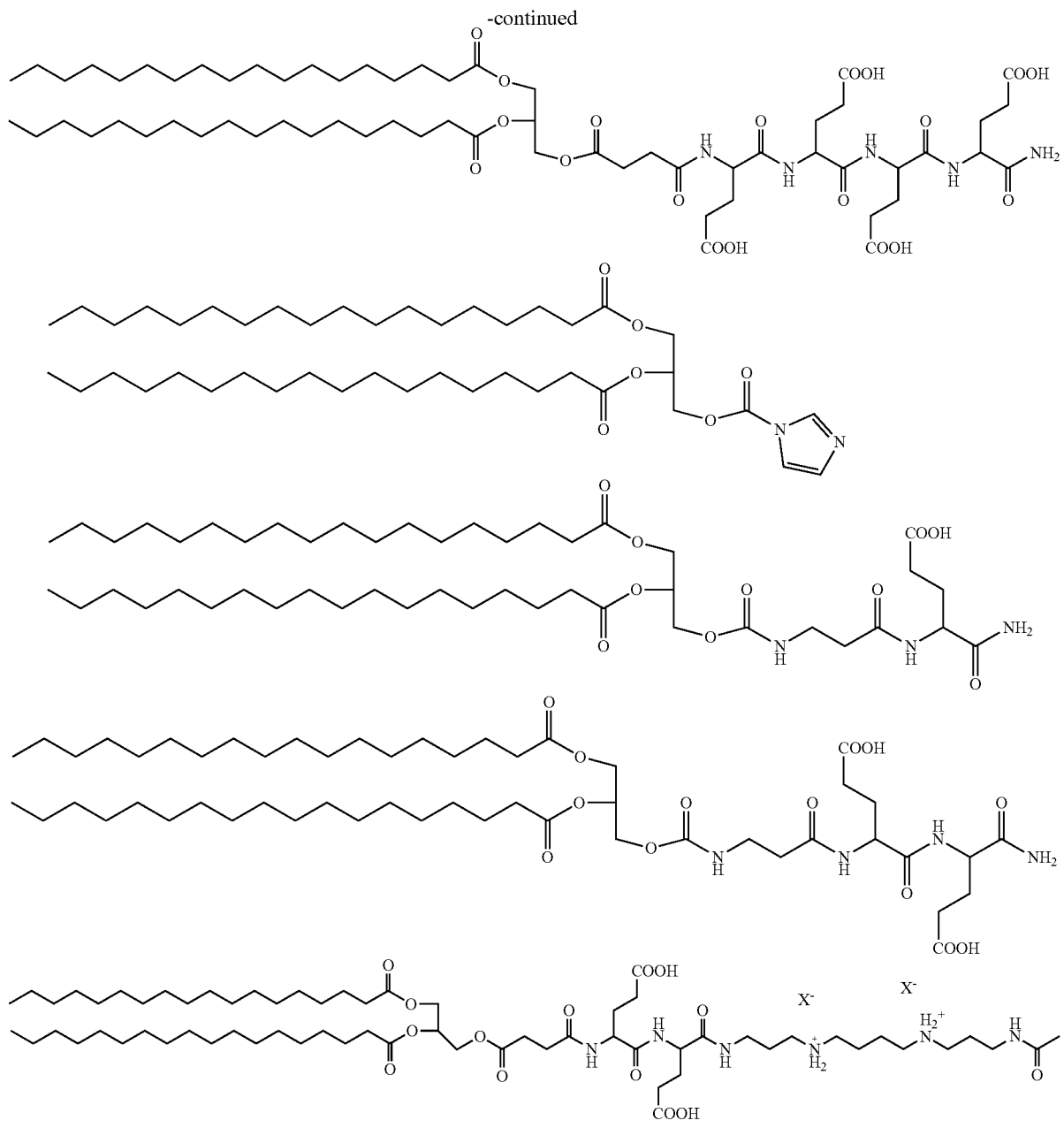

X: CF₃COO⁻, CH₃COO⁻ or Cl⁻

The compounds disclosed herein, as well as other types of amphoteric lipids, can be used for the construction of lipid based vehicles (lipid assemblies) for the delivery of, for example, active principle ingredients (APIs). This concern the lipid-based delivery system aspect disclosed herein. Specifically, in accordance with the lipid-based delivery system aspect, the present disclosure provides a lipid assembly comprising:
- an amphoteric lipid comprising, in covalent association:
  i) one or more acyl chains;
  ii) one or more weak base moiety; and
  iii) one or more weak acid moiety; and
- one or more additional lipids, at least one of which being a zwitterionic lipid.

The amphoteric lipid can be, yet without being limited thereto, a modified lipid of the modified lipid aspect disclosed herein. Yet, the lipid assembly can make use of other amphoteric lipids as disclosed herein.

In accordance with the lipid-based delivery system aspect, it has been surprisingly found that the use of a mixture of at least one amphoteric lipid with at least one zwitterionic lipid avoids or significantly reduces the undesired aggregation that is typically observed with cationic lipid-based vesicles or amphoteric vesicles (vesicles such as liposomes), comprising, as two separate entities, a positively charged lipid and a negatively charged lipid.

In the context of the present disclosure the term "lipid assembly" is to be understood as encompassing any organized collection of lipids formed when brought into contact with water. The term "lipid assembly" should be read interchangeably with its plurality form, namely, "lipid assemblies" and is to be understood as meaning a plurality of discrete ordered collection of lipids.

In some embodiments, the lipid assembly denotes micelles. In some other embodiments, the lipid assembly denotes liposomes. In yet some embodiments, the lipid assembly denotes cubic phases.

In yet some other embodiments, the lipid assemblies may be of any other form that can be used as drug delivery systems (DDS).

In the context of the present disclosure the term "amphoteric lipid" denotes a lipid that is responsive to changes in the external pH of the medium it which it resides. Such lipids were found to be suitable for insertion into lipid assemblies in drug delivery systems (DDSs) such as liposomes and micelles, either during or after self-assembly. The DDSs including the amphoteric lipid(s) may associate with the material to be delivered thereby based, inter alia, on electrostatic interactions. When the loading is based on the interaction with the lipids, the extent of the interaction is determined at least in part by the surface pH and electrostatics of the lipid assembly which may be fine-tuned by altering the pH of the medium.

In accordance with the present disclosure the amphoteric lipid carries on the same molecule at least the three recited components, namely, an acyl component, a weak base component and a weak acid component. The components are chemically associated by covalent bonds.

The acyl component, in accordance with some embodiments, comprises one or more acyl chains.

In some embodiments, the acyl chain has the general formula of —C(O)R, wherein R is a linear or branched alkyl, linear or branched alkenyl or linear or branched alkynyl groups. In some embodiments, the R within the acyl chain represents a $C_8$-$C_{24}$ chain. In some other embodiments, the acyl chain is a $C_{10}$-$C_{24}$ chain. In some other embodiments, the chain is a $C_{14}$-$C_{24}$ chain. In some embodiments, the chain is a $C_{12}$-$C_{18}$ chain. In some embodiments, the acyl chain has 8, 9, 10, 11, 12, 13, 14, 15, 16, 17, 18, 19, 20, 21, 22, 23 or 24 carbon atoms.

When the amphoteric lipid comprises more than one acyl chains, the R within the acyl chains may have the same or different lengths, saturation or branching. In some embodiments, the acyl chain is fully saturated. In some other embodiments, the acyl chain has at least one unsaturated carbon bond. Non-limiting acyl chains include any member of the group consisting of lauroyl (12:0), myristoyl (14:0), palmitoyl (16:0), heptadecanoyl (17:0), stearoyl (18:0), oleoyl (18:1), nonadecanoyl (19:0), arachidoyl (20:0), henarachidoyl (21:0), behenoyl (22:0), tricosanoyl (23:0), lignoceroyl (24:0), and any combinations of same (e.g. when more than one acyl is present)

The amphoteric lipid also comprises a weak base moiety. In the context of the present disclosure a "weak base" is intended to denote a chemical moiety that has a pKa below 11.0, and in accordance with some embodiments, pKa between about 11.0 and about 6.0, at times, between about 11.0 to 7.5.

In accordance with some embodiments, the weak base comprises at least one polyalkylamine chain (linear or branched) which may or may not be end-chain substituted. A polyalkylamine chain may generally be defined as a molecule comprising two or more repeating alkylamine units which may be the same or different within the chain. In some embodiments, the polyalkylamine contains n amine moieties, n being an integer of 1, 2, 3, 4, 5, 6, 7, 8, 9, or even 10. In some embodiments, n is no more than 6. In some embodiments, the polyalkylamine comprises between 3 to 6, at times between 3 to 4 amine moieties.

As to the alkyl moiety within the polyalkylamine, and in accordance with some embodiments, it may be the same or different in the repeating units. In other words, a polyalkylamine may include in the same chain different lengths of the alkyl section between the amine groups, including any one of and independently a $C_1$, $C_2$, $C_3$, $C_4$, $C_5$ alkyl between each amine moiety (i.e. $C_1$-$C_5$ alkyl). In some embodiments, the polyalkylamine comprises $C_3$ and/or $C_4$ alkyl sections.

In some embodiments, the polyalkylamine comprise a spermine. In some other embodiments, the polyalkamine is spermidine.

In some embodiments, the polyalkylamine is end chain substituted. The substitution may be selected from the group consisting of —COOH, —C(O)R'COOH, wherein R' may be $C_1$-$C_4$ alkyl The amphoteric lipid also comprises a weak acid moiety. In the context of the present disclosure a "weak acid" is intended to denote a chemical moiety that has a pKa above 3.0, at times above 3.5, further at times, in the range between about 3.5 and about 7.0.

The weak acid moiety may comprise any chemical entity that includes one or more carboxylic acid groups, such as —COOH, —C(O)R'COOH, wherein R' may be $C_1$-$C_4$ alkyl.

In some embodiments, the weak acid is located at a terminal end of the amphoteric lipid, e.g. to constitute the polyalkylamine end substitution, and in some other embodiments, it is a group internal within the amphoteric lipid, e g linking or forming part of the linkage to the polyalkylamine group and/or to the acyl chain.

In some embodiments, the weak acid comprises or is a —COOH; or is defined by —C(O)R'COOH, wherein R' may be $C_1$-$C_4$ alkyl.

In some embodiments, the weak acid is —C(O)—$C_1$-$C_4$alkyl-COOH, such as any one of —C(O)CH$_2$COOH or —C(O)CH$_2$CH$_2$COOH and preferably —C(O)CH$_2$CH$_2$COOH, at the end terminal of the polyalkylamine, i.e. -polyalkylamine-C(O)CH$_2$CH$_2$COOH.

In some embodiments, the weak acid comprises one or more amino acids comprising an acidic side chain. In some embodiments, the amino acid is glutamic acid. In some other embodiments, the amino acid is aspartic acid. In yet some other embodiments, the amino acid is histidine. In some embodiments, the weak acid comprises a plurality of any combination of aspartic acid and/or glutamic acid and/or histidine.

The amino acid may also be non-natural as long as it is decorated with a —COOH group (e.g. Cα(CH3) CH$_2$CH$_2$COOH, CH$_2$C(O)COOH). When more than one amino acid is included, it may be the same or different, and may be located adjacent or in remote locations within the amphoteric lipid. In some embodiments, the weak acid comprises a di or tri or tertiary amino acid moiety. In some embodiments, the weak acid comprises a di-glutamic acid.

The acyl chain, weak acid and weak base are chemically associated to form a molecule. The chemical association is preferably by covalent bonds.

In some embodiments, the chemical association is via spacers allowing the binding of the different components (i.e. the acyl, weak acid and weak base) into a single molecule. In this respect, and in accordance with some embodiments, the weak base and in particular, the polyalkylamine is linked via a carbamoyl group.

In some embodiments, some or all of the components are associated either directly or via a linker (such as with the carbamoyl polyalkylamine moiety) to a backbone compatible with lipids. In accordance with some embodiments, the backbone comprises a lipid, a lipid component or a lipid containing compound. In some embodiments, the backbone comprises a triamine or a triol (such as glycerol). In some other embodiments, the backbone comprises a sphingolipid.

In some embodiments the amphoteric lipid in the context of the present invention may be a compound comprising: (1) a tri-functional moiety such as a glycerol; (2) two non-phosphate lipid chains associated with two of the functional moieties of said tri-functional moiety; (3) optionally a spacer moiety associated with the third of the functional moieties of said tri-functional moiety; and (4) a polyalkylamine optionally comprising a short peptide that comprises one to several carboxylic acid residues.

A specific and preferred amphoteric lipid comprising trifunctional backbone, such as glycerol as the backbone is 1,2-di-glutamate-di-steroyl glycerol carbamoyl spermine, referred to herein by the name "Ampholip 1".

In some other embodiments, the backbone is sphingoid based, and specifically, a sphingolipid.

In accordance with some embodiments, the sphingolipid is ceramide (N-acyl sphingosine).

In accordance with some embodiments, the sphingolipid is dihydroceramides;

In accordance with some embodiments, the sphingolipid is phytoceramide;

In accordance with some embodiments, the sphingolipid is dihydrophytoceramide;

In accordance with some embodiments, the sphingolipid is ceramine (N-alkylsphinogsines);

In accordance with some embodiments, the sphingolipid is dihydroceramine,

In accordance with some embodiments, the sphingolipid is phytoceramine;

In accordance with some embodiments, the sphingolipid is dihydrophytoceramine.

In one embodiment, the sphingolipid is ceramide. In accordance with this embodiment, the amphoteric lipid may be generally defined by the formula X:

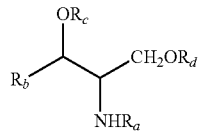

wherein $R_a$ represents an acyl moiety;

$R_b$ represents a branched or linear $C_{10}$-$C_{24}$ alkyl, alkenyl or polyenyl group;

$R_c$ and $R_d$ which may be the same or different represent a hydrogen or the group —C(O)-(weak base)-(weak acid) provided that at least one of $R_3$ and $R_4$ is —C(O)-(weak base)-(weak acid);

In some more specific embodiments, $R_b$ is an alkenyl; $R_c$ is hydrogen and $R_d$ is —C(O)-(weak base)-(weak acid).

In some yet further specific embodiments, $R_b$ is palmitoyl, the weak base is a polyalkylamine and the weak acid is a carboxy containing group.

A specific and preferred amphoteric lipid comprising sphingolipid as the backbone is carboxy-N-palmitoyl-D-erythro-sphigosyl-1-carbamoyl spermine, referred to herein by the name "COOH—CCS" or "Ampholip 2".

The synthesis of CCS may be found, inter alia, in International Patent Application Publication No. WO 2004/110980 (corresponding to U.S. Pat. No. 7,771,711), the content of which is incorporated herein in its entirety, by reference. In some embodiments, the amphoteric lipid is a compound of the general formulae selected from (I) to (IX) as described herein above. These specific structures represent, each, independently, alternative embodiments of the amphoteric lipid within the lipid assembly in the context of the lipid-based delivery system aspect of the present disclosure as also exemplified below.

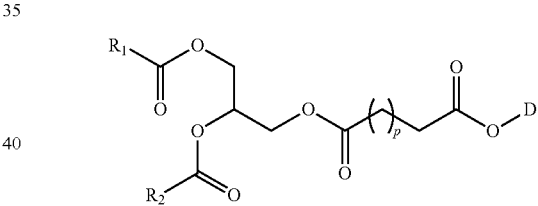

In a specific embodiment, the amphoteric lipid is of the formula (X):

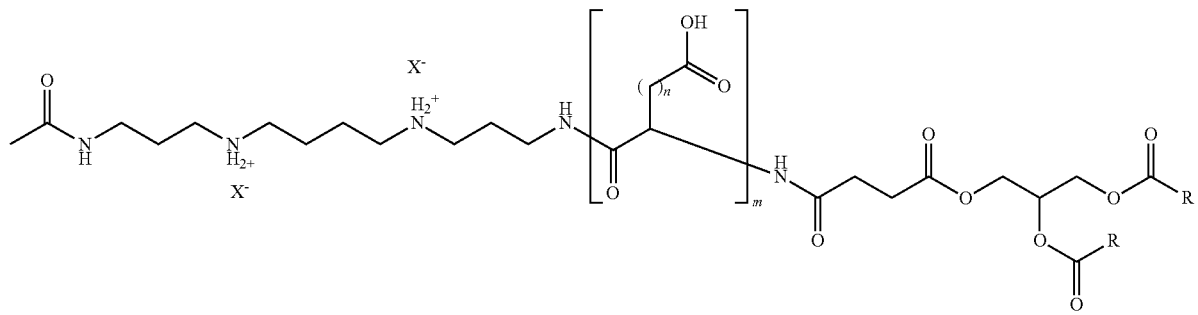

wherein n is 1 or 2 and m is between 1 and 4, and wherein the counter ion X– is selected from halides (Br⁻, I⁻, Cl⁻) and $CF_3COO^-$ as described hereinabove.

In one further specific embodiment, the amphoteric lipid is of the structure:
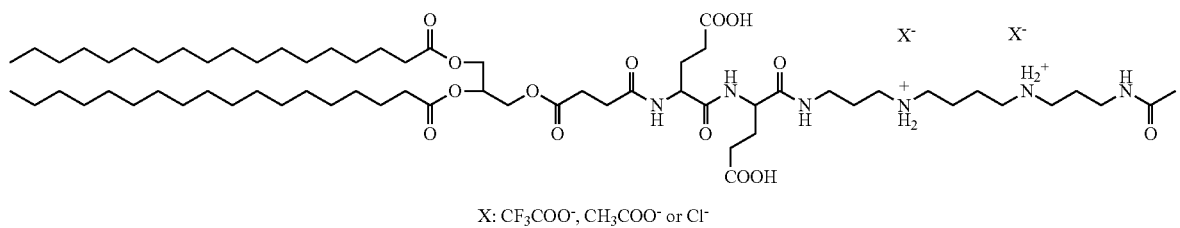
X: CF$_3$COO$^-$, CH$_3$COO$^-$ or Cl$^-$
The amphoteric lipid may also be any one of the following compounds, each representing a separate embodiment,
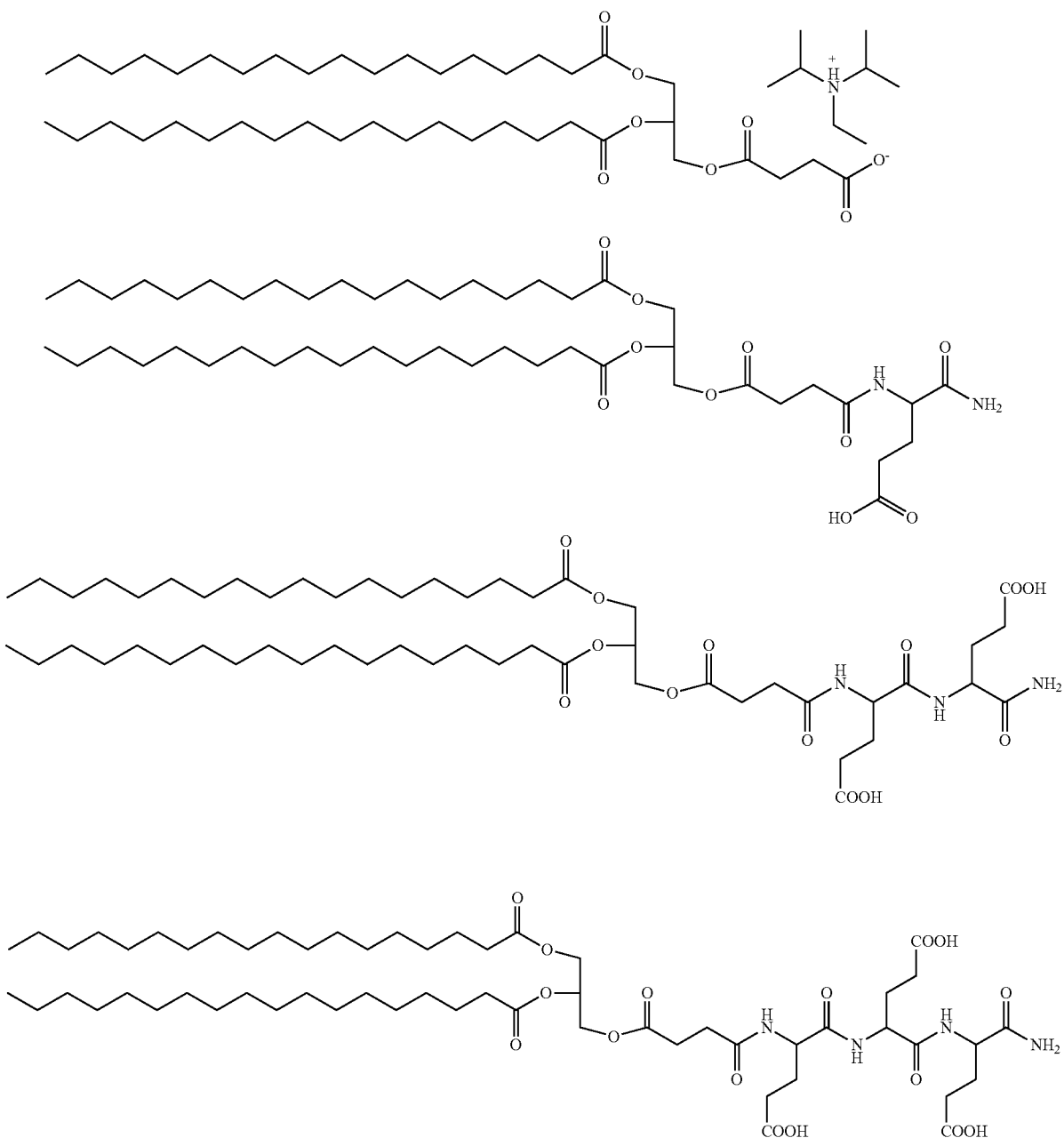

-continued

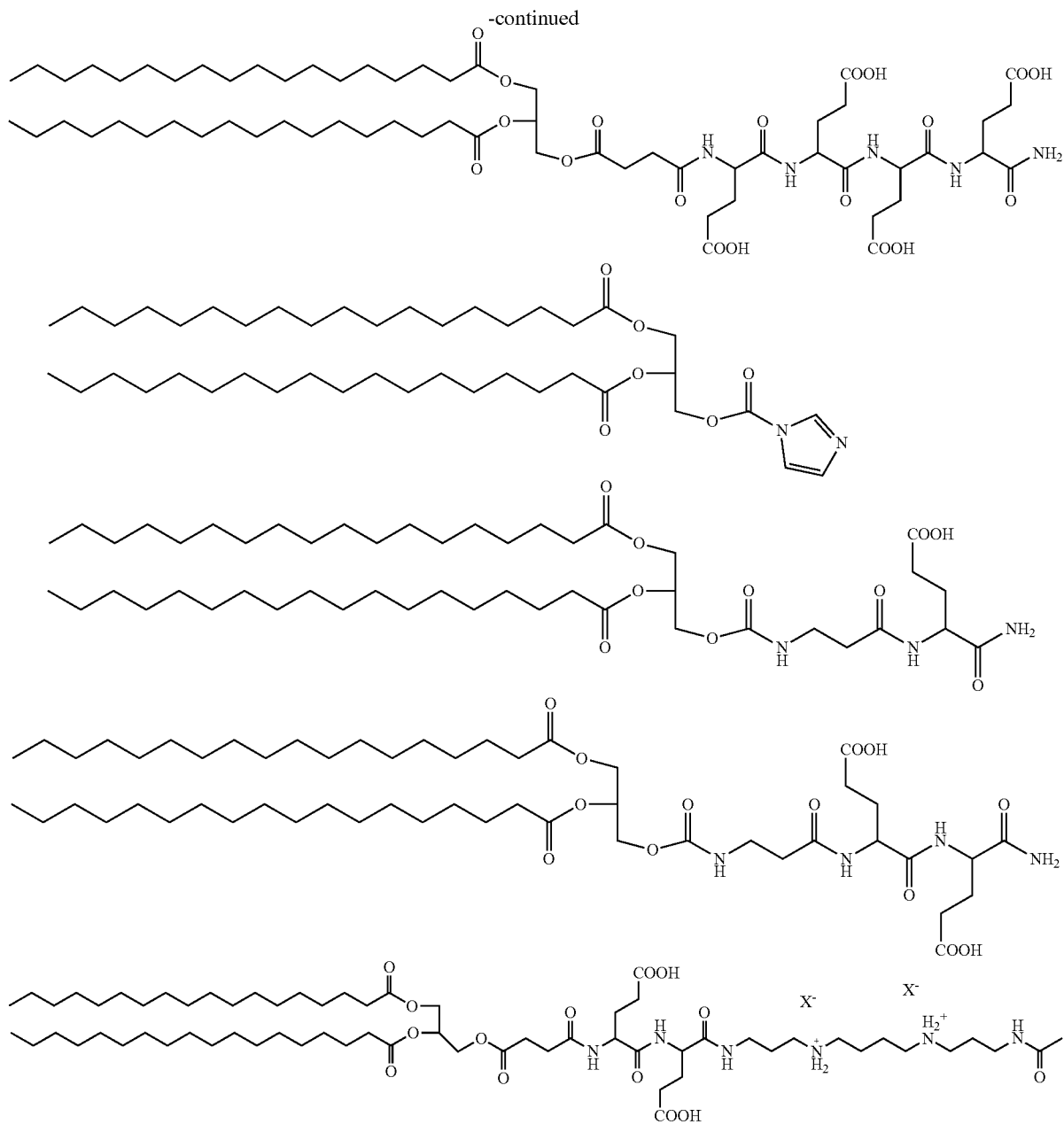

X: CF$_3$COO$^-$, CH$_3$COO$^-$ or Cl$^-$

When used as part of a lipid assembly, the latter comprises one or more additional lipids, at least one of which being a zwitterionic lipid.

In some embodiments, at least one of the one or more additional lipids is a vesicle-forming lipid. In the context of the present invention, the term "vesicle forming lipids" denotes primarily glycerophospholipids or sphingomyelins that form in water into vesicles, such as, but without being limited thereto, liposomes.

Generally, glycerophospholipids have a glycerol backbone wherein at least one, preferably two, of the hydroxyl groups at the head group is substituted by one or two of an acyl, alkyl or alkenyl chain, a phosphate group, or combination of any of the above, and/or derivatives of same and may contain a chemically reactive group (such as an amine, acid, ester, aldehyde or alcohol) at the head group, thereby providing the lipid with a polar head group. The sphingomyelins consist of a ceramide unit with a phosphorylcholine moiety attached to position 1 and thus in fact is an N-acyl sphingosine. The phosphocholine moiety in sphingomyelin contributes the polar head group of the sphingomyelin.

In the vesicle forming lipids the acyl, alkyl or alkenyl chain is typically between 14 to about 24 carbon atoms in length, and have varying degrees of saturation being fully, partially or non-hydrogenated naturally occurring lipids, semi-synthetic or fully synthetic lipids and the level of saturation may affect rigidity of the vesicle thus formed (typically lipids with saturated chains are more rigid than lipids of same chain length in which there are un-saturated chains, especially having cis double bonds).

As noted above, at least one of the one or more additional lipids is a zwitterionic lipid. Choline-type phospholipids such as diacylglycero-phosphocholine (the acyl, alkyl or alkenyl chain being as defined above) are widely used as a zwitterionic lipid that forms a vesicle. The zwitterionic lipid may contain saturated or unsaturated acyl chains.

In some embodiments, the zwitterionic lipid is di-lauroyl-sn-glycero-2-phosphocholine (DLPC). In some embodiments, the zwitterionic lipid is 1,2-dimyristoyl-sn-glycero-3-phosphocholine (DMPC). In some embodiments, the zwitterionic lipid is 1,2-dipalmitoyl-sn-glycero-3-phosphocholine (DPPC). In some embodiments, the zwitterionic lipid is 1,2-dipalmitoyl-sn-glycero-3-phosphocholine (DPPC). In some embodiments, the zwitterionic lipid is 1,2-diheptadecanoyl-sn-glycero-3-phosphocholine. In some embodiments, the zwitterionic lipid is 1,2-distearoyl-sn-glycero-3-phosphocholine (DSPC). In some embodiments, the zwitterionic lipid is 1,2-dinonadecanoyl-sn-glycero-3-phosphocholine. In some embodiments, the zwitterionic lipid is 1,2-diarachidoyl-sn-glycero-3-phosphocholine (DBPC). In some embodiments, the zwitterionic lipid is 1,2-dihenarachidoyl-sn-glycero-3-phosphocholine. In some embodiments, the zwitterionic lipid is 1,2-dibehenoyl-sn-glycero-3-phosphocholine 1,2-ditricosanoyl-sn-glycero-3-phosphocholine. In some embodiments, the zwitterionic lipid is 1,2-dilignoceroyl-sn-glycero-3-phosphocholine. In some embodiments, the zwitterionic lipid is 1-myristoyl-2-stearoyl-sn-glycero-3-phosphocholine. In some embodiments, the zwitterionic lipid is 1-palmitoyl-2-stearoyl-sn-glycero-3-phosphocholine (PSPC). In some embodiments, the zwitterionic lipid is 1-stearoyl-2-palmitoyl-sn-glycero-3-phosphocholine (SPPC). In some embodiments, the zwitterionic lipid is hydrogenated soy phosphatidylcholine (HSPC).

In some embodiments, the zwitterionic lipid is 1,2-di-oleoyl-sn-glycero-3-phosphocholine (DOPC) or di-lauroyl-sn-glycero-2phosphocholine (DLPC).

In one preferred embodiment, the zwitterionic lipid is 1,2-di-oleoyl-sn-glycero-3-phosphocholine (DOPC).

In some embodiments the lipid assembly may also comprise a sterol, such as cholesterol.

The lipid assembly may be characterized by commonly acceptable parameters, making use of analytical techniques available to those versed in biochemistry.

The lipids forming the lipid assembly may be characterized by its zeta potential. Zeta potential measures the magnitude of the electrostatic or charge repulsion/attraction between particles, and thus it can be used as an indicator of stability of the liposomes. Zeta potential measures particle mobility, by measuring the electrostatic surface potential. In accordance with some embodiments, zeta potential is measured by electrostatic potential particle-by-particle, through dynamic light scattering, static light scattering, size exclusion chromatography or electrophoretic light scattering. In accordance with some embodiments, the zeta potential of the lipid assembly is between −2.0 mV to +2.0 mV. Such potential is to be considered as essentially having zero net charge. In some embodiments, the zeta potential of the lipid assembly is ~0.0 mV.

The amphoteric lipids forming the lipid assemblies are characterized as being pH dependent, based on their inclusion of functional groups that are modulated by the surrounding pH. In other words, the lipids are responsive to changes in the external pH of the medium. Such lipids are thus suitable for use in drug delivery systems such as liposomes and micelles, and others, either during or after self-assembly. The lipids are characterized by being positively charged at pH below their pKa and negatively charged at a pH above their pKa, while around their pKa the zeta potential is close to null. This property may be regarded as a feature unique to amphoteric lipids (as opposed, for example, to zwitterionic lipids which have a zeta potential around null over a large pH range).

Due to the formation of the lipid assemblies from amphoteric lipids combined with zwitterionic lipids, the lipid assemblies may be similarly characterized by the zeta potential of the amphoteric lipids from which they are composed.

The lipid assembly may also be characterized by its size distribution. The size distribution may be measured (without being limited thereto) on Malvern Nano Zetasizer and refined by Zetasizer software. The size of the lipid assemblies may be manipulated based on the desired application, making use of commonly available down-sizing techniques. For example, the lipid assemblies may be down-sized by extrusion through membranes with preselected mesh dimensions.

In some embodiments, the size distribution of the lipid assembly is between 100 nm and 5,000 nm.

In some embodiment, the average size of the lipid assemblies is between 80 nm-180 nm; at times between 180 nm-250 nm; at times, between 250-500 nm; at times between 500 nm to 1,000 nm. In some embodiments, the size distribution is such that between 60% to 90% of the assemblies have a diameter in the range of 500-1000 nm and up to 20% have a diameter in the range of 1000 nm to 4,500 nm.

The lipid assembly may also be characterized by the mole ratio between the zwitterionic lipid and the amphoteric lipid. Lipid ratio may be determined using conventional and acceptable techniques.

In some embodiments, the lipid assembly comprises a ratio of between 1 mole to 30 mole of said amphoteric lipid for every 100 mole of the zwitterionic lipid (or the combination of the zwitterionic lipid and any other, non-amphoteric lipid), at times, between 1 mole to 15 mole to 100 mole of the non-amphoteric lipid(s). In some embodiments, the lipid assembly comprises no more than 30 mole, at times no more than 29, 28, 27, 26, 25, 24, 23, 22, 21, 20, 19, 18, 17, 16, 15, 14, 13, 12, 11, 10, 9, 8, 7, 6, 5, 4, 3, 2, 1 mole of said amphoteric lipid. In some embodiments, the lipid assembly comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 mole of said amphoteric lipid per 100 mole of the non-amphoteric lipids in the lipid assembly.

In some embodiments, the ratio between the zwitterionic lipid(s) and the amphoteric lipid(s) is about 100:10±5 mole ratio.

The lipid assembly may also be characterized by its stability, including one or both of chemical and physical stability under storage conditions (4° C., in buffer) for at least three months.

In this context, chemical stability may be examined, inter alia, by one or more of the following parameters:

a) Measurement of dispersion pH (pH meter);

b) phospholipid (PL) acylester hydrolysis by determination of change in non-esterified (free) fatty acids (NEFA) released upon PL hydrolysis [Barenholz et. al. From Liposomes: a practical approach, $2^{nd}$ ed., RRC New Ed, IRL Press Oxford, 1997] or by thin layer chromatography (TLC) [Barenholz, Y. and Amsalem, S. In: Liposome Technology, $2^{nd}$ ed., G. Gregoriadis (Ed.) CRC Press, Boca Raton, 1993, vol. 1, pp: 527-616].

Physical stability of the lipid assemblies may be examined, inter alia, by one or more of the following parameters:

a) assembly size distribution by dynamic light-scattering (DLS).
b) Level of free (non-associated/aggregated) component.
c) zeta potential.

Based on the chemical and/or physical stability, the lipid assemblies of the present disclosure were found to be stable. The "stability" in this context denotes that no more than 30%, 20%, at times 10% of the assemblies disintegrated or otherwise altered (e.g. in content, size etc) when stored at 4° C. and for a period of at least 3 months.

In some embodiments, the lipid assembly comprises a lipopolymer. Lipopolymers comprise lipids modified at their head group with a polymer having a molecular weight equal or above 750 Da. The head group may be polar or apolar, to which a large (>750 Da) a flexible hydrophilic polymer is attached. The attachment of the hydrophilic polymer head group to the lipid region may be a covalent or non-covalent attachment, however, is preferably via the formation of a covalent bond (optionally via a linker).

In some embodiments, the lipopolymer comprises polyols.

There are numerous polymers which may be attached to lipids to form a lipopolymer in the context of the present disclosure. Polymers typically used as lipid modifiers include, without being limited thereto: polyethylene glycol (PEG), polysialic acid, polylactic (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyl-oxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers.

The lipids derivatized into lipopolymers may be neutral, negatively charged, as well positively charged, i.e. there is not restriction to a specific (or no) charge. For example the neutral distearoyl glycerol and the negatively charged distearoyl phosphatidylethanolamine, may both be covalently attached to methoxy poly(ethylene glycol) (mPEG or PEG) of Mw 750, 2000, 5000, or 12000 [Priev A, et al. Langmuir 18, 612-617 (2002); Garbuzenko O., Langmuir 21, 2560-2568 (2005)]. The most commonly used and commercially available lipids derivatized into lipopolymers are those based on phosphatidyl ethanolamine (PE), usually, distearyl-phosphatidylethanolamine (DSPE).

In accordance with some embodiments, the lipopolymer includes methoxy PEG-DSPE (with different lengths of PEG chains) in which the PEG polymer is chemically linked to a lipid (in this case to DSPE). The PEG moiety may have has a molecular weight of the head group is from about 750 Da to about 5,000 Da.

In some embodiments, the PEG is linked to the DSPE primary amino group via a carbamate linkage. One specific PEG-DSPE is $^{2000}$PEG-DSPE ($^{2k}$PEG-DSPE).

In some embodiments, the PEG is linked to a lipid via a linker. In some embodiments, the linker is a sorbitan group. In this embodiment, the PEG has a molecular weight range of between 750-2,000 Da.

In some embodiments, the lipopolymer is polyoxyethylene (20) sorbitan monolaurate (also known as Tween 20).

In some embodiments, the lipopolymer is polyoxyethylene (20) sorbitan monopalmitate (also known as Tween 40).

In some embodiments, the lipopolymer is polyoxyethylene (20) sorbitan monostearate (also known as Tween 60).

In some embodiments, the lipopolymer is Polyoxyethylene (20) sorbitan monooleate (also known as Tween 80).

Without being bound by theory, it is believed that there is an advantage of having a relatively short PEG chain, as in Tween 40 or 60 or 80. This is based on the non-limiting assumption that the long PEG will remain in the formulation for a long time and thus may interfere with the interaction of the formulation with the cells and interfere with the endosomal release of the active substances carried by the lipid assembly into the cell.

In some embodiments, the lipid assembly is utilized for carrying a polynucleotide.

In the context of the present disclosure "polynucleotide" refers to a nucleotide sequence comprising deoxyribonucleic acid (DNA) or ribonucleic acid (RNA). The terms are to be understood to include, as equivalents, analogs of either RNA or DNA made from nucleotide analogs.

In some more specific embodiments, the lipid assembly is utilized for carrying an oligonucleotide. In the context of the present disclosure "oligonucleotide" refers to a deoxyribonucleotide or ribonucleotide sequence from about 2 to about 100 nucleotides. Each DNA or RNA nucleotide in the oligonucleotide may be independently natural or synthetic, and or modified or unmodified. Modifications include sugar, base and internucleotide modifications. An oligonucleotide as disclosed herein includes single-stranded molecules and double-stranded molecules, which modulate gene expression. "Modulate gene expression" includes downregulating (e.g. siRNA, anti-miRNA) gene expression or upregulating (e.g. saRNA) gene expression.

Oligonucleotide includes antisense molecules (molecules which cleave via the RNAi or RNAseH mechanism and include DNA, RNA or DNA/RNA chimera), double stranded RNA (dsRNA) including siRNA, siNA, miRNA, saRNA, and the like, anti-miRs, miR mimetics, ribozymes, aptamers, exon skipping molecules, synthetic mRNA and the like.

In some embodiments, the oligonucleotide is a RNA interference (RNAi) oligonucleotide. An RNAi oligonucleotide is a nucleic acid based molecule capable of inducing RNA interference through interaction with the RNA interference pathway machinery of mammalian cells to degrade or inhibit translation of messenger RNA (mRNA) transcripts of a transgene in a sequence specific manner Two primary RNAi oligonucleotides are the small (or short) interfering RNAs (siRNA) and microRNAs (miRNA or miR). RNAi oligonucleotides may be for example, RNA antisense, siRNA, siNA, miRNA, double-strand RNA (dsRNA), short hairpin RNA (shRNA). RNAi oligonucleotides may be chemically synthesized using standard synthesizers or recombinantly synthesized using expression cassettes encoding RNA capable of inducing RNAi. In some embodiments the oligonucleotide is a single-stranded oligonucleotide or a double-stranded oligonucleotide. Single-stranded oligonucleotides include antisense molecules (DNA, RNA or DNA/RNA chimeras) and anti-miRNA, inter alia. Double-stranded oligonucleotides include siRNA, siNA, shRNA and miRNA mimetics.

RNAi oligonucleotides may be chemically synthesized using standard synthesizers or recombinantly synthesized using expression cassettes encoding RNA capable of inducing RNAi. RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

siRNA comprises a double stranded structure typically containing 15-49 base pairs and preferably 18-25 base pairs and having a nucleotide sequence identical (perfectly complementary) or nearly identical (partially complementary) to a coding sequence in an expressed target gene or RNA within the cell. A siRNA may have dinucleotide 3' overhangs.

In some embodiments the double-stranded molecule further comprises at least one modified ribonucleotide selected from the group consisting of a ribonucleotide having a sugar modification, a base modification or an internucleotide linkage modification and may contain one or more unconventional moiety including DNA, TNA (threose nucleic acid), LNA (locked nucleic acid), ENA (ethylene-bridged nucleic acid), L-DNA or L-RNA, PNA (peptide nucleic acid), PMO (phosphorodiamidate morpholino), arabinoside, phosphonocarboxylate or phosphinocarboxylate nucleotide (PACE nucleotide), or nucleotides with a 6-carbon sugar. All analogs of, or modifications to, a nucleotide/oligonucleotide are employed with the molecules described herein, provided that said analog or modification does not substantially adversely affect the properties, e.g. function, of the nucleotide/oligonucleotide.

In another embodiment, the lipid assembly provided herein may be used for therapeutic applications. The lipid assembly may be used for delivering mimetic microRNAs as well as anti-microRNAs. The delivery of mimetic microRNAs is particularly useful for restoring microRNA expression in conditions (e.g. diseases) in which endogenous microRNA expression is consistently reduced. Mimetic microRNA molecules are delivered as double-stranded RNA, which replace the activity of the endogenous corresponding microRNA. MicroRNA mimetics can be modified to have enhanced efficiency by increasing the affinity for a specific target and by reducing other unwanted microRNA effects. As such, in cancer therapy mimetic microRNAs are viewed as tumor suppressors, while anti-miRs reduce oncogenic microRNA activity.

hsa-miR-34a was shown to have tumor suppressor activity (WO 2008/104974) and its replacement in cancers has great therapeutic value. The lipid assembly presented herein exhibits an improved performance for delivery of hsa-miR-34a, compared to that of naked hsa-miR-34a, or even comparing to the hsa-miR-34a-SL conjugate.

In another further embodiment, the lipid assembly provided herein may be used in the delivery of anti-microRNAs. Anti-microRNAs are antisense oligonucleotides that, when delivered to the cell, bind directly to the endogenous microRNAs and block their activity. The delivery of anti-microRNAs is important for blocking microRNA activity in conditions (e.g. diseases) in which expression is consistently enhanced. The anti-microRNAs work by stoichiometric interaction with mature microRNAs, either titrating them from biologically active pools of mature microRNAs or binding to microRNA precursors and inhibiting the biogenesis of mature microRNAs. Generally, an anti-microRNA is "antisense" to a target nucleic acid (a target miR) when, represented in the 5' to 3' direction, it comprises the reverse complement of the corresponding region of the miR.

In some embodiments nucleotides within the oligonucleotide are selected from those having naturally occurring or synthetic modified bases. Naturally occurring bases include adenine, guanine, cytosine, thymine and uracil. Modified bases of nucleotides include pyrazolotriazine, inosine, xanthine, hypoxanthine, 2-aminoadenine, 6-methyl, 2-propyl and other alkyl adenines, 5-halouracil, 5-halocytosine, 6-azacytosine and 6-az thymine, pseudouracil, deoxypseudouracil, 4-thiouracil, ribo-2-thiouridine, ribo-4-thiouridine, 8-haloadenine, 8-aminoadenine, 8-thioladenine, 8-thiolalkyl adenines, 8-hydroxyl adenine and other 8-substituted adenines, 8-haloguanines, 8-aminoguanine, 8-thiolguanine, 8-thioalkylguanines 8-hydroxylguanine and other substituted guanines, other aza and deaza adenines, other aza and deaza guanines, 5-methylribouridine, 5-trifluoromethyl uracil, 5-methylribocytosine, and 5-trifluorocytosine. In some embodiments one or more nucleotides in an oligomer is substituted with inosine.

Exemplary oligonucleotides as well as sphingolipid-polyalkylamine oligonucleotides are described in detail in International patent application Publication No. WO2015/015496 the content of which is incorporated herein, in its entirety, by reference.

The specific microRNAs disclosed herein are used as examples and should not, in any way, be construed as limiting the scope of the present invention to a specific microRNA. The lipid assembly described herein is for delivery of any microRNA (mimetic or anti-miR) known to the man skilled in the art, and/or which have been published in the "miRBase Sequence Database".

In some embodiments, the oligonucleotide comprises a double-stranded short RNA sequence, corresponding to microRNA or a variant thereof.

As used herein, the variant may be a perfect or imperfect complement of the referenced nucleotide sequence. Alternatively, the variant may be a nucleotide sequence that is substantially identical to the referenced nucleotide sequence or the complement thereof. The variant may also be a nucleotide sequence which hybridizes under stringent conditions to the referenced nucleotide sequence, complements thereof (like an anti-miR sequence complement to the miRNA), or nucleotide sequences substantially identical thereto. The variant may be a portion of a referenced oligonucleotide sequence.

In one embodiment, the oligonucleotide comprises the sequence of the microRNA corresponding to the DICER precursor, also known as the pre-microRNA. Alternatively, the oligonucleotide comprises the sequence of the microRNA hairpin.

In one specific embodiment, the oligonucleotide comprises the sequence of any one of hsa-miR-34a, hsa-miR-34b or hsa-miR-34c, whose sequences have been disclosed herein in the Sequences Tables provided below.

In another specific embodiment, the oligonucleotide comprised in the lipid assembly described herein is a double-stranded nucleotide, comprising the sequence of the microRNA with one, two or three nucleotides as overhang at the 5' or at the 3' end of the duplex. Alternatively, the double-stranded nucleotide may have one or two mismatches between the sense and the anti-sense sequence, forming intra-molecule bulges.

In another specific embodiment, the oligonucleotide is double-stranded having a sequence corresponding to the sequence of microRNA.

The oligonucleotide comprised in the lipid assembly of the invention may also comprise a sequence of a pre-miRNA or a variant thereof. The pre-miRNA sequence may comprise from 45-200, 60-80 or 60-70 nucleotides. The sequence of the pre-miRNA may comprise the -5p and the -3p strands, as set forth herein. The sequence of the pre-miRNA may also be that of a pri-miRNA excluding from 0-160 nucleotides from the 5' and 3' ends of the pri-miRNA.

The oligonucleotide may comprise a miRNA sequence comprising from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

As referred to herein, the term "double stranded oligonucleotide" refers to a complex of ribonucleic acid molecules, having a duplex structure comprising two antiparallel and substantially complementary, as defined above, nucleic acid strands. The two strands forming the duplex structure may be different portions of one larger RNA molecule, or they may be separate RNA molecules. Where separate RNA molecules, such dsRNA are often referred to in the art as siRNA ("short interfering RNA") or DsiRNA ("Dicer substrate siRNAs"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. In addition, as used herein, "dsRNA" may include chemical modifications to ribonucleotides, internucleoside linkages, end-groups, caps, and conjugated moieties, including substantial modifications at multiple nucleotides and including all types of modifications disclosed herein or known in the art.

When referring to "duplex region", it is meant to refer to the region in two complementary or substantially complementary oligonucleotides that form base pairs with one another, either by Watson-Crick base pairing or other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region.

As referred to herein "Substantial complementarity" refers to complementarity between the strands such that they are capable of annealing under biological conditions.

"Sufficiently complementary" (contrasted with, e.g., "100% complementary") allows for one or more mismatches to exist between a dsRNA and the target RNA, provided that the dsRNA possesses complementarity sufficient to trigger the destruction of the target RNA by the RNAi machinery (e.g., the RISC complex) or process. In certain embodiments, a "sufficiently complementary" dsRNA of the invention can harbor one, two, three or even four or more mismatches between the dsRNA sequence and the target RNA or cDNA sequence (e.g., in certain such embodiments, the antisense strand of the dsRNA harbors one, two, three, four, five or even six or more mismatches when aligned with the target RNA or cDNA sequence).

A dicer substrate siRNAs may also bear a mismatch tolerant region, containing one, two, three or four mismatched base pairs of the duplex formed by the sense and antisense strands of the DsiRNA, where such mismatches are positioned within the DsiRNA at a location(s) lying between (and thus not including) the two terminal base pairs of either end of the DsiRNA.

In another embodiment, the oligonucleotide is an anti-miR.

An anti-miRNA comprises the compliment of a micro-RNA sequence.

The lipid assembly is associated with the at least one oligonucleotide by any form of interaction, including, without being limited thereto, entrapment within the lipid assembly (e.g. encapsulation, embedment within the collection of lipids), adhesion, adsorption, anchoring, and the like.

In some embodiments, the oligonucleotide is carried by the lipid assembly as a naked sequence, namely without being associated to a carrier molecule that may be used to facilitate the association of the oligonucleotide with the lipid assembly (as discussed below). In some embodiments, when the oligonucleotide is carried by the lipid assembly as a naked sequence, it is entrapped within the assembly. In some embodiments, the lipid assembly is a liposome and the naked oligonucleotide is encapsulated within the liposome.

In some other embodiments, the oligonucleotide is conjugated to a carrier.

In some embodiments, the carrier is compatible with the lipids forming the lipid assembly. When referring to compatibility it is to be understood as being capable of anchoring or otherwise embedment within the lipid assembly. In some embodiments, the oligonucleotide-carrier conjugate is associated with the lipid assembly with its lipid tail being inserted (anchored) in the lipid bilayer, or in the hydrophobic part of the micelle) and the covalently attached nucleic acid is exposed to the aqueous phase which in the liposomes is facing both the extralipsome medium and the intraliposomal aqueous phase while in the micelles only the extraliposome medium.

In some embodiments, the carrier compatible with the lipid assembly is a lipid tail to the oligonucleotide creating a lipidated nucleic acid.

In some embodiments, the lipid tail is a sterol of a kind that is capable of covalently binding to a nucleic acid. In some embodiments, the lipid tail comprises or is cholesterol (herein "chol"). In some other embodiments, the lipid tail is cholesteryl hemisuccinate where the nucleic acid is bound to the carboxylic acid on the succinate via an ester bond.

In some embodiments, the cholesterol is conjugated to the oligonucleotide via a linker. Such linkers are known in the art, for example Cholesterol TEG (15 atom triethylene glycol spacer TEG-Cholesterol) and $C_6$-Cholesterol. Both cholesterol conjugates could be introduced at either 3' or 5' end of the RNA molecule.

In one embodiment, the oligonucleotide is linked to cholesterol via $(CH_2O)_3(CH_2)_3NHC(O)$—O-Chol (TEG). In some other embodiments, the oligonucleotide is linked to cholesterol via $(CH_2)_6NHC(O)$—O-Chol (C6). In the former case (TEG linker) the cholesterol is introduced at either 3' or 5' end of the RNA.

In some other embodiments, the lipid tail is sphingolipid-polyalkylamine moiety (herein "SL"). To this end, the oligonucleotide may be conjugated to sphingolipid-polyalkylamine phosphoramidite.

The term "sphingolipid-polyalkylamine phosphoramidite" as used herein refers to a sphingolipid-polyalkylamine amidite derivative useful for covalently attaching a sphingolipid-polyalkylamine to a nucleotide.

The terms "sphingolipid-polyalkylamine oligonucleotide molecule" and "sphingolipid-polyalkylamine oligonucleotide compound" are interchangeable and refer to an oligonucleotide linked to a sphingolipid-polyalkylamine conjugate. In some non-limiting embodiments, the sphingolipid-polyalkylamine is a sphingolipid-spermine or a sphingolipid-spermidine.

The SL-oligonucleotide conjugate in the context of the present invention, including the possible oligonucleotides for the purpose of the present invention, are described in detail in International Patent Application Publication No. WO2015/015496 the content of which is incorporated herein, in its entirety, by reference.

The lipid assembly may be characterized by the amount of oligonucleotide loaded onto the assembly. This can be achieved by determining the loading efficiency, e.g. by gel electrophoresis according to which the gel may be stained with SYBR green and fluorescence images may be taken to determine level of fluorescence (e.g. quantified using LAS3000 and calculated using Tina 2.0 software. The calculation is:

$$x = \frac{A-B}{A} * 100\%$$

where x is % of oligonucleotide loading, A is fluorescent signal of appropriate amount of free oligonucleotide and B is fluorescent signal of unbound oligonucleotide fraction of the same amount of oligonucleotide.

At times, the amount of oligonucleotide in the lipid assembly may be presented as the mole % of the oligonucleotide. In some embodiment the mole % of the oligonucleotide is between 0.2 to 5 mole %, at times, between 0.5 to 2.5 mole %, at times, about 0.8 to 1.2 mole %, at times at least 0.2, 0.3, 0.4, 0.5, 0.6, 0.7, 0.8, 0.9, 1.0, 1.1, 1.2, 1.3, 1.4 1.5, 1.6, 1.7, 1.8, 1.9, 2.0, 2.1, 2.2, 2.3, 2.4, 2.5 and any ranges therebetween. In some embodiments, mole % of the oligonucleotide is not more than 3, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5.

At times, and in accordance with some embodiments, the lipid assembly comprises a cationic (or polycationic) lipid, such as N-Palmitoyl Ceramide di (Carbamoyl-Spermine) (PCDCS). Without being bound by theory, such cationic lipid may assist/contribute to the proton sponge effect obtained by the lipid assembly of the present invention. This may be of particular interest when the loading is of oligonucleotides, which in the same environment would be negatively charged.

Cationic lipids are well known in the lipid industry. Cationic lipids (mono and polycationic) have an overall net positive charge. Monocationic lipids may include, for example, 1,2-dimyristoyl-3-trimethylammonium propane (DMTAP) 3β[N—(N,N'-dimethylaminoethane) carbamoly] cholesterol (DC-Chol); and dimethyl-dioctadecylammonium (DDAB). Polycationic lipids may include a lipophilic moiety as with the mono cationic lipids, to which polycationic moiety is attached. Exemplary polycationic moieties include ceramide carbamoyl spermine (N-palmitoyl D-erythro-sphingosyl carbamoyl-spermine, CCS) and N-Palmitoyl Ceramide di (Carbamoyl-Spermine) (PCDCS).

The amount of the cationic lipid may be defined by its mole %. In some embodiments, the amount thereof is between 0.1-3.0 mole %, at times, between 0.2-1.5 mole %, at times 0.5-1.2 mole %, at times, no more than 1 mole %.

In some embodiments, the lipid assembly comprises a targeting moiety. The targeting moiety is typically exposed at least partially at the assemblies' outer surface. The targeting moiety may be any ligand that can associate (covalently or non-covalently) to the outer surface of the lipid assembly and have affinity to a target tissue or target organ.

Some non-limiting targeting moieties include low molecular weight molecules such as folate, or peptides such as Luteinizing-hormone-releasing hormone (LH-RH); the growth inhibiting hormone, somatostatin, proteins such as transferrin; target specific antibodies such as anti-HER2, anti-EGFR, anti-nucleosome. The targeting moiety is typically between 0.1-1.0% out of the total lipid content in the liposome.

In some embodiments, the lipid assemblies are folate-targeted lipid assemblies which are targeted to cells expressing folate receptor such as types of cancer cells. In one embodiment, the cancer is solid cancer, such as, without being limited thereto, brain, breast, prostate, colorectum, kidney; sarcoma; melanoma.

As noted above, the lipid assembly may include any form of organized collection of lipids. In some embodiments, the lipid assembly is a liposomal system, namely, a system comprising an organized collection of lipids forming at least one type of liposomes (the types being possibly different in size, composition, ratio of components, etc). When the lipid assembly is in the form of or comprises liposomes, the combination of the amphoteric lipid(s) and zwitterionic lipid(s) constitute (at times in combination with other components) the liposome's membrane (bilayer) which encloses an internal liposomal core (typically aqueous core).

Liposomes may be categorized according to the number of lamellae and size. Small unilamellar vesicles show a diameter of 20 to approximately 100 nm. Large vesicles, multilamellar vesicles, and multivesicular vesicles range in size from a few hundred nanometers to several microns. The thickness of the membrane (phospholipid bilayer) measures approximately 4 to 5 nm.

In addition, liposomes may have various shapes and sizes. The liposomes may be small or large unilamellar vesicles (SUV, LUV), multilamellar vesicles (MLV) and multivesicular vesicles (MVV) or large multivesicular vesicles (LMVV), which contain several vesicles and, consequently, several separate aqueous phases, as well as oligolamellar vesicles (OLV) [Kulkarni, S. B., et al. J. Microencapsul 12:229-246 (1995)]. MVV liposomes are known to have the form of numerous non-concentric, closely packed internal aqueous chambers separated by a network of lipid membranes and enclosed in a lipid membrane. The vesicles-in-vesicles are formed during the preparation of multivesicular vesicles (MVV) [Szoka, F. and Papahadjopoulos, D. Proc. Natl. Acad. Sci. USA 75:4194-4198(1978)] and the conversion of MLVs into freeze-thawed vesicles (FT MLV) [Kim S. and Martin, G. M. Biochim. Biophys. Acta 646:1-9 (1981)], which are structurally similar to MVVs [Kramer, J. M. H., et al. Biochemistry 17:3932-3935 (1997)]. MVVs and FT MLVs encapsulate far more aqueous phase volume than SUVs and MLVs, but the structures of MVVs and FT MLVs (LMVV) are large, i.e. 0.5-15 μm in diameter.

The selection of the type of liposome to be prepared depends, inter alia, on the intended use. For example, and in accordance with some embodiments, SUV is in the range of and including 20-100 nm. In some other embodiments, MLV is in the range of and including 100-200 nm, or others being larger than 100 nm will be used for local administrations.

Loading of the oligonucleotide into the lipid assemblies, in general, and into the liposomes, in particular, may be by any technique known in the art. Such techniques typically include passive loading or active loading ("remote loading") of agents into vesicles.

Passive loading techniques typically involve loading of the agent during preparation of the vesicles, e.g. either by hydrating dry vesicle forming lipids with a solution comprising the active agent (e.g. the oligonucleotides) or by co-lyophilizing the lipids together with the active agent (nucleic acid) than hydrating the mixture with the desired buffer. By passive loading the agent/oligonucleotide may be associated to the liposomal membrane (e.g. when conjugated to a lipid tail) or encapsulated within the aqueous core. One method for passive loading was described by Bangham, et at, [Bangham A D, et. al. (1965) J Mol Biol. 13(1):238-52], where an aqueous phase containing the agent of interest is put into contact with a film of dried vesicle-forming lipids deposited on the walls of a reaction vessel. Upon agitation by mechanical means, swelling of the lipids occurs and multilamellar vesicles (MLV) are thus formed.

A further method for passive loading is the Reverse Phase Evaporation (REV) method described by Szoka and Papahadjopoulos, [Szoka F. C. $Jr_5$ and Papahadjopoulos D. (1978) *Procedure for preparation of liposomes with large internal aqueous space and high capture by reverse-phase evaporation*. Proc Natl Acad Sci USA. 75(9):4194-8.], according to which a solution of lipids in a water insoluble organic solvent is emulsified in an aqueous carrier phase and the organic solvent is subsequently removed under reduced pressure.

Other methods of passive loading include subjecting liposomes dispersed in the aqueous medium containing the nucleic acid to successive dehydration and rehydration treatment, or freezing and thawing. Dehydration is carried out by evaporation or freeze-drying [Kirby C and Gregoriadis G (1984) *Dehydration-Rehydration Vesicles: A Simple Method for High Yield Drug Entrapment in Liposomes*. Nat. Biotechnol. 2, 979-984], or mixing liposomes prepared by sonication in aqueous solution with the solute to be encapsulated, and the mixture is dried under nitrogen in a rotating flask. Upon rehydration, large vesicles/liposomes are produced in which a significant fraction of the solute has been encapsulated [Shew R L, Deamer D W. (1985) A novel method for encapsulation of macromolecules in liposomes. Biochim Biophys Acta. 816(1):1-8]. Loading may be improved co-lyophilizing the active agent with the dried liposome forming lipids where the mixture o lipids and the active substance in tertiary butanol is lyophyilized (International Patent Application Publication Nos. WO 95/04524 (corresponding to U.S. Pat. No. 6,156,337) and WO 03/000227, the content of which is incorporated herein by reference).

In this respect, and in accordance with some additional aspects of the present disclosure, there is thus provided also a method of preparing the lipid assembly disclosed herein. The method comprises:
providing a dry, preferably lyophilized mixture of lipid components, the mixture comprising at least:
(a) an amphoteric lipid comprising in covalent association:
i) one or more acyl chains;
ii) a weak base moiety;
iii) a weak acid moiety;

(b) a zwitterionic lipid;
hydrating the dry mixture with an aqueous buffer to form the lipid assemblies.

In some embodiments, the aqueous buffer comprises an oligonucleotide to be loaded onto the lipid assembly.

In some embodiments, the aqueous buffer is a Phosphate-Citrate buffer.

In some embodiments, the hydration of the lipids was done with citrate buffer pH 4.3 then the dilution was done with histidine/saline buffer pH 6.5 or PBS.

In some embodiments, the lipid assemblies are subjected to at least two freezing and thawing cycles. In some embodiments, the lipid assemblies are subjected to up to 10 freezing and thawing cycles.

In some embodiments, the lipid assemblies are subjected to between 3 to 8, between 3 to 7, between 4 to 7, between 4 to 6 freezing and thawing cycles.

In some embodiments, the lipid assemblies are subjected to 2, 3, 4, 5, 6, 7, 8, 9, or 10 freezing and thawing cycles.

In accordance with some embodiments, the oligonucleotides are loaded onto the lipid assemblies and the desired resulting form is obtained by rehydration and then successive dehydration and rehydration treatments.

In some embodiments, when the lipid assembly are or comprise liposomes, the oligonucleotide may be either is entrapped or encapsulated within the liposomal aqueous core or be associated to the liposomal bilayer.

In some embodiments, the oligonucleotide is a naked (non-conjugated) oligonucleotide and is encapsulated within the aqueous core of the liposome.

In some other embodiments, when the oligonucleotide is conjugated to a lipid tail as described above and said lipid tail is anchored within the liposomal lipid bilayer. By referring to anchoring it is to be understood that at least a portion of the lipid tail is embedded within the lipid bilayer and the oligonucleotide is exposed at the outer surface of the liposome and/or to the intraliposomal aqueous core of the liposome.

In some embodiments, the lipid assembly carrying the oligonucleotide (naked or conjugated) is in the form of multilamellar vesicles (MLV).

In some embodiments, the lipid assembly carrying the oligonucleotide (naked or conjugated) is in the form of small unilamellar vesicles (SUV).

The lipid assemblies disclosed herein may have various applications.

In accordance with some embodiments, the lipid assemblies may be used as drug delivery systems. To this end, an in accordance with a further aspect of the present disclosure, there is provided a pharmaceutical composition comprising as active ingredient the lipid assembly disclosed herein together with at least one pharmaceutically acceptable carrier.

In some embodiments, the pharmaceutical composition comprises as active ingredient a polynucleotide, and is for use in transfection. In some embodiments, the polynucleotide is an oligonucleotide as defined herein.

In some embodiments, the pharmaceutical composition comprises as active ingredient a polynucleotide or oligonucleotide in an amount effective to inhibit mammalian or non-mammalian gene expression. In some embodiments the mammalian gene is a human gene. In some embodiments the non-mammalian gene is involved in a medical condition, preferably human disease.

In some embodiments, the pharmaceutical composition is used for treating a medical condition which requires modulation of gene expression for its treatment.

In the context of the present disclosure, "treating" refers to administering to a subject (mammalian and non-mammalian) the active ingredient (e.g. the polynucleotide or specifically, the oligonucleotide, in naked or conjugated form), in an amount effective to ameliorate symptoms associated with medical condition, to lessen the severity or cure the medical condition, to slow down the progression of the medical condition, prevent the medical condition from occurring or to postpone the onset of medical condition.

In this context, "treatment" refers to both therapeutic treatment and prophylactic or preventative measures. Those in need of treatment include those already having the medical condition, those prone to having the medical condition, and those in which the medical condition is to be prevented. The lipid assemblies disclosed herein are administered before, during or subsequent to the onset of medical condition to be treated.

In some embodiments, the medical condition is cancer. The terms "cancer" and "cancerous" refer to or describe the physiological condition in mammals that is typically characterized by unregulated cell growth and includes benign and malignant growths. Examples of cancer include but are not limited to, carcinoma, lymphoma, blastoma, sarcoma, and leukemia or lymphoid malignancies. Other examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular tissue.

In line with the above, also provided by the present disclosure is a method of treating a medical condition in a subject, the method comprising administering to the subject in need of treatment a therapeutically effective amount of a lipid assembly carrying an active ingredient, as disclosed herein.

In some embodiments, the subject being treated is a warm-blooded animal and, in particular, a mammal including human.

In some embodiments, the medical condition is cancer.

In some other or further embodiments, the treatment is effected by downregulating target gene whereby the downregulation is selected from the group consisting of downregulation of gene function, down-regulation of polypeptide and down-regulation of mRNA expression.

When referring to down regulation it is to be understood as an effect where there is a change in gene function, protein level or mRNA expression of at least 20%, 30%, or 40%, 50%, 60% or 70%, 75%, 80%, 90% and even 95% as compared to the acceptable control (e.g. before administration).

In accordance with further aspects of the present disclosure there is provided the use of the lipid assembly disclosed herein for the preparation of a pharmaceutical composition as defined herein.

In addition, provided herein is the amphoteric lipid, or the lipid assemblies for use in a method for transfecting into a cell at least one oligonucleotide.

DETAILED DESCRIPTION OF EMBODIMENTS

Synthesis of pH or Electrostatic Modulated/Modified Lipids

The synthesis of modified lipids as disclosed herein involves the use of lipid precursors as follows:

Scheme 1: General structures of lipid precursors.

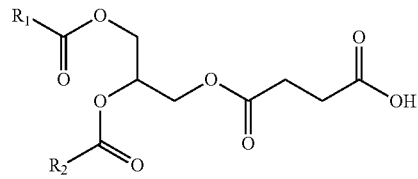

lipid precursor 1

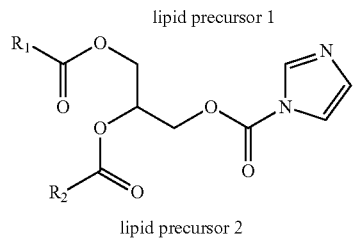

lipid precursor 2

Where:
$R_1$ and $R_2$ = hydrocarbon chain or cholesterol or ceramide ($R_1$ equal or different from $R_2$)

The following synthetic procedures are used to obtain lipid precursors 1 and 2 (Scheme 2 (A) and (B)):

Scheme 2: Modified lipids via ester (B) and carbamate (after nucleophilic attack by amine) (A) linkages. Product of route B is obtained and used as its DIPEA salt.

(A)

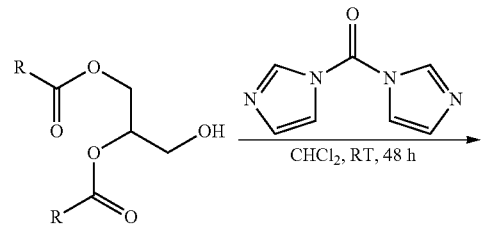

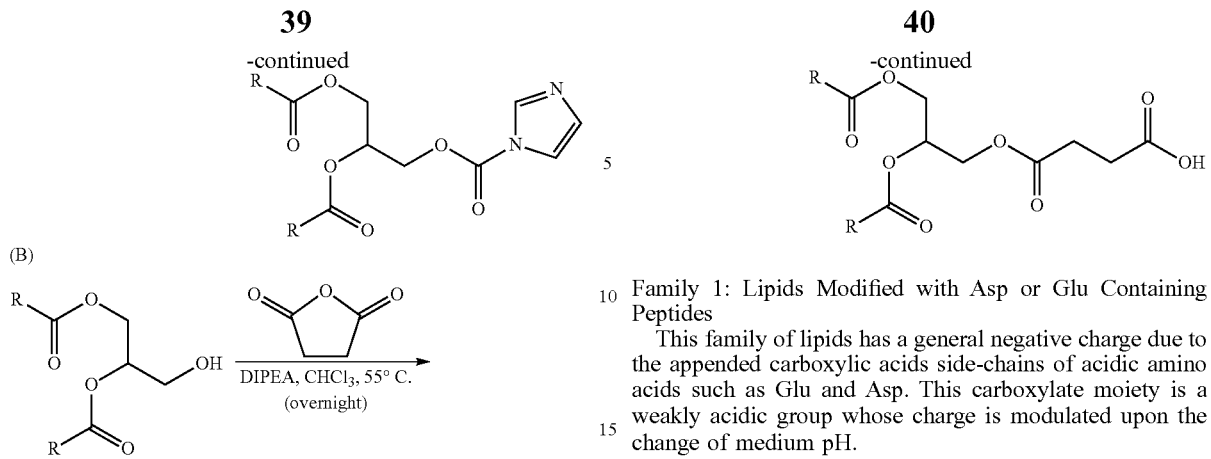

(B)

Family 1: Lipids Modified with Asp or Glu Containing Peptides

This family of lipids has a general negative charge due to the appended carboxylic acids side-chains of acidic amino acids such as Glu and Asp. This carboxylate moiety is a weakly acidic group whose charge is modulated upon the change of medium pH.

The strategy for achieving such Asp or Glu modified lipids is presented in Scheme 3 and Scheme 4.

Scheme 3: Syntheis of lipids modified with acidic amino acids. An ester bond is used to tether the linker to the lipid.

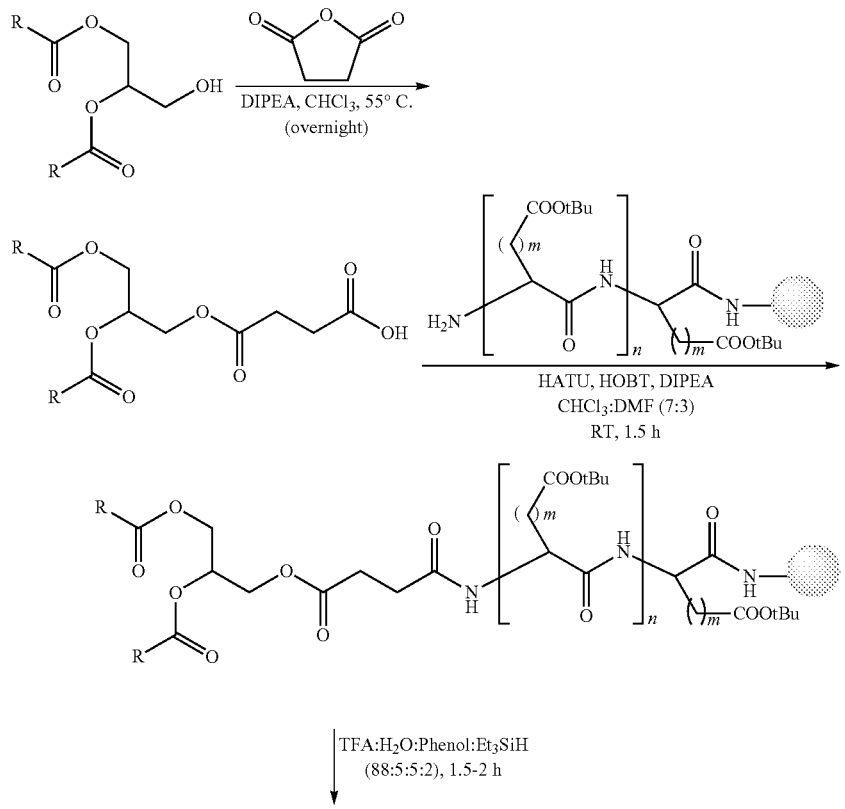

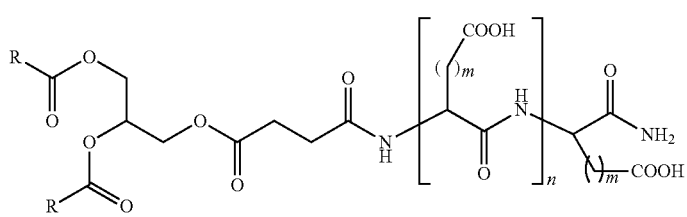

Where: m = 1 or 2
n = 0-3

Scheme 4: Synthesis of lipids modified with acidic amino acids. A carbamate bond is used to tether the linker to the lipid

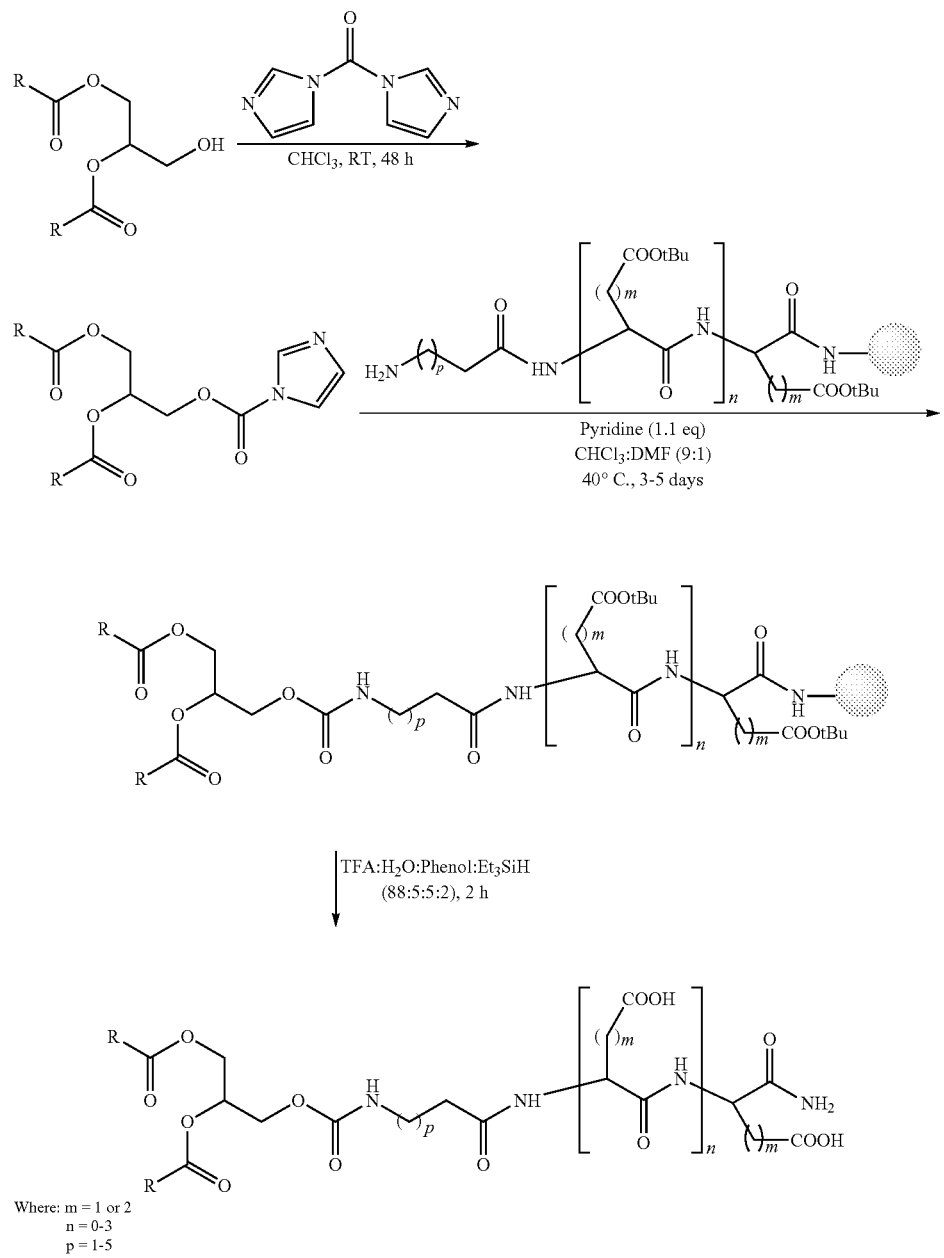

Where: m = 1 or 2
n = 0-3
p = 1-5

Initially the negatively charged peptide is assembled onto the solid support. Next the lipid precursor is coupled (on the resin) followed by deprotection and purification of the desired modified lipid.

In this platform negative and positive charges can be either alternated or divided by negative and positive well-defined sequences.

Family 2: Lipids Modified with Acidic Amino Acids Followed by a Polyalkylamine

In this set of lipids, the overall charge of the lipid is controlled by the number of acidic amino acids vs. the number of amines of the polyalkylamine Here, a polyalkylamine is initially coupled to the solid support (e.g. spermine) and then the primary amine is selectively protected with Dde. Next, the secondary amines are protected with an orthogonal protecting group to Dde (i.e. tBOC). Dde is then selectively removed with 2% hydrazine revealing the primary amine which is further coupled to the acidic peptide followed by the lipid precursor. After cleavage of the modified lipid, the primary amine is acetylated and the BOC groups are removed to obtain the final product as the acetate salt. The overall synthetic approach is presented in Scheme 5.

In Scheme 5, the lipid precursor that is shown is lipid precursor 1 (Scheme 1). Similarly, lipid precursor 2 may be introduced by adding this precursor to the solid support in the presence of 1.1 equivalents of base (pyridine) following the coupling of beta-alanine to the solid support.

Scheme 5: Synthesis of lipids modified with both negative charges (e.g. Glu amino acids) and positive charges (e.g. spermine). This synthetic methodology is also applicable to other linear polyalklamines.
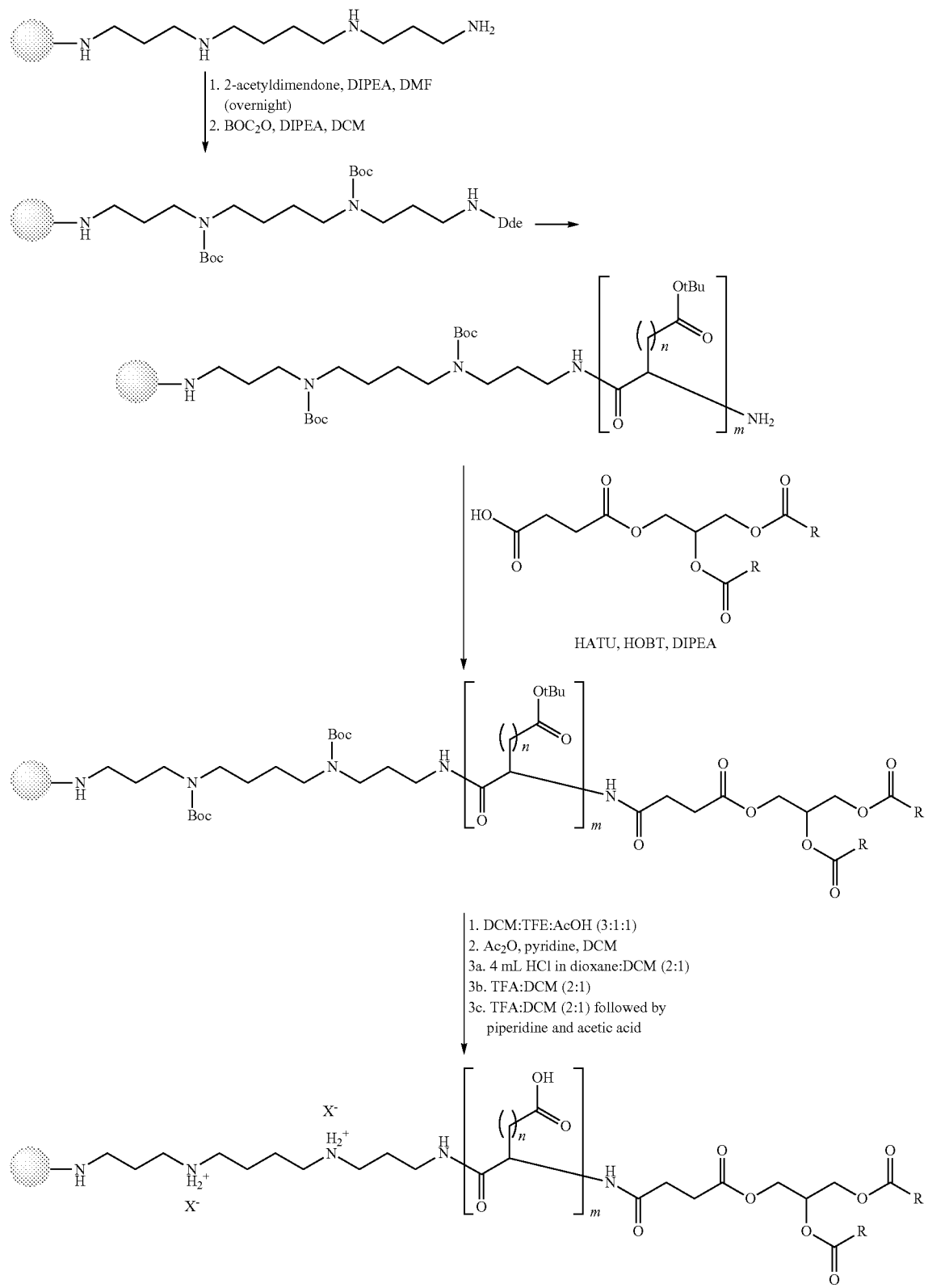

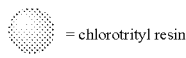 = chlorotrityl resin

Where: n = 1 or 2
m = 1-4
a: X⁻ = Cl⁻; b: X⁻ = CF₃COO⁻
c: X⁻ = CH₃COO⁻

Family 3: Lipids Modified with a Polyalkylamine that is Decorated with Side Chains In this family the synthesis for generating amphoteric lipids is based on the following approach: (1) couple amino-alcohols (e.g. Fmoc-glycinol) to resin by mitsunobu reaction; (2) add lipid precursor to N-terminus; (3) deprotect o-NBS groups followed by cleavage from resin. This synthesis approach is presented in Scheme 6.

Scheme 6 shows the reaction with lipid precursor 1 and is also applicable for lipid precursor 2. $R_1$ and $R_2$ in this Scheme 6 are typical side chains found in natural as well as un-natural amino acids, preferably natural amino acids, where carboxylic acid is most suitable for generating amphoteric lipids.

The number of amino alcohols may vary (two are shown for clarity). R in Scheme 6 is typically a fatty acid but may be any other type of lipid (e.g. cholesterol). The two R groups may be identical or different.

Scheme 6: Synthesis of amphoteric lipids by the mitsunobu reaction of Fmoc-amino acids alcohols on the solid support.

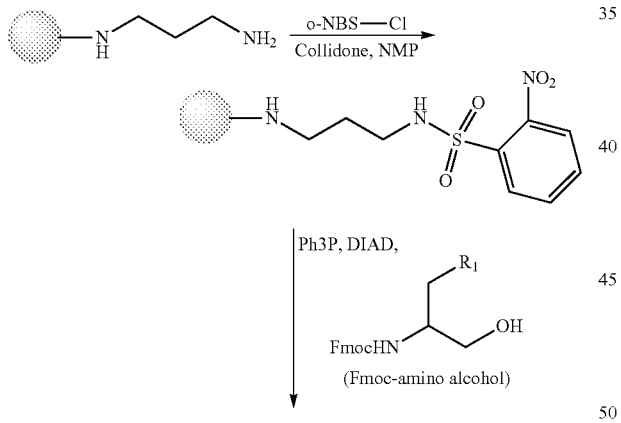

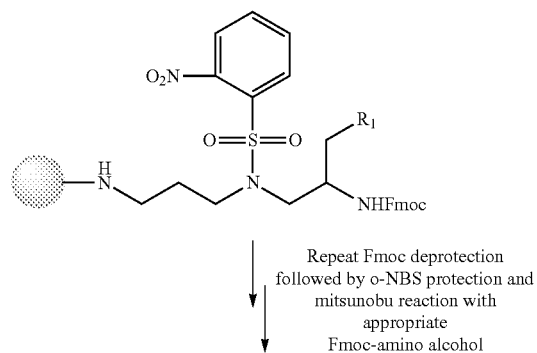

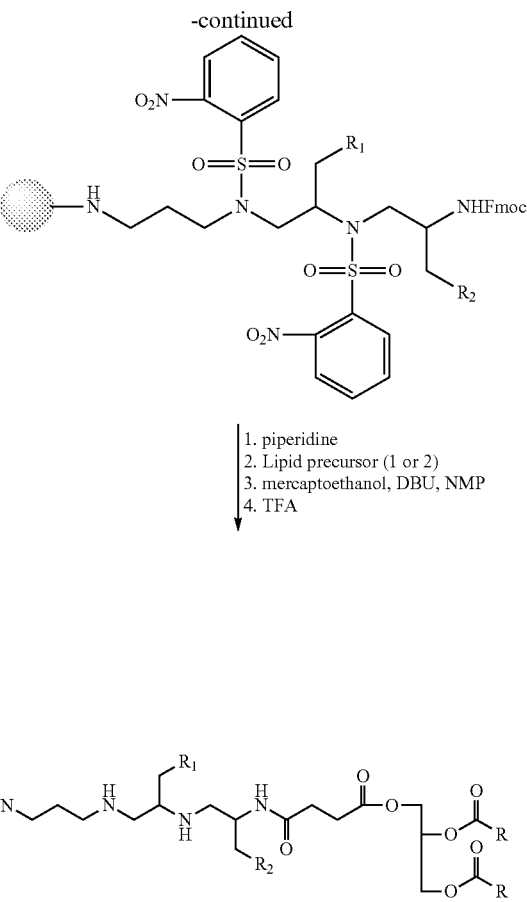

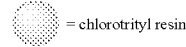 = chlorotrityl resin

Synthesis

Explanation of Nomenclature:

The lipids of Family 1 each have a three-part name composed as lipid-linker-amino acid(s)$_{number\ of\ amino\ acid(s)}$. Abbreviations used are DSG (1,2-di-stearoyl-rac-glycerol), Suc (succinate), Glu (glutamic acid). DSG-Suc-Glu$_3$ is therefore 1,2-di-stearoyl-rac-glycerol coupled to three successive glutamic acids through a succinate linker.

(a) Synthesis of DSG-Suc-COOH, DIPEA Salt (Scheme 2, B)

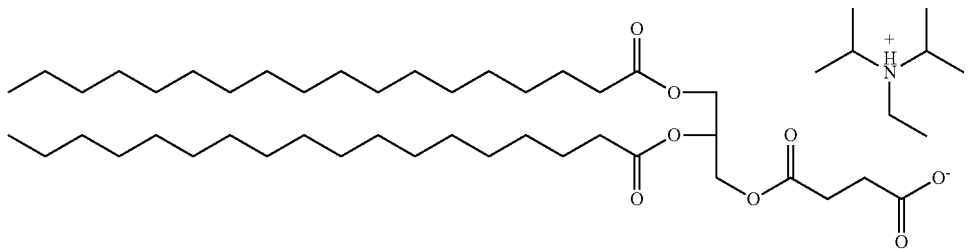

To anhydrous chloroform under an argon atmosphere was added DSG and succinic anhydride in a 1:1 molar ratio. Dry DIPEA was added, the flask was sealed and the mixture was heated to 55° C. and stirred overnight. The mixture was used directly.

ESI-MS (m/z): [M−H]⁻ calcd for $C_{43}H_{79}O_8^-$, 723.58; found, 723.18.

(b) Synthesis of DSG-Suc-Glu1 (Scheme 3)

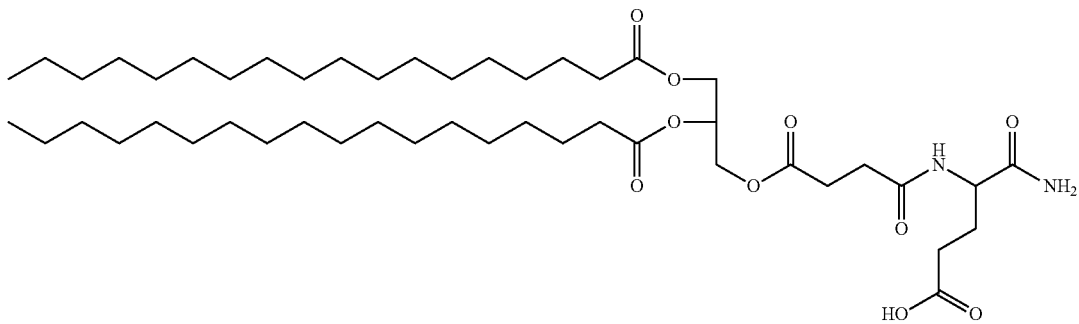 [SMILES: CCCCCCCCCCCCCCCCCC(=O)OCC(COC(=O)CCC(=O)NC(CCC(=O)O)C(N)=O)OC(=O)CCCCCCCCCCCCCCCCC]

DSG-Suc-COOH was prepared as described above using 375 mg DSG (0.6 mmol), 62 mg SA (0.6 mmol), 4.5 mL dry $CHCl_3$, 418 µL DIPEA (2.4 mmol) and a reaction time of 15 hours.

To the obtained solution was added 4.5 mL DMF and 217 mg HATU (0.6 mmol) and 81 mg HOBt.$H_2O$ (0.6 mmol).

The mixture was swirled briefly and added to an N-deprotected glutamic acid residue coupled to a Rink Amide MBHA resin (0.150 mmol) and agitated at room temperature (RT) for 1.5 h under formation of precipitate. In order to dissolve the precipitate additional $CHCl_3$ (2 mL) was added, but the precipitate remained. The reaction mixture was stirred for an additional hour. The resin was drained and washed (DCM×2, DMF×2, DCM×1). The product was cleaved in TFA:$H_2O$:Phenol:$Et_3SiH$ (88:5:5:2) for 1.5 hours. The cleavage cocktail was collected, reduced in vacuo to a few milliliters and injected into ice-cold methanol, causing precipitation.

The suspension was spun down and dried giving 108 mg (85%) of crude product. Purification by flash chromatography in hexane:EtOAc:HOAc (25:75:1) gave 82 mg (65%) of the target compound as a white, crystalline solid.

ESI-MS (m/z): [M−H]⁻ calcd for $C_{48}H_{87}N_2O_{10}^-$, 851.64; found, 851.53.

¹H-NMR (500 MHz, CDCl3): δ 6.92 (m, 2H), 6.02 (m, 1H), 5.28 (m, 1H), 4.62 (m, 1H), 4.33-4.13 (m, 4H), 2.76-2.43 (m, 6H), 2.34 (t, J=7.13, 2H), 2.32 (t, J=7.3, 2H), 2.18 (m, 1H), 2.01 (m, 1H), 1.62 (m, 4H), 1.32-1.27 (br.s, 56H), 0.89 (t, J=7.2, 6H).

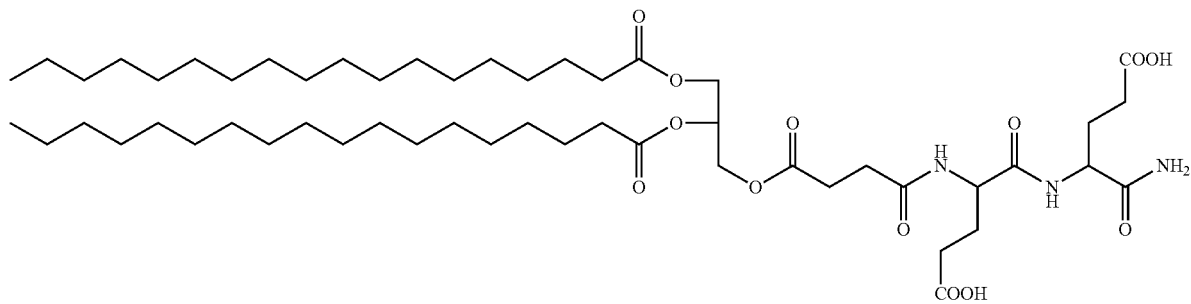 [SMILES: CCCCCCCCCCCCCCCCCC(=O)OCC(COC(=O)CCC(=O)NC(CCC(=O)O)C(=O)NC(CCC(=O)O)C(N)=O)OC(=O)CCCCCCCCCCCCCCCCC]

(c) Synthesis of DSG-Suc-Glu2 (Scheme 3)

DSG-Suc-COOH was prepared as described above using 1134 mg DSG (1.81 μmol), 180 mg SA (1.80 μmol), 10 mL dry CHCl$_3$, 1252 μL DIPEA (7.2 mmol) and a reaction time of 18 hours.

To the obtained solution was added 650 mg HATU (1.71 mmol) and 276 mg HOBt.H$_2$O (1.80 mmol) dissolved in 5 mL DMF.

This mixture was briefly swirled and transferred to an N-deprotected di-glutamic acid residue coupled to a Rink Amide AM resin (0.6 mmol) and agitated at RT for 1.5 hours. The resin was drained and washed (DCM×2, DMF×2, DCM×1). Cleavage was achieved in TFA:H$_2$O:Phenol:Et$_3$SiH (88:5:5:2) for 2 hours. The cleavage cocktail was collected, reduced in vacuo to 5-10 mL and injected into 25 mL ice-cold acetonitrile, causing precipitation.

The suspension was spun down and dried giving 541 mg (92%) of crude product. Addition of 6 mL water to the ACN yielded 20 mg more—561 mg (95%). Purification by flash chromatography in CHCl$_3$:MeOH:H$_2$O:HOAc (90.5:8:1:0.5) gave 385 mg (65%) of the target compound as a white, crystalline solid.

ESI-MS (m/z): [M+H]$^+$ calcd for C$_{53}$H$_{96}$N$_3$O$_{13}{}^+$, 982.69; found, 982.58.

$^1$H-NMR (500 MHz, CDCl$_3$:TFA-d—4:1): δ 5.41 (m, 1H), 4.71 (m, 2H), 4.44-4.20 (m, 4H), 2.86-2.56 (m, 8H), 2.45 (t, J=7.0, 2H), 2.43 (t, J=7.6, 2H), 2.33-2.19 (m, 2H), 2.14-2.03 (m, 2H), 1.64 (m, 4H), 1.33-1.28 (br.s, 56H), 0.89 (t, J=6.9, 6H).

(d) Synthesis of DSG-Suc-Glu3 (Scheme 3)

To the obtained solution was added 325 mg HATU (0.855 mmol) and 122 mg HOBt.H$_2$O (0.90 mmol) dissolved in 3 mL DMF. The reaction mixture was swirled briefly and added to an N-deprotected tri-glutamic acid residue coupled to a Rink Amide MBHA resin (0.3 mmol) and agitated at RT for 55 min.

The resin was drained and washed (DCM×2, DMF×2, DCM×1). Cleavage of product was carried out for 2 h in TFA:H2O:Phenol:Et3SiH (88:5:5:2). The cleavage mixture was collected, reduced in vacuo to a few milliliters and injected into ice-cold acetonitrile, causing precipitation. The suspension was spun down and dried giving 260 mg crude product (78%). Purification by flash chromatography in CHCl$_3$:MeOH:HOAc:H2O (85:15:2:1) gave 167 mg (50%) of the target compound as a white, crystalline solid.

ESI-MS (m/z): [M−H]$^-$ calcd for C$_{58}$H$_{101}$N$_4$O$_{16}{}^-$, 1109.73; found, 1109.40.

$^1$H-NMR (500 MHz, CDCl$_3$:TFA-d—4:1): δ 5.37 (m, 1H), 4.67 (m, 3H), 4.41-4.17 (m, 4H), 2.77-2.58 (m, 10H), 2.42 (t, J=6.9, 2H), 2.41 (t, J=6.9, 2H), 2.28-2.06 (m, 6H), 1.63 (m, 4H), 1.33-1.28 (br.s, 56H), 0.89 (t, J=6.8, 6H).

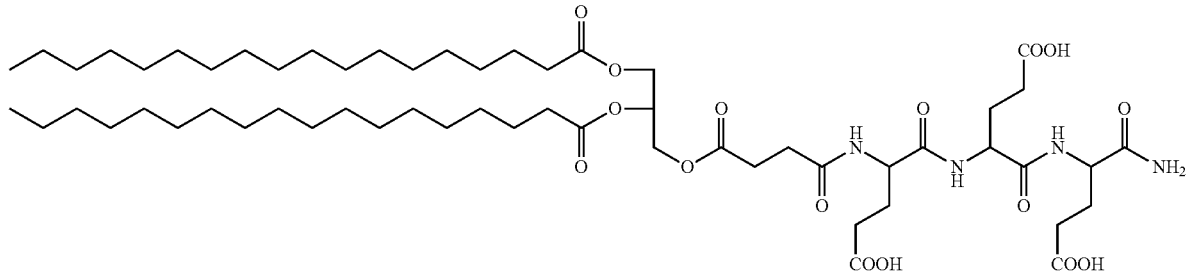 [SMILES: CCCCCCCCCCCCCCCCCC(=O)OCC(COC(=O)CCC(=O)NC(CCC(=O)O)C(=O)NC(CCC(=O)O)C(=O)NC(CCC(=O)O)C(N)=O)OC(=O)CCCCCCCCCCCCCCCCC]

DSG-Suc-COOH was prepared as described above using 563 mg DSG (0.9 mmol), 90 mg SA (0.9 mmol), 7 mL dry CHCl$_3$, 627 μL DIPEA (3.6 mmol) and a reaction time of 21 hours.

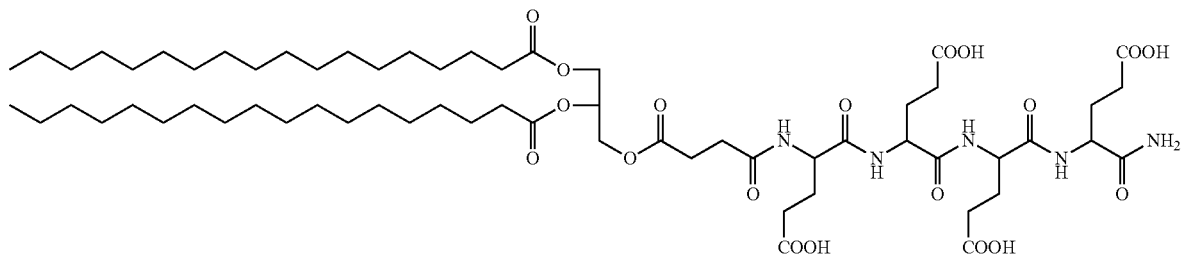 [SMILES: CCCCCCCCCCCCCCCCCC(=O)OCC(COC(=O)CCC(=O)NC(CCC(=O)O)C(=O)NC(CCC(=O)O)C(=O)NC(CCC(=O)O)C(=O)NC(CCC(=O)O)C(N)=O)OC(=O)CCCCCCCCCCCCCCCCC]

(e) Synthesis of DSG-Suc-Glu4 (Scheme 3)

DSG-Suc-COOH was prepared as described above using 1.13 g DSG (1.80 mmol), 180 mg SA (1.80 mmol), 14 mL dry CHCl$_3$, 1.25 mL DIPEA (7.2 mmol) and a reaction time of 22 hours. Half of this mixture was used for DSG-Suc-Glu$_4$ synthesis. To the 7 mL HOOC-Su-DSG mixture (0.9 mmol) was added 325 mg HATU (0.855 mmol) and 122 mg HOBt.H$_2$O (0.9 mmol) dissolved in 3 mL DMF. This mixture was briefly swirled and transferred to an N-deprotected tetra-glutamic acid residue coupled to a Rink Amide MBHA resin (0.3 mmol) and agitated at RT for 1.5 hours. The resin was drained and washed (DCM×2, DMF×2, DCM×2). Cleavage of product was carried out in TFA:H$_2$O:Phenol:Et$_3$SiH (88:5:5:2) for 2 hours. The cleavage mixture was collected and reduced in vacuo. This caused precipitation of white solids. To the resulting suspension was added ice-cold methanol, causing more precipitation. The suspension was spun down and dried giving 369 mg (99%) of crude product. 246 mg of this crude product was dissolved in 100 mL CHCl$_3$:HCOOH (9:1) by heating to 60° C.

DSG (1125 mg, 1.8 mmol) and 1459 mg carbonyldiimidazole (9.0 mmol) were dissolved in 40 mL dry CHCl$_3$, giving a slightly turbid mixture. The reaction mixture was stirred at RT under an argon atmosphere in a sealed flask for 2 days. Addition of ice-cold acetonitrile caused precipitation. The precipitate was washed twice with ice-cold acetonitrile and dried, giving 1200 mg (97%) of the target compound as a white solid.

ESI-MS (m/z): [M−H]$^−$ calcd for C$_{43}$H$_{79}$N$_2$O$_6$$^+$, 719.59; found, 719.42.

1H-NMR (500 MHz, CDCl3) δ 8.12 (s, 1H), 7.41 (s, 1H), 7.09 (s, 1H), 5.41 (dt, J=9.8; 5.2 Hz, 1H), 4.63 (dd, J=12; 3.7 Hz, 1H), 4.50 (dd, J=11.8; 6.2 Hz, 1H), 4.37 (dd, J=12; 4.9 Hz, 1H), 4.22 (dd, J=12; 5.6 Hz, 1H), 3.73 (quart, J=6.9 Hz, 0.87H), 2.33 (m, 4H), 1.62 (m, 4H), 1.26 (br.s. 56H), 0.89 (t, J=6.9 Hz, 6H).

(g) Synthesis of DSG-β-ala-Glu1 (Scheme 4)

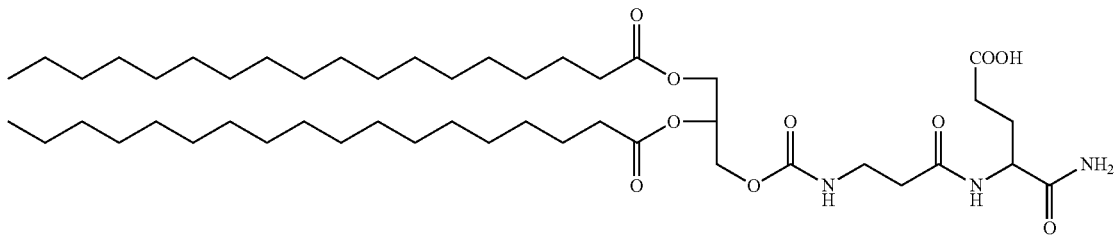

The resulting solution was filtered through filter-paper to remove minute undissolved impurities. The filter was washed with a further 10 mL CHCl$_3$:HCOOH (9:1). This gave an opalescent solution that was re-heated to boiling. Acetonitrile (≈10 mL) was added slowly until precipitation began. This solution was slowly cooled to −20° C., forming copious amorphous precipitate. The mixture was filtered and the precipitate washed with ice-cold acetonitrile, giving 199 mg.

The product was redissolved in 5 mL DCM:TFA (1:1) and triturated by addition of ice-cold acetonitrile (35 mL), giving 165 mg (67%) of the target compound as a white solid.

ESI-MS (m/z): [M−H]$^−$ calcd for C$_{63}$H$_{108}$N$_5$O$_{19}$$^−$, 1238.77; found, 1239.00.

$^1$H-NMR (500 MHz, CDCl$_3$:TFA-d—4:1): δ 5.41 (m, 1H), 4.76-4.63 (m, 4H), 4.44-4.21 (m, 4H), 2.80-2.55 (m, 12H), 2.44 (t, J=7.5, 3H), 2.43 (t. J=7.5, 3H), 2.31-2.19 (m, 4H), 2.12-2.01 (m, 4H), 1.64 (m, 4H), 1.31-1.25 (br.s, 56H), 0.89 (t, J=6.8, 6H).

(f) Preparation of DSG-Im (1,2-distearoyl-3-O-imidazolide, Scheme 2, A)

Fmoc deprotection of Rink Amide AM-GLU-β-ALA-NHFmoc (0.117 mmol) was achieved by treating resin with 25% piperidine/DMF. The resin was placed in an RB-flask along with 168 mg DSG-Im (0.234 mmol, 2 eq). 4.5 mL dry chloroform and 0.5 mL DMF were added, along with 11 µL pyridine (0.129 mmol, 1.1 eq).

An argon atmosphere was established and the flask was sealed and stirred for 3 days at 40° C. Cleavage from resin was carried out in 5 mL TFA:H$_2$O:Phenol:Et$_3$SiH (88:5:5:2) for 2.5 hours. The solution was reduced to a few milliliters in vacuo and triturated with ice-cold acetonitrile (30 mL).

The precipitate was spun down and dried, giving 61 mg (60%) crude product. Addition of 6 mL water to the supernatant gave 7 mg extra precipitate for a total of 67 mg (66%) crude product. Purification by flash chromatography in CHCl$_3$:MeOH:AcOH:H$_2$O (90.5:8:1:0.5) gave 59 mg (58%) of the target compound as a white solid.

ESI-MS (m/z): [M+H]$^+$ calcd for C$_{48}$H$_{90}$N$_3$O$_{10}$$^+$, 868.66; found, 868.54.

$^1$H-NMR (500 MHz, CDCl$_3$): δ 6.81-6.67 (m, 2H), 5.72 (s, 1H), 5.27 (m, 1H), 4.58 (m, 1H), 4.34-4.24 (m, 2H), 4.21-4.11 (m, 2H), 2.76-2.62 (m, 2H), 2.60-2.42 (m, 4H), 2.33 (t, J=7.3 Hz, 2H), 2.31 (t, J=7.5 Hz, 2H), 2.22-2.13 (m,

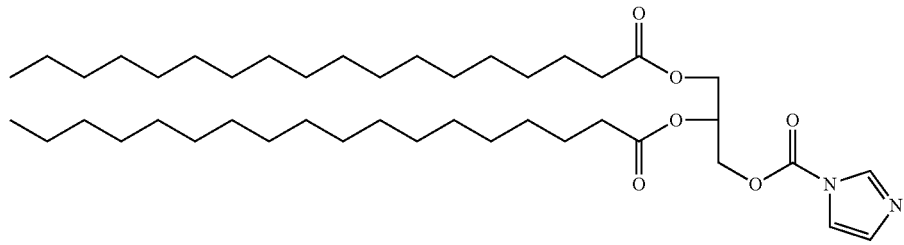 [SMILES: CCCCCCCCCCCCCCCCCC(=O)OCC(COC(=O)n1ccnc1)OC(=O)CCCCCCCCCCCCCCCCC]

1H), 2.06-1.96 (m, 1H), 1.66-1.56 (m, 4H), 1.34-1.23 (br s, 56H), 0.88 (t, J=7.0 Hz, 6H).

(h) Synthesis of DSG-β-ala-Glu2 (Scheme 4)

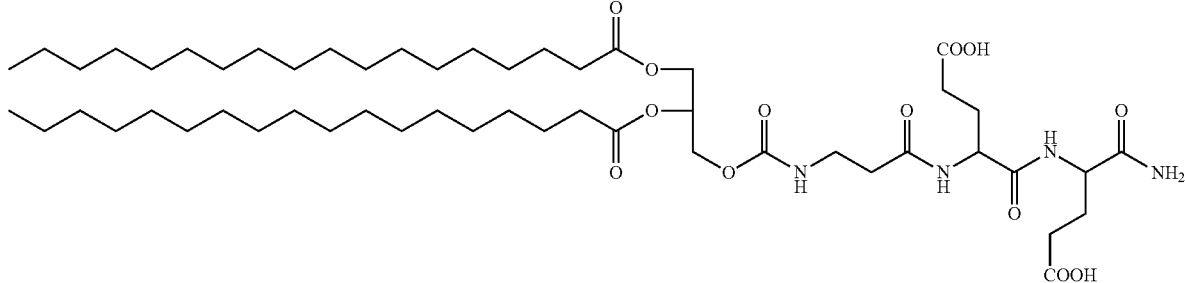 [SMILES: CCCCCCCCCCCCCCCCCC(=O)OCC(COC(=O)NCCC(=O)NC(CCC(=O)O)C(=O)NC(CCC(=O)O)C(N)=O)OC(=O)CCCCCCCCCCCCCCCCC]

Fmoc deprotection of Rink Amide AM-GLU-GLU-β-ALA-NHFmoc (0.150 mmol) was achieved by treating resin with 25% piperidine/DMF. The resin was placed in a round-bottom flask along with 216 mg DSG-Im (0.300 mmol, 2 eq). 4.5 mL dry DCM and 0.5 mL DMF were added, along with 13 μL pyridine (0.165 mmol, 1.1 eq). An argon atmosphere was established and the flask was sealed and stirred for 5 days at 40° C. Resin was washed (DCM×2, DMF×2, DCM×2) and cleaved in 5 mL TFA:H₂O:Phenol:Et₃SiH (88:5:5:2) for 2 hours. The cleavage cocktail was reduced to a few milliliters in vacuo and triturated with ice-cold acetonitrile (10 mL). The precipitate was spun down and dried, giving 73 mg (49%) crude product. Addition of 5 mL water to the supernatant did not give extra precipitate. Purification by flash chromatography in CHCl₃:MeOH:AcOHc:H₂O (90:10:1:1) gave 59 mg (39%) of the target compound as a white solid.

ESI-MS (m/z): [M−H]⁻ calcd for $C_{53}H_{95}N_4O_{13}^-$, 995.69; found, 995.43.

¹H-NMR (500 MHz, CDCl₃:TFA-d—4:1): δ 5.44 (m, 1H), 4.73 (m, 2H), 4.47-4.36 (m, 2H), 4.34-4.22 (m, 2H), 2.87-2.57 (m, 8H), 2.47 (t, J=7.9 Hz, 2H), 2.45 (t, J=7.9 Hz, 2H), 2.35-2.20 (m, 2H), 2.17-2.04 (m, 2H), 1.70-1.60 (m, 4H), 1.34-1.22 (br s, 56H), 0.88 (t, J=7.0 Hz, 6H).

(i) Synthesis of Amphoteric Lipid/Ampholip 1 (Scheme 5)

2-acetyldimedone (2.4 mmol) and 417 μL DIPEA (2.4 mmol). The resin was agitated for three days, drained and washed (DMF×3, DCM×3). To the resin was added a solution of 1048 mg Boc₂O (4.8 mmol) in 15 mL DCM, followed by 2086 μL DIPEA (12 mmol). The mixture was agitated for 3.5 days. The resin was drained and washed (DCM×2, DMF×2, DCM×2). The Dde group was removed by a two-fold treatment with 2% hydrazine monohydrate in DMF for 30 minutes and 45 minutes respectively. The resin was drained and washed (DMF×5, DCM×2). The molecule was extended with two Fmoc-protected glutamic acid residues using standard HATU/HOBt coupling. The terminal Fmoc-group was removed by treatment with 25% piperidine/DMF. A solution of DSG-Suc-COOH had been prepared by letting 908 mg DSG (1.45 mmol) and 147 mg SA (1.45 mmol) dissolved in 14 mL dry CHCl₃ and 1 mL DIPEA (5.78 mmol) to react for 19.5 hours at 55° C. under an argon atmosphere. To this solution was added 522 mg HATU (1.37 mmol) and 211 mg HOBt.H₂O (1.45 mmol). It was swirled briefly, added to the deprotected resin and allowed to react at RT for 1.5 hours. The resin was drained and washed (DCM×2, DMF×2, DCM×1). Cleavage was performed on a quarter of the resin. The fully protected compound was cleaved from the resin by successive treatments with DCM:AcOH:TFE (8:1:1). After each treatment, the mixture was co-evaporated with hexane leaving a yellowish solid. Cleavage cycles were done as follows: 1) 10 mL cleavage cocktail for 2 hours gave 23 mg, 2) 5 mL for

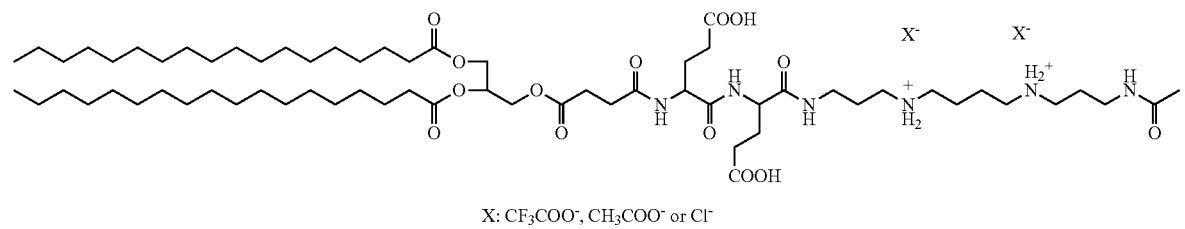

X: CF₃COO⁻, CH₃COO⁻ or Cl⁻

This amphoteric lipid, herein referred to as Ampholip 1 was prepared as follows and the stock was kept as a 1 mM solution in DDW/tert-butanol 1/1:

1.2 g 2-chlorotrityl chloride resin (nominal loading capacity: 1.3 mmol/g) was added to an SPPS-vessel and swelled in 10 mL DCM. To this was added 650 mg spermine (3.2 mmol) and the mixture was agitated for 8 hours, after which the resin was drained and washed (DCM×1, MeOH×1, H₂O×1, DMF×1). Unreacted sites on the resin were capped by agitation for 1 hour in 10 mL MeOH:DCM:DIPEA (3:9:1). Resin was drained and washed (DMF×2, DCM×2). To the resin was added 10 mL DMF, along with 456 mg 4 hours gave 17 mg, 3) 10 mL for 9 hours gave 35 mg, 4) 20 mL for 8 hours gave 43 mg, 5) 20 mL for 8 hours gave 90 mg. A total of 208 mg product was obtained. Purification of 100 mg of the crude product by flash chromatography in a gradient of CHCl₃:MeOH:AcOH (95:5:1)→CHCl₃:MeOH:H₂O:AcOH (85:15:1:1) gave 45 mg (45%) of the fully-protected, free amine, acetate salt species.

ESI-MS (m/z): [M+H]⁺ calcd for $C_{81}H_{151}N_6O_{17}^+$, 1480.11; found, 1480.4.

Capping of Terminal Amine.

155 mg of the fully-protected, free amine, acetate salt (101 μmol) was dissolved in 15 mL dry DCM under a nitrogen atmosphere. To the resulting solution was added 191 µL acetic anhydride (2.02 mmol) and 236 µL pyridine (10.1 mmol). The solution was stirred for 3 hours. The mixture was partitioned between 100 mL water and 100 mL ether. The organic phase was washed with water (2×100 mL). Acetonitrile was added and the solvents were removed in vacuo. Purification by flash chromatography in $CHCl_3$:MeOH (50:1) gave 152 mg (99%) of the fully-protected, N-acetylated species.

ESI-MS (m/z): $[M+Na]^+$ calcd for $C_{83}H_{152}N_6O_{18}Na^+$, 1544.11; found, 1544.4.

Deprotection—Preparation of Chloride Salt.

45 mg of the fully-protected, N-acetylated compound was dissolved in 4 mL 4M HCl in dioxane at RT. 20 µL TIS was added. After 3 minutes of stirring a white precipitate started to form. 2 mL dry DCM was added. The suspension was stirred for 1 hour after which it was added to ice-cold ether. The resulting suspension was spun down, washed with ice-cold ether and dried to give 36 mg (95%) of target compound as the di-chloride salt.

MALDI-TOF MS (DHB, Na) (m/z): $[1\backslash4+H]^+$ calcd for $C_{65}H_{121}N_6O_{14}$, 1209.89, found: 1210.1.

1H-NMR (500 MHz, $CDCl_3$:MeOH—6:1) δ 5.17 (m, 1H), 4.25-4.00 (m, 6H), 3.29-3.21 (m, 4H), 2.91 (m, 8H), 2.69-2.41 (m, 4H), 2.35 (m, 4H), 2.22 (m, 4H), 2.04 (m, 2H), 1.98-1.79 (m, 13H), 1.51 (m, 4H), 1.23-1.13 (m, 56H), 0.79 (m, 6H).

Deprotection—Preparation of TFA Salt.

38 mg of the fully-protected, N-acetylated compound was dissolved in 500 µL DCM and cooled to 0° C. To this solution was added a cooled solution of 3 µL TIS and 3 µL water in 1 mL TFA. The resulting solution was allowed to stand at 0° C. for 100 minutes after which the solution was reduced in vacuo to less than 1 mL. 5 mL ether was added, causing precipitation. After cooling to −18° C. for one hour, the precipitate was spun down, washed with ether and dried, giving 34 mg (95%) of the target compound as the fully-deprotected, di-trifluoroacetate salt.

MALDI-TOF MS (DHB, Na) (m/z): $[M+H]^+$ calcd for $C_{65}H_{121}N_6O_{14}$, 1209.89, found: 1209.6.

$^1$H-NMR (500 MHz, $CDCl_3$) δ 8.98-7.58 (m, 10H), 5.25 (s, 1H), 4.33-4.09 (m, 6H), 3.37-3.02 (m, 12H), 2.70-1.82 (m, 27H), 1.60 (m, 4H), 1.43+1.42 (two singlets, 0.77H, —COOC(CH$_3$)$_3$), 1.30-1.22 (m, 56H), 0.88 (t, J=6.94, 6H).

Conversion of TFA-Salt to Acetate-Salt.

34 mg of the fully-deprotected, di-trifluoroacetate salt was dissolved in 2 mL $CHCl_3$. To the resulting solution was added 1 mL piperidine and the solution was vortexed for 10 minutes. 16 mL diethylether was added. The product precipitated as the di-piperidinium salt after about 30 minutes in the freezer at −18° C. After centrifugation and drying, the pellet was dissolved in 1 mL $CHCl_3$, to which 1 mL AcOH was added. The mixture was vortexed for 10 minutes after which 15 mL ether was added. Placing the mixture in a −18° C. freezer caused precipitation of the fully-deprotected, di-acetate salt.

The disappearance of the TFA counteranions was measured by $^{19}$F-NMR (spectra referenced to hexafluorobenzene, δ 164.9).

(j) Synthesis of Amphoteric Lipid/Ampholip 2

Carboxy-N-palmitoyl-D-erythro-sphingosyl-1-carbamoyl spermine (COOH—CCS) (referred to herein as "Ampholip 2") has the structure:

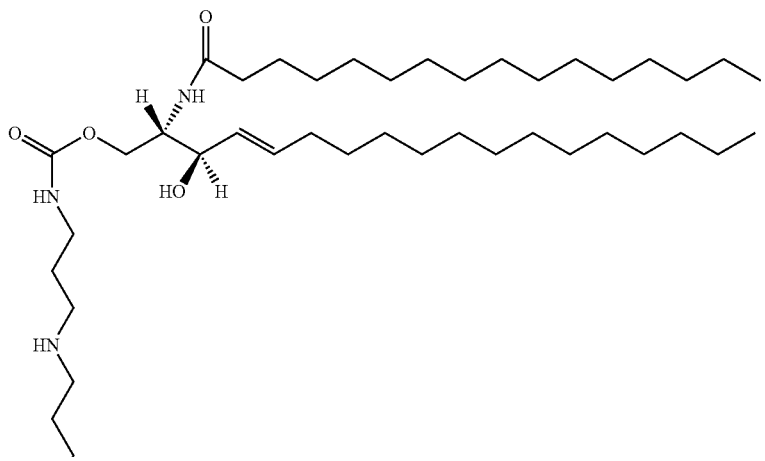

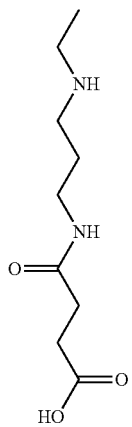

Ampholip 2 was prepared according to the synthetic procedure described below, and the stock was kept as a 1 mM solution in DDW/tert-butanol 1/1.

N-Palmitoylsphingosine (1.61 g, 3 mmol) was dissolved in dry tetrahydrofuran (THF, 100 mL) with heating. The clear solution was brought to room temperature and N,N'-disuccinimidylcarbonate (1.92 g, 7.5 mmol) was added. 4-dimethylamino pyridine (DMAP, 0.81 g, 7.5 mmol) was added with stirring and the reaction further stirred for 16 hours.

The solvent was removed under reduced pressure and the residue re-crystallized for n-heptane yielding 1.3 g (68%) of disuccinimidylceramidyl carbonate as white powder, m.p. 73-76° C. Spermine (0.5 g, 2.5 mmol) and the disuccinimidylceramidyl carbonate (0.39 g, 0.5 mmol) were dissolved in dry dichloromethane with stirring and then treated with a catalytic amount of DMAP.

The solution was stirred at room temperature for 16 hours, the solvent evaporated and the residue treated with water, filtered and dried in vacuum, giving 0.4 g (82%) of crude ceramide-carbamoyl-spermine, which was further purified by column chromatography on silica gel, using 60:20:20 Butanol:AcOH:$H_2O$ eluent. Ceramide-carbamoyl-spermine (0.5 g, 0.65 mmol) was dissolved in dry dichloromethane (7.5 mL) and Succinic anhydride (75 mg, 0.75 mmol) with stirring.

The solution was stirred at room temperature for 16 hours, the solvent evaporated and the residue treated with water, filtered and dried in vacuum, giving 0.3 g (53%) of crude Ampholip 2 which was further purified by column chromatography on silica gel, using 80:10:10 Butanol:AcOH:$H_2O$ eluent.

Liposome Formulations with Oligonucleotides
Lipids for Liposome Formulations
1. Ampholip 1:

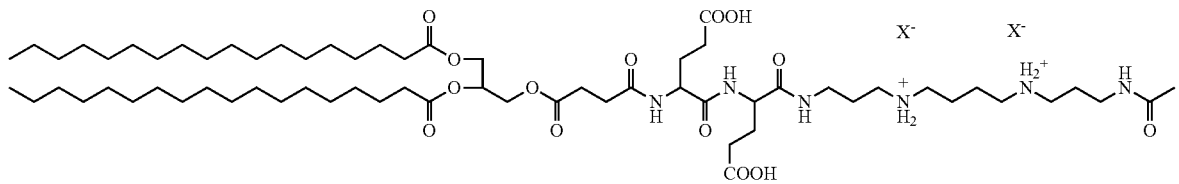

X: $CF_3COO^-$, $CH_3COO^-$ or $Cl^-$

2. Ampholip 2:

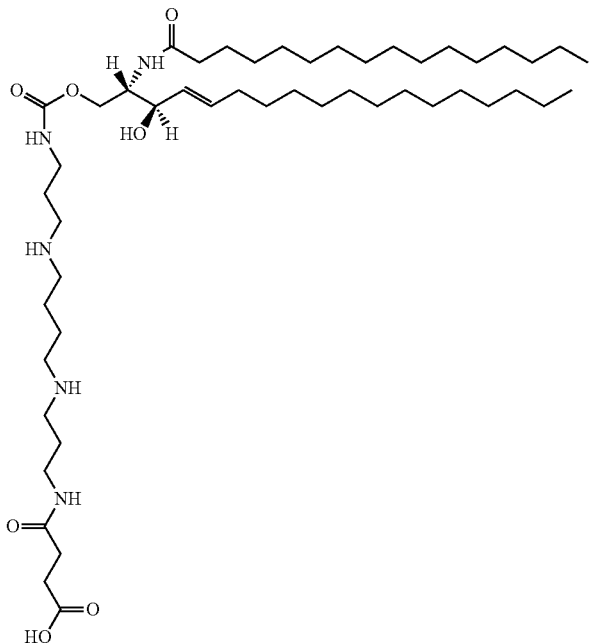 [SMILES: CCCCCCCCCCCCC/C=C/[C@@H](O)[C@H](COC(=O)NCCCNCCCCNCCCNC(=O)CCC(=O)O)NC(=O)CCCCCCCCCCCCCCC]

3. 1,2-dioleoyl-sn-glycero-3-phosphocholine (DOPC) (obtained from Lipoid GmbH, Germany); having the structure:

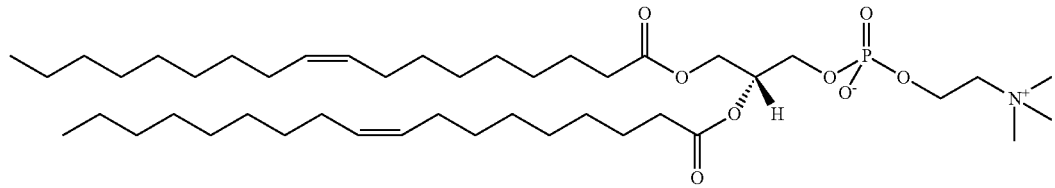 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]

DOPC was prepared as a stock at 10 mg/mL in tert-butanol (J. T. Backer, #8019).
4. PEG-DSPE (obtained from LIPOID GMBH, Germany).
5. Folate-PEG-DSPE (obtained from Avanti Polar Lipids, AL, USA, Catalog No. 880124P) was used as a targeting agent.
6. Cationic lipid: N-Palmitoyl Ceramide di (Carbamoyl-Spermine) (PCDCS) (obtained from Bio-Lab, Israel).

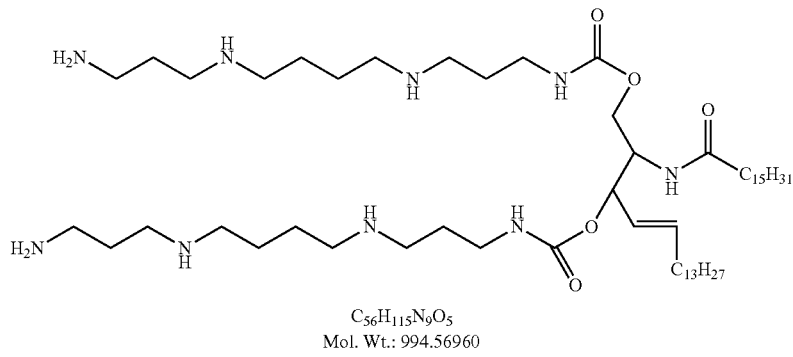

A $C_{56}H_{115}N_9O_5$
Mol. Wt.: 994.56960

7. Tween 20 (obtained from Sigma, MO, USA) was prepared as a stock of 10% in water.

Nucleic Acids for Liposome Formulations

Small RNA molecules were used either naked (non-conjugated) or conjugated to a lipid, and are described below.

microRNAs

It is to be emphasized that the microRNAs disclosed herein are used as examples and should not, in any way, be construed as limiting the scope of the present invention. Detailed sequences of examples of miRs and miR targets and modifications are disclosed in Sequence Table 20A.

1. hsa-miR-34a naked ("miR-34a") was synthesized in the laboratory of Prof. Eylon Yavin (Hebrew University of Jerusalem, Israel).

RNA was synthesized on an automated oligonucleotide synthesizer (ÄKTA Oligopilot 10 synthesizer, GE Healthcare) on a 20 μmol scale using standard conditions.

2. hsa-miR-34a conjugated to sphingolipid ("miR-34a-SL")—see protocol for PLK1 siRNA-SL below.

siRNAs

The siRNA oligonucleotides in the Examples herein below were exemplified by siRNA targeting PLK1, RAC1 and EGFP mRNA. Structural details of the compounds used are summarized herein (Sequence Table 20B). It is to be emphasized that these compounds (sequences and modifications) are used herein as examples and should not, in any way, be construed as limiting the scope of the present invention.

3. PLK1_28_S2054 ("PLK1 siRNA"), RAC1_28_S1908 ("RAC1 siRNA"), and EGFP_1_S500 ("EGFP siRNA") siRNA naked were synthesized on an automated oligonucleotide synthesizer (ÄKTA Oligopilot 10 synthesizer, GE Healthcare) on a 20 μmol scale using standard conditions. Detailed sequences and modifications are disclosed in Sequence Table 20B.

4. PLK1_28_52272 siRNA conjugated to sphinoglipid ("PLK1 siRNA-SL"), and RAC1_28_52045 siRNA conjugated to sphingolipid ("RAC1 siRNA-SL") were synthesized as similar to non-conjugated siRNA up to last position of the strand. The sphingolipid-polyalkylamine phosphoramidites were incorporated into oligonucleotides by coupling to the oligonucleotide strand during synthesis, in particular into antisense strands and/or sense strands useful in generating antisense oligonucleotide compounds or double-stranded RNA nucleic acid molecules, including siRNA, siNA, anti-miR and miRNA. For large scale synthesis (20 μmol), sphingolipid-polyalkylamine phosphoramidite (300 mg) was dissolved in acetonitrile (1.65 mL, 0.15M). Sphingolipid-polyalkylamine was coupled twice (coupling time was 10 minutes for each coupling step). Cleavage and de-protection of siRNA-sphingolipid-polyalkylamine for an oligonucleotide strand (e.g. siRNA strand) bound to resin (344 mg), NH$_4$OH (33% in water): Methylamine (33% in EtOH) were added (v/v; total 3.44 mL) in a sealed tube and incubated for 3.5 h at 65° C. in a heat block. After 3.5 h the tube was cooled to ambient temperature and the resin was spun down in a centrifuge at 4000 rpm for 5 minutes. The supernatant was decanted to a fresh tube and washed twice with EtOH:H$_2$O (2×3.5 mL). The supernatants were combined and dried by lyophilizer. After the oligonucleotide was dried, 0.344 mL DMSO and 3.44 mL TEA 3HF (triethylamine trihydrofluoride) were added in a sealed tube and incubated for 3 h at 65° C. in a heat block. After this incubation, the oligonucleotide was cooled to ambient temperature and further cooled to −20° C. The oligonucleotide was then precipitated with pre-cooled BuOH. siRNA-sphingolipid-polyalkylamine was purified by HPLC due to two peaks obtained. Peak 1 is the desired siRNA conjugated to sphingolipid.

5. RAC1_28_52404 siRNA conjugated to cholesterol ("RAC1 siRNA-Chol")

RNA was synthesized on an automated oligonucleotide synthesizer (ÄKTA Oligopilot 10 synthesizer, GE Healthcare) on a 20 μmol scale using standard conditions. For 3'-end cholesterol conjugations, commercially available 3'-TEG (triethyleneglycol) cholesteryl phophoramidite (Chemgenes, USA) was used as received and coupled using standard conditions. The 3'phosphate polymeric support (GE healthcare, USA) was used for all 3'-end conjugations. Similarly for 5'-end cholesterol conjugation, the commercially available 5'-TEG cholesteryl phophoramidite or C6-cholesteryl phophoramidite (Chemgenes, USA) was used as received and coupled (using standard conditions) to the solid support after RNA synthesis was completed. For 5'-end cholesterol coupling either 3'phosphate polymeric support (GE healthcare, USA) or universal support (GE healthcare, USA), were used.

Preparation of Liposomal Formulations

General Procedure A: Loading of Nucleic Acids by Rehydration

A mixture of liposome-forming components DOPC/Ampholip (1 or 2) 100/10 or DOPC/Ampholip/Folate PEG-DSPE 100/10/1 mole ratio, and Tween 20 (1 mol %) was frozen in liquid nitrogen and lyophilized. The dry powder was then hydrate with 50-100 μl citrate buffer pH 4.3. The conjugated or non-conjugated nucleic acid was added (1 mol %), in the hydration step and then frozen in liquid nitrogen, followed by thawing in 40° C. The freeze-thawing cycles were repeated 4-6 times. The liposomes were diluted to the desired nucleic concentration with histidine/saline buffer pH 6.5. For the in vivo experiments, where liposomes were injected IV, the liposomes were further extruded with 200 nm and 80 nm filters for 4-6 cycles.

Unless indicated differently, the ratio of the liposome components were:
DOPC/Ampholip (1 or 2)/small RNA 100/10/1 mole ratio
DOPC/Ampholip (1 or 2)/Folate PEG-DSPE/small RNA 100/10/1/1 mole ratio.

As referred to herein, the term "formulated" followed by siRNA (any form, or any example thereof) or miRNA (any form or any example thereof), refers to the small RNA in formulation with any one of the lipid combinations: DOPC, DOPC/Ampholip 1 or 2, DOPC/Folate, DOPC/Ampholip 1 or 2/Folate, and any other permutation of the amphoteric liposomes as described herein.

General Procedure for Determining Loading Efficiency of Nucleic Acid into Liposomes:

Samples of nucleic acid such as siRNA loaded on DOPC/Ampholip liposomes were analyzed by gel electrophoresis together with free nucleic acid (e.g. free siRNA). Gel was stained with SYBR green and fluorescence images were taken and level of fluorescence was quantified using LAS3000. Specifically, siRNA molecules were electrophoresed for 15 minutes and then gel was stained with SYBR green for 30 minutes. The migrating siRNA molecules were visualized on LAS3000 instrument and then calculated using Tina 2.0 software.

The calculation $$x = \frac{A-B}{A} * 100\%$$

where x is percent of siRNA loading, A is fluorescent signal of appropriate amount of free siRNA and B is fluorescent signal of unbound siRNA fraction of the same amount of siRNA. X was calculated and presented on a graph.

II. Toxicity (Safety) of Amphoteric Liposomes

Liposomes were prepared as described above, and their size, zeta potential, and in vitro and in vivo safety (toxicity) evaluated.

II. 1 Safety of DOPC/Ampholip1 or DOPC/Ampholip2 loaded with either naked RAC1 or EGFP siRNA Safety (toxicity) of DOPC/Ampholip1 or DOPC/Ampholip2 loaded with either naked RAC1 or EGFP siRNA was evaluated. Both lipid formulations were found safe as described below.

DOPC/Ampholip1+RAC1 siRNA Preparation:

4.6 mg of RAC1 siRNA were mixed with 46 mg DOPC, 4.6 mg of Ampholip1 and 2.66 mg of Tween 20 in 40% tert-Butanol solution in Phosphate-Citrate buffer, pH4, frozen in liquid nitrogen and stored in −70° C. The mix was then lyophilized and hydrated with sterile Saline, dialyzed against 1000 fold volume of saline in regenerated cellulose tubular membrane and then extruded subsequently through 200 nm and 50 nm membranes in a manual extruder (Avanti Polar Lipids, Alabaster USA). Particle size and zeta potential were measured with an automated particle size measurement device (Malvern Zetasizer, UK), using Zetasizer software. The obtained loaded liposomes were then tested for toxicity.

DOPC/Ampholip1+EGFP siRNA Preparation:

1.27 mg of GFP siRNA or miR-34a were mixed with 12.7 mg DOPC, 1.27 mg of Ampholip1 and 740 μg of Tween 20 in 40% tert-Butanol solution in phosphate-citrate buffer pH4, frozen in liquid nitrogen and stored at −70° C. The mixture was then lyophilized and hydrated with sterile saline, dialyzed against 1000 fold volume of saline in regenerated cellulose tubular membrane, and then extruded subsequently through 200 nm and 50 nm membranes with a manual extruder (Avanti Polar Lipids). Particle size and zeta potential were measured with an automated particle size measurement device (Malvern Zetasizer, UK), using Zetasizer software. The obtained loaded liposomes were then tested for toxicity.

DOPC/Ampholip2+RAC1 siRNA Preparation:

12.7 mg DOPC were mixed with 1.46 mg of Ampholip2 and 740 μg of Tween 20 in 40% tert-Butanol solution in DDW, frozen in liquid nitrogen and stored in −70° C. The mix was then lyophilized and hydrated with 1.27 mg of RAC1 siRNA in sterile Saline, dialyzed against 1000 fold volume of saline in regenerated cellulose tubular membrane and then extruded subsequently through 200 nm and 80 nm membranes in a manual extruder (Avanti Polar Lipids, Alabaster USA). Particle size and zeta potential were measured with an automated particle size measurement device (Malvern Zetasizer, United Kingdom), using Zetasizer software. The obtained loaded liposomes were then tested for toxicity and performance in CARPA assay.

DOPC/10% Ampholip1 and DOPC/10% Ampholip2+RAC1 siRNA Preparation:

46 mg DOPC were mixed with 3.2 mg of Ampholip1 or 5.3 mg of Ampholip2 and 2.66 mg of Tween 20 in 40% tert-Butanol solution in DDW, frozen in liquid nitrogen and stored in −70° C. The mix was then lyophilized and hydrated with 4.6 mg of RAC1 siRNA in sterile Saline, dialyzed against 1000 fold volume of saline in regenerated cellulose tubular membrane and then extruded subsequently through 200 nm and 80 nm membranes in an extruder (Lipex Biomembranes, Vancouver, Canada). Particle size and zeta potential were measured with an automated particle size measurement device (Malvern Zetasizer, United Kingdom), using Zetasizer software.

Innate Immune Activation

For evaluating innate immune activation, cytokine induction and interferon (IFN)-responsive gene activation in PBMC (peripheral blood mononuclear cells) were examined following incubation of the formulated siRNA in 200 and 20 nM final concentration of RAC1 siRNA. After 24±2 hours of incubation period, PBMC cells or supernatant were collected for quantification of IFN-responsive genes expression or for IL-6 and TNF-α secreted cytokines, accordingly. IL-6 and TNF-α cytokine levels were determined using a commercial kit (Human DuoSet ELISA kit, R&D Systems), according to the manufacturer's instructions. The results indicate that although the positive control treatment (LPS or CL075) induced high and significant IL-6 and TNFα secretion, no induction of IL-6 or TNFα cytokine secretion was observed in any of the formulated siRNA samples (data not shown). RNA was extracted from the cells in order to evaluate mRNA levels of human genes IFIT1, MX1, OAS1, and ISG15 by qPCR. No significant elevation of any of the examined mRNAs was found in cells treated with the formulated siRNA, while an increase in the expression levels of the genes tested was found after treatment with the positive control CL075 (data not shown).

Complement Activation

For evaluating possible toxicity of the formulated RAC1 siRNA compounds through the induction of the complement activation cascade, human plasma was examined using an enzyme immunoassay for the quantification of the complement terminal SC5b-9 complex. The level of SC5b-9 following 1 hour incubation with formulated siRNA was determined using a commercial SC5b-9 ELISA kit according to the manufacturer's instructions. No induction of SC5b9 could be observed in any of the siRNA-treated cells (data not shown).

In Vivo Toxicity

The potential toxicity of the formulated siRNA was assessed in vivo following a single intravenous (IV) administration of escalating dose levels of Ampholip1 (up to 10 mg/kg) or Ampholip2 (up to 5 mg/kg) in BALB/c mice. Each group comprised six (6) males and six (6) females BALB/cOlaHsd mice, where half of each group (3 males and 3 females) were assigned to 24 hours or 7 days termination time points, respectively. Animals were subjected to clinical hematology and biochemistry assessment at 24 hours and 7 days post dosing, followed by gross macroscopic examination. The following parameters were evaluated for toxicity: mortality, clinical signs, body weight, weight gain, hematology and biochemistry tests. No significant statistical difference was found between the formulated siRNA-treated and the saline-treated groups for all the parameters tested. Similarly, no gross pathological findings were noted in any of the animals at each termination time point.

III. In Vitro Experiments

The section below presents the results of assays for determining the in vitro activity of amphoteric liposomes containing siRNA or miRNA conjugated to sphingolipid (SL), siRNA conjugated to cholesterol (Chol), and siRNA/miRNA naked (non-conjugated).

III. 1 In Vitro Activity of DOPC/Ampholip/siRNA Formulations

III. 1.1 Preparation of Formulations with siRNA-SL Used for In Vitro Assays

The following solutions were used:

1—siRNA conjugate, 5 mg/mL water
2—DOPC, 10 mg/mL tert-Butanol
3—Ampholip 1, 1 mM in t-Butanol/water 1/1
4—Tween 20, 10% in water (130 μg)

The mixture of the components was frozen in liquid nitrogen and lyophilized. The dry powder was hydrated with 100 μl PBS (all the samples included 100 μM siRNA, except the control samples). 80 μl of liposome was analyzed for the in vitro study, and 20 μl was used for analytical measurements. In samples 9* and 19* (Tables 1 and 2, respectively), the siRNA was added at the hydration step.

TABLE 1

PLK1siRNA-SL DOPC/Ampholip1 formulations

| Sample number | PLK1 siRNA-SL (nmoles) | DOPC (nmoles) | Ampholip1 (nmoles) | Tween 20 (μg) |
|---|---|---|---|---|
| 1 | 10 | 200 | 0 | 130 |
| 2 | 10 | 400 | 0 | 130 |
| 3 | 10 | 1000 | 0 | 130 |
| 4 control1 | 0 | 1000 | 0 | 130 |
| 5 | 10 | 200 | 20 | 130 |
| 6 | 10 | 400 | 40 | 130 |
| 7 | 10 | 1000 | 100 | 130 |
| 8 control2 | 0 | 1000 | 100 | 130 |
| 9* | 10 | 1000 | 100 | 130 |

*The si-RNA was added in the hydration step

TABLE 2

RAC1 siRNA -Chol DOPC/Ampholip1 formulations

| Sample number | RAC1-siRNA-Chol (nmoles) | DOPC (nmoles) | Ampholip1 (nmoles) | Tween 20 (μg) |
|---|---|---|---|---|
| 11 | 10 | 200 | 0 | 130 |
| 12 | 10 | 400 | 0 | 130 |
| 13 | 10 | 1000 | 0 | 130 |
| 14 control1 | 0 | 1000 | 0 | 130 |
| 15 | 10 | 200 | 20 | 130 |
| 16 | 10 | 400 | 40 | 130 |
| 17 | 10 | 1000 | 100 | 130 |
| 18 control2 | 0 | 1000 | 100 | 130 |
| 19* | 10 | 1000 | 100 | 130 |

The si-RNA was added in the hydration step

III.1.2 Characterization of DOPC/Ampholip/siRNA Formulations—Zeta Potential

Figure 1B:
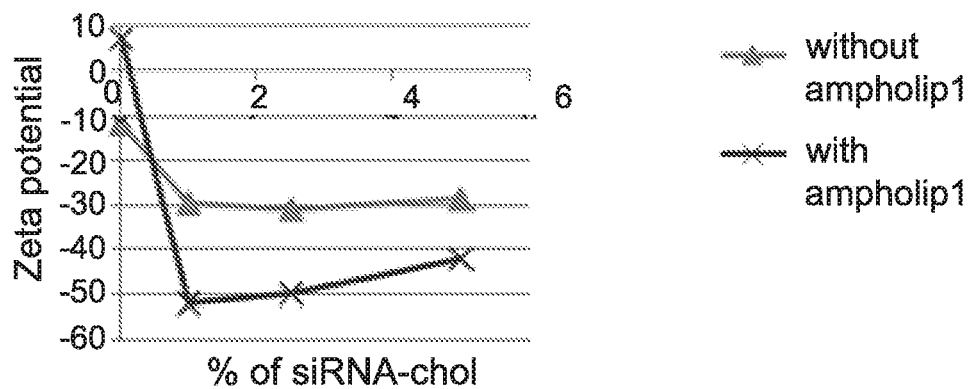

The analysis of zeta potential in DOPC/10% Ampholip formulations loaded with different concentrations of PLK1 siRNA-SL or RAC1 siRNA-Chol is shown in FIGS. 1A and 1B, respectively.

The results show in FIGS. 1A and 1B demonstrate that the presence of Ampholip1 in the formulation decreases the zeta potential, which means that there is an increase of formulation into the liposome surface. This effect was larger for RAC1 siRNA-Chol No. 9 Zeta=−35.3; No. 19. Zeta=−55, FIG. 1B) than for PLK1 siRNA-SL (FIG. 1A).

III.1.3 Characterization of DOPC/Ampholip1/siRNA Formulations—Size Distribution

Tables 3A-3B below show the size distribution of samples of siRNA-SL and siRNA-chol without Ampholip (Table 3A), or siRNA-SL and siRNA-chol with Ampholip1 (Table 3B).

TABLE 3A

Formulations without Ampholip 1

| % siRNA-SL | 200 nm (%) | 1000 nm (%) | 4000 nm (%) | % siRNA-chol | 200 nm (%) | 1000 nm (%) | 4000 nm (%) |
|---|---|---|---|---|---|---|---|
| 5 | 98 | | 2 | 5 | 96 | | 4 |
| 2.5 | 20 | 60 | 20 | 2.5 | 15 | 80 | 5 |
| 1 | 10 | 60 | 30 | 1 | 15 | 75 | 15 |
| 0 | 15 | 55 | 30 | 0 | 20 | 60 | 20 |

TABLE 3B

Formulations with Ampholip1

| % siRNA-SL | 200 nm (%) | 1000 nm (%) | 4000 nm (%) | % siRNA-chol | 200 nm (%) | 1000 nm (%) | 4000 nm (%) |
|---|---|---|---|---|---|---|---|
| 5 | 70 | 20 | 10 | 5 | 90 | | 10 |
| 2.5 | 25 | 65 | 10 | 2.5 | 20 | 75 | 5 |
| 1 | 15 | 80 | 5 | 1 | 20 | 65 | 15 |
| 0 | 30 | 50 | 20 | 0 | 15 | 85 | |

III.1.4 In Vitro Activity of DOPC/Ampholip1/siRNA Formulations (PLK1 siRNA-SL or RAC1 siRNA-Chol)

In vitro knockdown activity of a target gene by formulated PLK1-SL or RAC1-chol siRNA was analyzed using the psiCHECK™ system. The psiCHECK™ expression system (Promega) enables the evaluation of the intrinsic potency of inhibitory oligonucleotides, e.g. siRNA or antisense, by monitoring the changes in the activity of the luciferase reporter gene carrying the target sites for inhibitory oligonucleotide action in its 3' untranslated region (3'-UTR). The activity of a siRNA toward this target sequence usually results either in cleavage and subsequent degradation of the cleaved mRNA or translation inhibition of the protein encoded by the target gene. In addition, the psiCHECK™-2 vector contains a second reporter gene, Firefly luciferase, transcribed from a different promoter and unaffected by the inhibitory oligonucleotide under study. This allows for normalization of Renilla luciferase expression across different transfections.

psiCHECK™-2-based construct was prepared for the evaluation of the on-target activity of the guide strands (GS, antisense) of PLK1/RAC1 siRNAs, the off target activity of the guide strand seed sequence (GS-SM) and/or the target activity of the passenger strand (PS-CM, also referred to as off target activity of an siRNA). In the construct, one copy of the full target sequence of the test molecule GS was cloned into the multiple cloning site located in the 3'-UTR of the Renilla luciferase, downstream to the stop codon. The psiCHECK™-2 plasmid was transfected into human HeLa cells. The transfected HeLa cells were then seeded into the wells of a 96-well plate and incubated at 37° C. with the siRNA of interest added in duplicates without transfection reagent.

The formulations bearing PLK1/RAC1 siRNA tested are described in Tables 1 and 2 above. Control cells were not exposed to any siRNA, and were treated with controls 4 and 14 (see Tables 1 and 2). Forty-eight (48) hours following siRNA transfection, the cells were harvested for protein extraction. Renilla and firefly luciferase activities were measured in individual cell protein extracts using a commercial luciferase assay kit (Dual-Luciferase® Assay kit, Promega) according to the manufacturer's instructions. Renilla luciferase activity values were normalized by Firefly luciferase activity values obtained from the same samples. siRNA activity was expressed as percentage of residual normalized Renilla luciferase activity in a test sample from the normalized Renilla luciferase activity in negative control cells. The study was repeated at least twice and representative results are shown in Table 4 below.

TABLE 4

Results of in vitro activity of DOPC/Ampholip1/siRNA formulations

| Sample description | Sample | siRNA concentration | | | |
| --- | --- | --- | --- | --- | --- |
| | | 1.6 µM | 0.56 µM | 0.185 µM | 0.062 µM |
| DOPC/PLK siRNA-SL | 1 | 55 | 59 | 69 | 71 |
| DOPC/PLK siRNA-SL | 2 | 38* | 56 | 75 | 65 |
| DOPC/PLK siRNA-SL | 3 | 46* | 53 | 58 | 76 |
| DOPC/Ampholip1/PLK siRNA-SL | 5 | 32* | 37* | 51 | 59 |
| DOPC/Ampholip1/PLK siRNA-SL | 6 | 32* | *45 | 62 | 59 |
| DOPC/Ampholip1/PLK siRNA-SL | 7 | 50 | 56 | 62 | 53 |
| Control-DOPC/Ampholip1 | 8 cont | 62 | 74 | 75 | 75 |
| DOPC/Ampholip1/PLK siRNA-SL | 9* | 38* | 40* | 43* | 49* |
| DOPC/RAC1 siRNA-Chol | 11 | 54 | 66 | 74 | 90 |
| DOPC/RAC1 siRNA-Chol | 12 | 59 | 67 | 72 | 84 |
| DOPC/RAC1siRNA-Chol | 13 | 44* | 52 | 62 | 75 |
| DOPC/Ampholip1/RAC1siRNA-Chol | 15 | 51 | 65 | 74 | 84 |
| DOPC/Ampholip1/RAC1siRNA-Chol | 16 | 53 | 61 | 75 | 75 |
| DOPC/Ampholip1/RAC1siRNA-Chol | 17 | 50 | 54 | 59 | 63 |
| DOPC/Ampholip1/RAC1siRNA-Chol | 18 cont | 68 | 70 | 69 | 64 |
| DOPC/Ampholip1/RAC1siRNA-Chol | 19* | 42 | 50 | 52 | 60 |
| Control-DOPC | 4 + 14 average | 56 | 56 | 59 | 51 |

*residual mRNA below 50%

The results presented in Table 4 show that siRNA activity was detected in all tested formulations at 5 µM as compared to siRNA depleted formulation (samples 4+14 and 18).

III. 2 In Vitro Activity of DOPC/Ampholip1/PEG-Folate/siRNA Formulations

III.2.1 Preparation of the DOPC/Ampholip1/PEG-Folate/siRNA Formulations Used for In Vitro Activity Assays The DOPC/Ampholip1/PEG-Folate/siRNA formulations were prepared using the following solutions:
1—siRNA 5 mg/mL water
2—DOPC 10 mg/mL tert-Butanol
3—Ampholip1 1 mM in t-Butanol/water 1/1
4—Tween 20 10% in water
5—PEG-folate 5 mg/mL tert-Butanol The mixture was frozen in liquid nitrogen and then lyophilized. Samples were subjected to four (4) freeze-thaw cycles in acidic conditions (buffer citrate pH 4.3) with siRNA (25 µL), followed by hydration with 75 µl PBS.

Table 5 below provides a summary of the DOPC/Ampholip1/PEG-folate formulations tested for in vitro activity.

TABLE 5

DOPC/Ampholip1/Folate Formulations

| Sample | Sample Description | DOPC nmole | Tween (130 µg) | Ampholip1 (nmole) | Folate-PEG-DSPE nmole | siRNA (PLK1) - SL nmole | siRNA (RAC1) nmole | siRNA (RAC1) - CHOL |
|---|---|---|---|---|---|---|---|---|
| 1 control | Control-DOPC/Ampholip1 | 1000 | + | 100 | — | — | — | — |
| 2 | DOPC/Ampholip1/PLK siRNA-SL | 1000 | + | 100 | — | 10 | — | — |
| 3 | DOPC/PLK siRNA-SL | 1000 | + | — | — | 10 | — | — |
| 4 control | Control DOPC/Ampholip1/Folate | 1000 | + | 100 | 10 | — | — | — |
| 5 | DOPC/Ampholip1/Folate/PLK siRNA-SL | 1000 | + | 100 | 10 | 10 | — | — |
| 6 | DOPC/Ampholip1/Folate/RAC1 siRNA | 1000 | + | 100 | 10 | — | 10 | — |
| 7 | DOPC/Ampholip1/Folate/RAC1 siRNA-Chol | 1000 | + | 100 | 10 | — | — | 10 |
| 8 | DOPC/Ampholip1/Folate | 1000 | + | — | 10 | — | — | — |
| 9 | DOPC/Folate/PLK siRNA-SL | 1000 | + | — | 10 | 10 | — | — |
| 10 | DOPC/Folate/siRNA RAC1 | 1000 | + | — | 10 | — | 10 | — |
| 11 | DOPC/Folate/RAC1 siRNA-Chol | 1000 | + | — | 10 | — | — | 10 |

III.2.2 Characterization of the DOPC/Ampholip1/PEG-Folate/siRNA Formulations Used for In Vitro Activity—Zeta Potential Characterization of the liposomes showed that all liposomes with the Ampholip1 were amphoteric, indicated by the zeta potential of ~0.0 mV. Encapsulation of the nucleic acids rendered the liposomes negatively charged, indicating association of siRNA with the liposomal membrane. Chol-siRNA conjugates introduced a larger negative charge than SL-siRNA conjugates. This result suggested a different distribution of the two siRNAs, with larger presence of Chol-siRNA interacting with the outer leaflet of the liposomes than the SL-siRNA.

Table 6 below provides a summary of the zeta potential for the DOPC/Ampholip1/PEG-folate formulations tested for in vitro activity.

III.2.3 Results of the in vitro activity assays with DOPC/Ampholip1/PEG-Folate/siRNA Formulations Table 7 below shows the results of siRNA activity as measured by psi-check in vitro assay of DOPC/Ampholip1/PEG-Folate/siRNA formulations. The results show that encapsulation of none conjugated siRNA with DOPC/Ampholip 1/Folate significantly increase siRNA activity (samples 7 and 14) in a dose response dependent manner. Further, the results show that RAC1 siRNA-Chol activity was improved under DOPC/Folate compared to DOPC/Ampholip1/Folate (samples 12 and 8). High activity was demonstrated by PLK1 siRNA-SL alone or in formulation with DOPC (samples 4 and 13). Addition of folate±Ampholip1 displayed similar activity results (samples 6 and 10).

TABLE 6

Zeta Potential of Ampholip1/PEG-Folate/siRNA-(SL or Chol) Formulations

| Sample | Sample Description | Zeta Potential (mV) |
|---|---|---|
| 1 control | Control-DOPC/Ampholip1 | -4 |
| 2 | DOPC/Ampholip1/PLK siRNA-SL | -30.5 |
| 3 | DOPC/PLK siRNA-SL | -12.5 |
| 4 control | Control DOPC/Ampholip1/Folate | -23.5 |
| 5 | DOPC/Ampholip1/Folate/PLK siRNA-SL | -27.3 |
| 6 | DOPC/Ampholip1/Folate/RAC1 | -26.5 |
| 7 | DOPC/Ampholip1/Folate/RAC1 siRNA-Chol | -38.8 |
| 8 control | DOPC/Ampholip1/Folate | -29.7 |
| 9 | DOPC/Folate/PLK siRNA-SL | -23.2 |
| 10 | DOPC/Folate/RAC1 siRNA | -23.5 |
| 11 | DOPC/Folate/RAC1 siRNA-Chol | -25 |

TABLE 7

Results of in vitro assay

| | | psiCHECK Results siRNA concentration | | | |
|---|---|---|---|---|---|
| Samples description | Sample | 3 µM | 1 µM | 0.3 µM | 0.03 µM |
| Control - DOPC/Ampholip1 | 1 cont | 69 | 80 | 83 | 79 |
| DOPC/Ampholip1/PLK siRNA-SL | 2 | 47* | 60 | 59 | 76 |
| DOPC/PLKsiRNA-SL | 3 | 26* | 33* | 48* | 68 |
| Control-DOPC/Ampholip1/Folate | 4 cont | 81 | 84 | 78 | 88 |
| DOPC/Ampholip1/Folate/PLKsiRNA-SL | 5 | 39* | 47* | 55 | 72 |
| DOPC/Ampholip1/Folate/RAC1siRNA | 6 | 39* | 44* | 47* | 74 |
| DOPC/Ampholip1/Folate/RAC1siRNA-Chol | 7 | 39* | 47* | 54 | 68 |
| control-DOPC/Ampholip1/ | 8 | 84 | 74 | 74 | 78 |

TABLE 7-continued

Results of in vitro assay

| | | psiCHECK Results siRNA concentration | | | |
|---|---|---|---|---|---|
| Samples description | Sample | 3 µM | 1 µM | 0.3 µM | 0.03 µM |
| Folate | cont | | | | |
| DOPC/Folate/PLK siRNA-SL | 9 | 38* | 46* | 64 | 92 |
| DOPC/Folate/RAC1 siRNA | 10 | 60 | 72 | 95 | 107 |
| DOPC/Folate/RAC1 siRNA-Chol | 11 | 33* | 37* | 44* | 55 |

*residual mRNA below 50%

III.3 In Vitro Activity of DOPC/Ampholip1 or Ampholip2 Formulations Loaded with miR-34a Naked or miR-34a-SL III.3.1 Preparation of DOPC/Ampholip1/miR-34a Formulations for In Vitro Assays The DOPC/Ampholip1/miRNA-SL formulations were prepared using the following solutions:
1—miR34a-SL or miR-34a 5 mg/mL water
2—DOPC 10 mg/mL tert-Butanol
3—Ampholip1 1 mM in t-Butanol/water 1/1
4—Tween 20 10% in water The mixture of the components was frozen in liquid nitrogen and lyophilized. The lyophilized mixture was hydrated with 100 µl PBS.

Table 8 presents the details of the DOPC/Ampholip1 formulations loaded with miRNAs. All formulations were prepared with 130 µg Tween 20.

TABLE 8

DOPC/Ampholip1/miRNA formulations

| Sample number | miR-34a-SL (nmoles) | DOPC (nmoles) | Ampholip1 (nmoles) |
|---|---|---|---|
| 1 | 10 | 200 | 0 |
| 2 | 10 | 400 | 0 |
| 3 | 10 | 1000 | 0 |
| 4 control1 | 0 | 1000 | 0 |
| 5 | 10 | 200 | 20 |
| 6 | 10 | 400 | 40 |
| 7 | 10 | 1000 | 100 |
| 8 control2 | 0 | 1000 | 100 |

Figure 2:
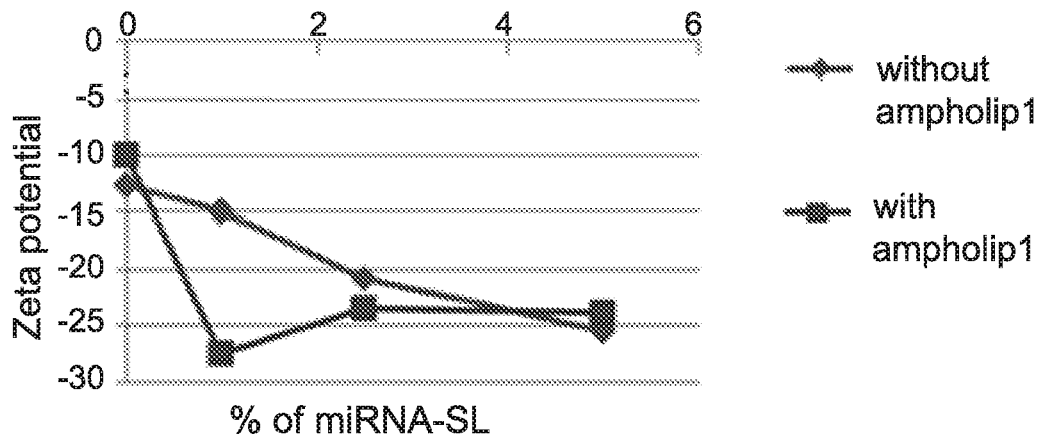
FIG. 2 is a graph showing the zeta potential for the formulations having miRNA-SL in different concentrations, with 10% Ampholip1 (squares) and without (diamonds).

III.3.2 Characterization DOPC/Ampholip1/miRNA-SL Formulations Used for In Vitro Activity Assays—Zeta Potential The analysis of zeta potential for the formulations having miRNA-SL in different concentrations, with 10% Ampholip1 and without is shown in FIG. 2.

III.3.3 Characterization DOPC/Ampholip/miRNA-SL Formulations Used for In Vitro Activity Assays—Particle Size All DOPC/Ampholip1/miRNA-SL formulations presented 80% of 500-1000 nn; 10% of 100-200 nm and 10% of 5000 nm particles.

III.3.4 Formulation Preparation of the In Vitro Activity Assays with DOPC/Ampholip1/PEG-Folate/miR Formulations Initially, a dose response curve of miR-34a-SL or miR-34a naked was done in order to optimize the formulations. Ten (10) formulations with and without 1 mole % PEG-folate were tested, and are presented in Table 9 below. Controls were Ampholip1 only without miRNA (groups 1 and 2), or miRNA without Ampholip1 (group 9, naked miR-34a; group 10 miR-34a-SL).

The formulations were prepared using the following solutions:
1—miR 10 mg/mL water
2—DOPC 10 mg/mL tert-Butanol
3—Ampholip1 1 mM in t-Butanol/water 1/1
4—Tween20 10% in water
5—PEG-folate 5 mg/mL tert-Butanol The mixtures were frozen in liquid nitrogen then lyophilized. Samples 1, 2, 7, 8 were hydrated with 100 µl PBS. Samples 3-6, 9-10 were subjected to four (4) freeze-thaw cycles in acid condition (buffer citrate pH 4.3) with miRNA (25 µL), followed by hydration with 75 µl PBS.

Table 9 shows the zeta potential measured for the DOPC/Ampholip1/PEG-Folate/miR formulations tested in vitro.

TABLE 9

Zeta potential for the formulations used in vitro

| Sample | DOPC nmoles | Ampholip1 nmoles | Tween 20 (µg) | PEG-folate nmoles | miR-34a nmoles | miR-34a-SL nmoles | Zeta Potential |
|---|---|---|---|---|---|---|---|
| 1 control | 1000 | 100 | 130 | 10 | 0 | 0 | −9.6 |
| 2 control | 1000 | 100 | 130 | 0 | 0 | 0 | −16.2 |
| 3 | 1000 | 100 | 130 | 10 | 10 | 0 | −26 |
| 4 | 1000 | 100 | 130 | 0 | 10 | 0 | −27 |
| 5 | 1000 | 100 | 130 | 10 | 0 | 10 | −39 |
| 6 | 1000 | 100 | 130 | 0 | 0 | 10 | −35.5 |
| 7 | 1000 | 100 | 130 | 10 | 0 | 10 (lyo with lipid) | −26.5 |
| 8 | 1000 | 100 | 130 | 0 | 0 | 10 (lyo with lipid) | −25.5 |
| 9 control | | | | | 10 | | |
| 10 control | | | | | | 10 | |

III.3.5 Results of the In Vitro Activity Assays with DOPC/Ampholip1/PEG-Folate/miR Formulations The formulations used in the in vitro assays are described in section 111.3.4. Reverse compliment sequence to miR-34a (22 bp) was inserted into the 3' UTR of *Renilla* luciferase in psiCHECK-2 vector (Promega). To test the formulations, luciferase assay to miR-34a was used in human ovarian cancer cells (SKOV cell line). The cells were transfected in triplicate with the vector or co-transfected with a vector and the miR-34a or miR-34a-SL formulations. Luminescence was assayed 48 hours later using a commercial luciferase assay (Dual-Luciferase Reporter-Assay-System, Promega, Catalogue No. E1961), according to manufacturer's instructions. Results were normalized to the constitutively expressed Firefly luciferase from the same vector, and shown as the ratio between the various treatments and cells transfected with a non-modified vector.

Figure 3:
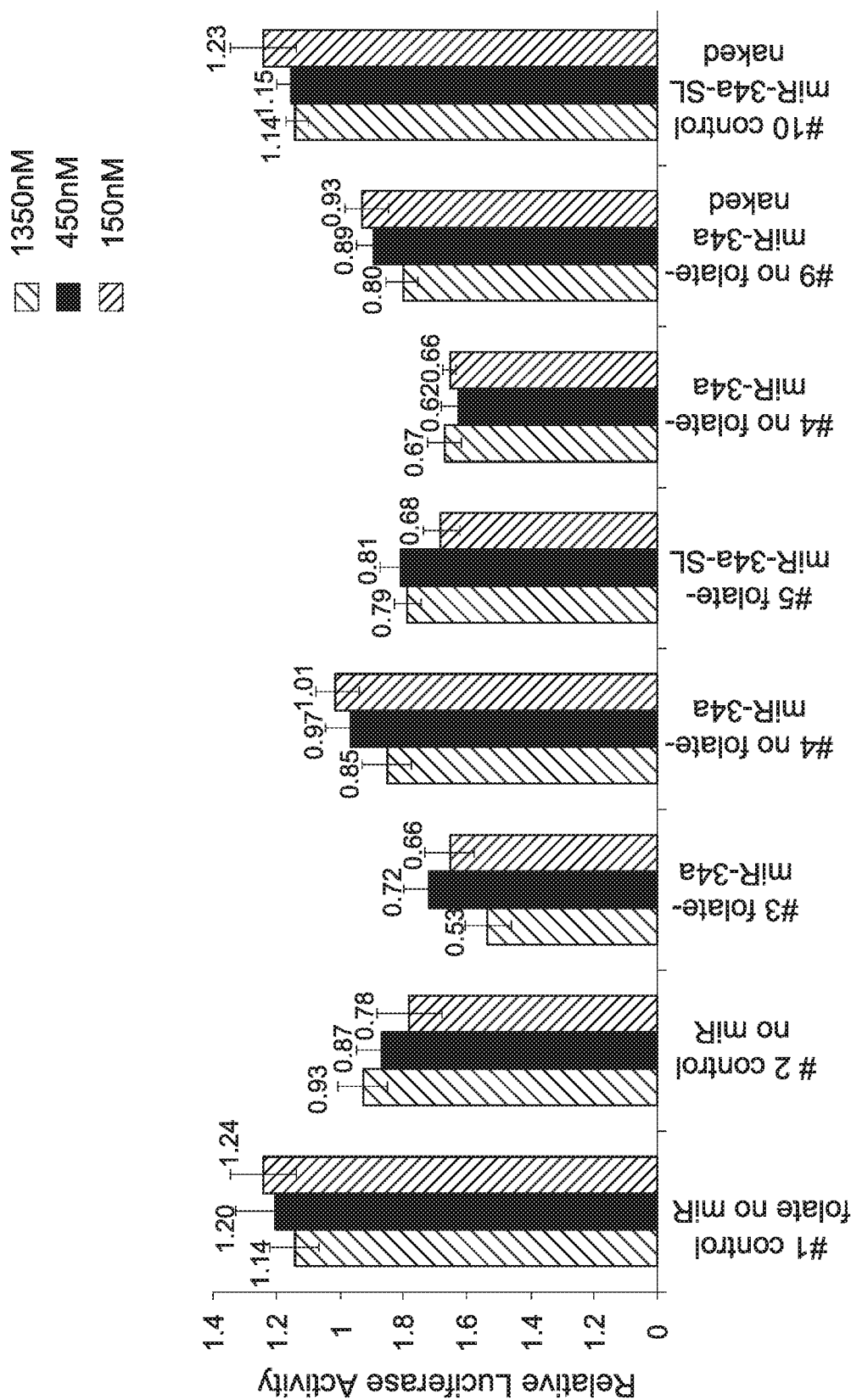
FIG. 3 is a graph showing the results of the in vitro activity assays with DOPC/Ampholip1/PEG-Folate/miR Formulations transfected into human ovarian cancer cells SKOV and measured through luciferase assay. X-axis shows three concentrations (1350 nM, 450 nM and 150 nM) of each formulation transfected; Y-axis shows relative luciferase activity.

The results, shown in FIG. 3, may be summarized as follows. The formulations with the best activity were Formulation 3 (DOPC/Ampholip1/Folate/miR-34a), Formulation 5 (DOPC/Ampholip1/Folate/miR-34a-SL) and Formulation 6 (DOPC/Ampholip1/miR-34a-SL (no folate)). miR-34a naked or miR-34a-SL alone did not show any activity (Formulations 9 and 10).

It may be concluded that miR-34a-SL showed the highest activity, while naked miR-34a in combination with folate showed slightly more reporter inhibition activity.

Figure 4:
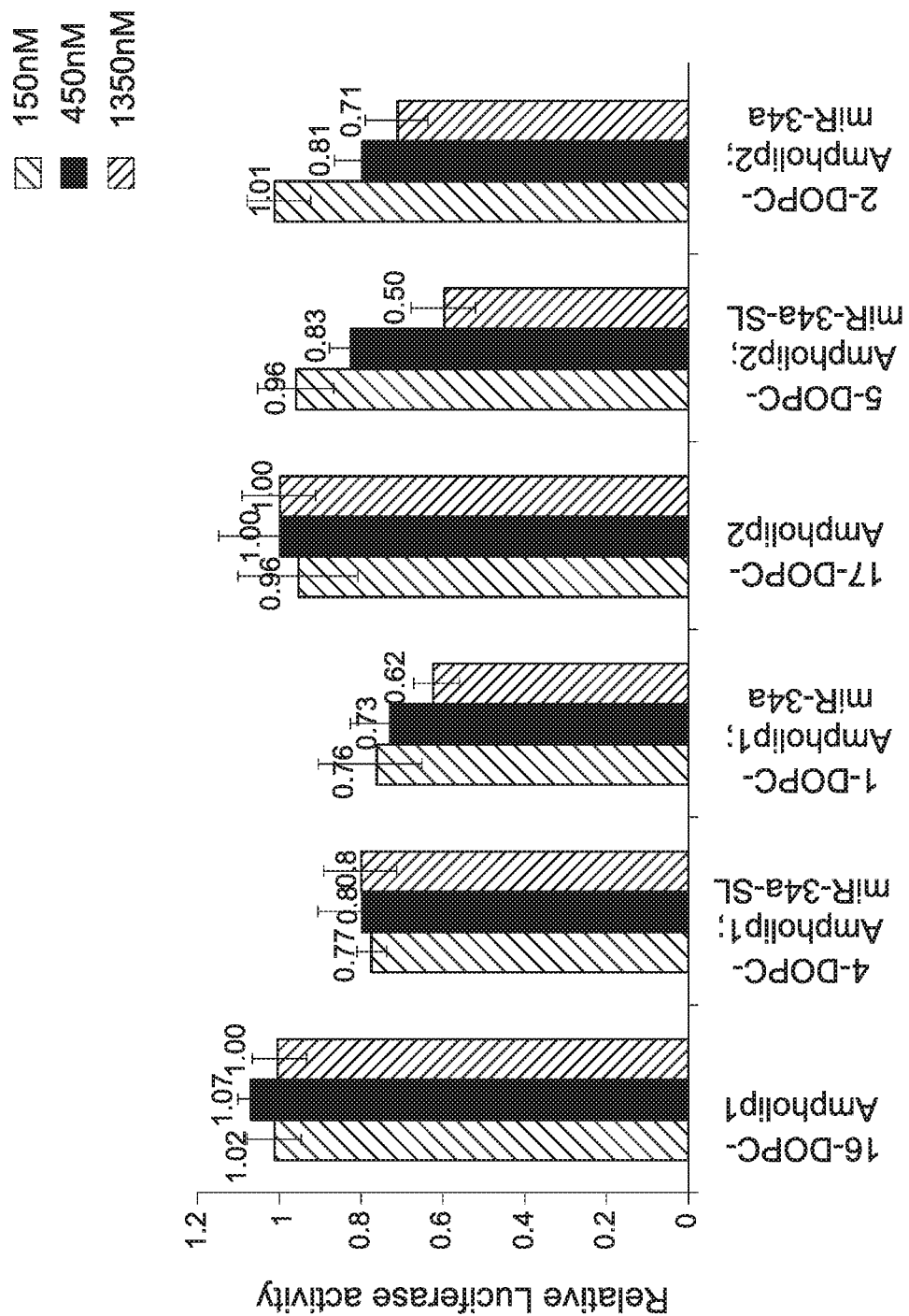
FIG. 4 is a graph showing the results of the in vitro activity assays with Ampholip1 or Ampholip 2/miR Formulations, where the miR is conjugated to SL or not, transfected into SKOV cells and measured through luciferase assay. X-axis shows three concentrations (1350 nM, 450 nM and 150 nM) of each formulation transfected; Y-axis shows relative luciferase activity.

III.3.6 Formulations for In Vitro Activity Assays with DOPC/Ampholip1 or 2/miR The formulations used for the second in vitro assay are presented in Table 10, and the results shown in FIG. 4.

TABLE 10

DOPC/Ampholip1 or 2/miRNA formulations used in the second in vitro assay

| Formulation # | Content | Comments |
|---|---|---|
| 1 | DOPC; Ampholip1; miR-34a | naked miR (no SL) |
| 2 | DOPC; Ampholip2; miR-34a | naked miR (no SL) |
| 3 | DOPC; miR-34a | naked miR (no SL) |
| 4 | DOPC; Ampholip1; miR-34a-SL | SL conjugation |
| 5 | DOPC; Ampholip2; miR-34a-SL | SL conjugation |
| 6 | DOPC; miR-34a-SL | SL conjugation |
| 16 | DOPC; Ampholip1 | Control |
| 17 | DOPC; Ampholip2 | Control |
| 18 | DOPC | Control |

III.3.7 Physical Characterization of the Formulations for In Vitro Activity Assays with DOPC/Ampholip1 or 2/miR Physical characterization by zeta potential and size of the formulations are presented in Tables 11 and 12 below.

TABLE 11

Summary of the Zeta potential measured in miR formulations

| Formulation | Ampholip1 | Ampholip2 | No Ampholip |
|---|---|---|---|
| miR34a- naked | −27.5 | −24 | −18.5 |
| miR-34a-SL | −34.7 | −34 | −15.5 |
| Control | −18.5 | 41 | −12.9 |

TABLE 12

Size distribution for the miR formulations

| Formulation | Ampholip1 | Ampholip2 | No Ampholip |
|---|---|---|---|
| miR34a - naked | 590 nm - 67% | 1000 nm - 60% | 260 nm - 90% |
|  | 130 nm - 30% | 200 nm - 27% | 4000 nm - 10% |
|  | 5500 nm - 3% | 5000 nm - 13% |  |
| miR-34a-SL | 850 nm - 66% | 700 nm - 50% | 330 nm - 98% |
|  | 130 nm - 28% | 150 nm - 40% | 4500 nm - 2% |
|  | 5400 nm - 6% | 5000 nm - 10% |  |
| control | 790 nm - 60% | 200 nm - 60% | 300 nm - 95% |
|  | 160 nm - 35% | 1500 nm - 40% | 4500 nm - 5% |
|  | 450 nm - 0 5% |  |  |

III.3.8 Results of the In Vitro Activity Assays with DOPC/Ampholip1 or 2/miR Formulations All data was normalized to firefly levels (internal control) and then to the expression of the same plasmid without any formulation (negative control=1). The results are shown in FIG. 4 and show that both Ampholip1 and Ampholip2 demonstrated activity with naked miR-34a or miR-34a-SL (Formulations #4, #1, #2 and #5), relative to lipids controls (Formulations #16 and #17).

The results of the in vitro studies led to select the following optimal mole ratio for the formulations:

DOPC (Liposome forming Lipid) Low Tm, soft, 1000
Ampholip1 (amphoteric glycero-lipid), 100
Tween20 (PEG(20) sorbitan monolaurate MW 1227) 10 (1 mol %)
Steric stabilizer and enabler of shape changes
DSPE-PEG-Folate (when added) was 1 mole % (with respect to total lipids in moles)
miRNA added at 1 mole % (with respect to total lipids in moles).

IV. In Vivo Experiments

IV.1 Pharmocokinetcs (PK) Study

The formulations used for the pharmacokinetics (PK) study in mice described further below are described in Table 13, which provides the physico-chemical characterization (size and zeta potential).

TABLE 13A

Physico-chemical characterization of liposomes used in vivo for PK studies

| Liposomal samples have 1.2 mg/3 mL siRNA or miR (composition) | Zeta potential mV | Size (z-ave) nm (% of the population) |
|---|---|---|
| DOPC/Ampholip1/Tween20 + PLK1 siRNA-SL | −41.2 | 103 (100%) |
| DOPC/Ampholip1/Tween20 + miR-34a-SL | −32.0 | 114.5 (98.2%) |
| DOPC/Ampholip1/Folate/Tween20 + miR-34a | −13.0 | 164 (99%) |
| DOPC/Ampholip1/Tween20 + RAC1-28S2404 | −15.5 | 115 (99.2%) |
| control liposome (no small RNA) DOPC/Ampholip1/Tween20 | −1.5 | 190 (100%) |
| control liposome (no small RNA) DOPC/Ampholip1/Folate/Tween20 | 0.5 | 196 (100%) |

TABLE 13B

Physico-chemical characterization of liposomes used in vivo in SKOV cells

| Sample No. | Sample | Ampholip1 | PEG-folate | Zeta (mv) | Size (nm) (% of population) |
|---|---|---|---|---|---|
| 1 | miR | + | + | −13 | 200 (55% >1u 45%) |
| 2 | miR-SL | + | − | −22 | 325 (55% >1u 45%) |
| 4 | siRNA | + | + | −15 | 125 (60% >1u 40%) |
| 5 | siRNA-CHOL | + | − | −48 | 120 (45% >1u 55%) |
| 6 | siRNA-CHOL | + | + | −40 | 150 (40% >1u 60%) |
| 7 | siRNA-CHOL | − | + | −22.5 | 110 (40% >1u 60%) |
| 9 | control | + | + | −13.5 | 330 (90% >1u 10%) |

IV. 2 Pharmacokinetics Study with Formulated siRNA

For the PK study, SUV (small unilamellar vesicles) were used for IV route of administration. The formulations (and the control) tested are presented in Table 14.

TABLE 14

Tested formulations

| Group No. | Tested formulation |
|---|---|
| 1 | Saline/PLK1 siRNA-SL |
| 2 | DOPC/Ampholip1/PLK1 siRNA-SL |
| 3 | Saline/RAC1_28_S2404 |
| 4 | DOPC/Ampholip1/RAC1_28_S2404 |

PLK siRNA-SL formulated with Ampholip1 was further subjected to PK evaluation for assessment of blood stability and circulation time. Rats were injected IV with formulated siRNAs followed by collection of blood samples for siRNA quantification at multiple time points after injection. At study termination (24 hours) liver and kidney tissues were collected. Plasma was separated from the blood samples for siRNA quantification by stem-loop qPCR analysis. The siRNA was extracted from the plasma using Triton X-100 extraction. For determining the RAC1 siRNA levels in the samples cDNA was prepared using the Stem loop method for siRNA detection. qPCR was carried out according to standard protocols. In a slight variation to the protocol the SYBR fast ABI prism Ready mix kit (KAPA cat no. KK-KK4605) was used with an elongation/extension time of 30 secs. 0.4 µl of each primer and 6.2 µl of water was used per sample in the reaction mix.

Figure 5:
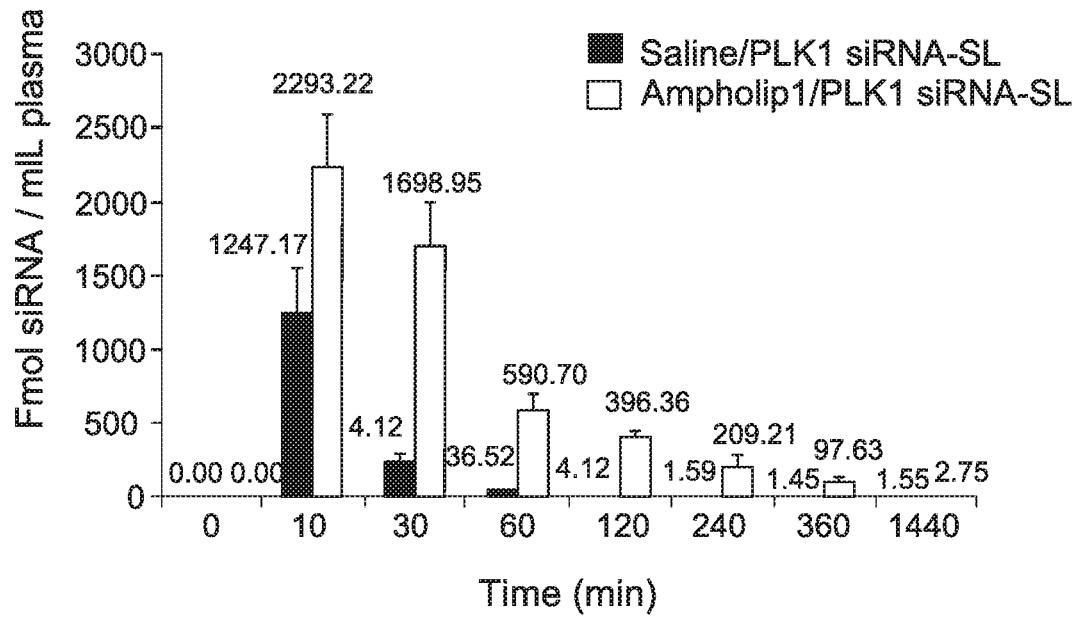
FIG. 5 is a graph showing the results of the PK evaluation of the siRNA formulations. X-axis shows treatment time-points. Y-axis shows the amount of siRNA found in blood as fmol siRNA/μL plasma.

Formulated PLK1 siRNA-SL levels were higher compared to non-formulated siRNA reaching up to ~100 fold higher amount at 4 hours from injection as shown in FIG. 5. In order to elucidate these differences, plasma samples at 10 and 30 min time points from rats injected with formulated and non-formulated SL-Spermine siRNA were analyzed, by northern blot hybridization, for siRNA stability. Migration pattern and band size of hybridized samples were compared to positive control strand of passenger siRNA-SL. Liposomal formulated siRNA migrate as the SL-conjugated passenger while the non-formulated siRNA migration was lower and display similar pattern as the non-conjugated siRNA (data not shown), suggesting the non-formulated siRNA was degraded in plasma while the formulated siRNA was protected.

IV.3 Results of PK Study with Formulated miRNA

The formulations used in the miR-PK study are defined in Table 15. Physical characterization of the formulations as presented in Table 13 above.

TABLE 15

Tested formulations

| Group | Tested formulation |
|---|---|
| 5M | Saline/miR-34a-SL (control) |
| 6M | DOPC/Ampholip1/miR-34a-SL |
| 7M | Saline/miR-34a (control) |
| 8M | DOPC/Ampholip1/Folate/miR-34a |
| 9M | DOPC/Ampholip1 |
| 10M | DOPC/Ampholip1/Folate (control) |

Three animals were injected IV in each group with a dose of 1 mg/kg. Plasma was isolated at serial time points: pre-dosing (time 0), 10 minutes, 30 minutes, 1 hour, 2 hours 4 hours, 6 hours and 24 hours. RNA was extracted from the plasma according to Rosetta Genomics' protocol of miRNA isolation from fluids. qPCR was done for miR-34a, normalized to selected miRNAs: hsa-miR-16-5p, hsa-miR-103a-3p and hsa-miR-23a-3p. The data was analyzed and it is presented in FIG. 6.

Figure 6:
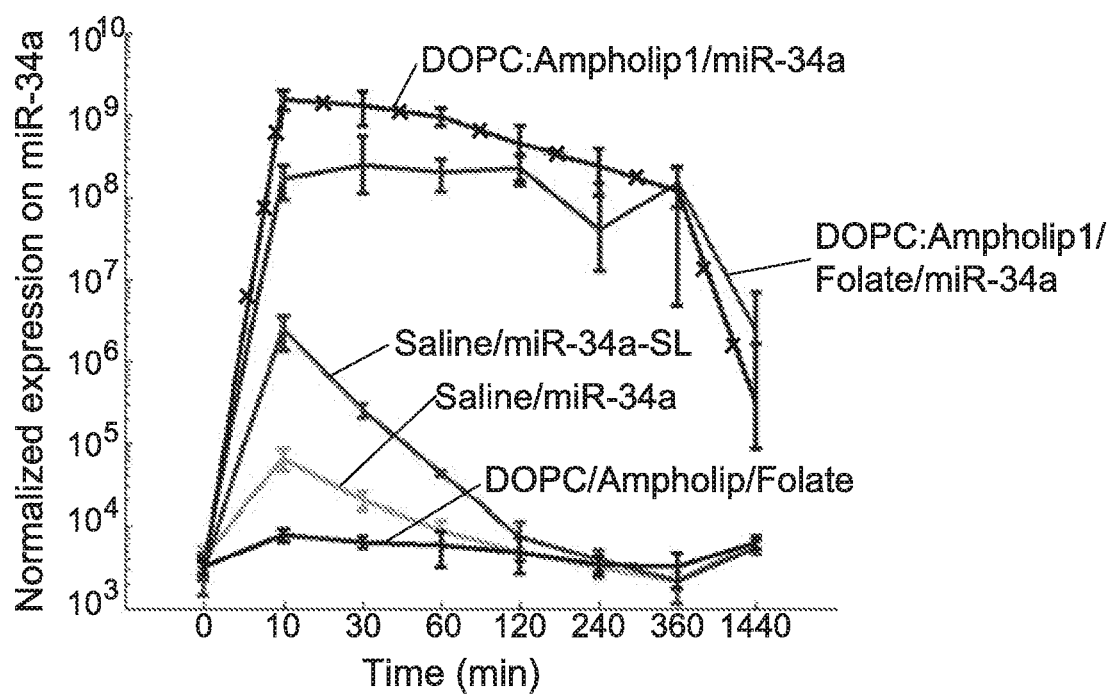
FIG. 6 shows the results of qPCR of miR-34a in the plasma of IV-injected animals, treated with DOPC/Ampholip1/Folate/miR-34a; DOPC/Ampholip1/miR-34a; DOPC/Ampholip1/Folate; Saline/miR-34a; and Saline/miR-34a-SL. Y-axis represents normalized expression in linear scale (2^normalized Ct). X-axis shows the time points.

FIG. 6 shows the results of qPCR of miR-34a in the plasma. The results are shown as normalized expression in linear scale (2^normalized Ct). For the two formulations (1) DOPC/Ampholip1/Folate/miR-34a; and (2) DOPC/Ampholip1/miR-34a-SL, miR-34a in the plasma reached the highest levels after 10 minutes, with a time-dependent reduction, while non-formulated, naked miR-34a was rapidly degraded.

The PK studies lead to the conclusion that the amphotheric formulations in combination with sphingolipids significantly improve plasma stability and bioavailability relative to non-formulated miRNA, demonstrating the best effect compared to other formulations tested. The data also show an estimate of 57% encapsulation for miR-34a. At 30 minutes, 71% of miR-34a-SL was in lipid formulation in circulation (relative to 10 minutes), while miR-34a-SL non-formulated (SL) 14% at 30 min in circulation (relative to 10 minutes) [71%-14%=57%].

IV. 4 In Vivo SKOV Model

IV.4.1 In vivo Activity of miRNA (Ampholip 1)

In vivo bio-distribution and activity of miR-34a or siRNA formulated with DOPC/Ampholip was evaluated in female nude mice bearing orthotopic intraperitoneal tumors of SKOV-3 human ovarian adenocarcinoma cells.

This experiment intended to assess the bio-distribution and activity of amphoteric liposomes/miR34a and amphoteric liposomes/miR-34a-SL. To this end, experimental model female nude mice bearing the orthotopic tumors received three series of repeated intraperitoneal (IP) injections (at days 20, 22 and 25) with amphoteric liposomes/miRNA in concentration of 7 mg/kg of miRNA. Twenty-four hours after the last dose the tumors were removed, and RNA extracted.

The formulations administered to the mice (n=7 each) were prepared as described in Sections I and IV.2, and were as follows: two formulations (with and without SL, with and without folate), one non-formulated miR-34a-SL and two negative controls of saline or lipids without RNA, and a formulation including siRNA and cholesterol as summarized in Tables 16 and 17 below.

TABLE 16

Formulations for IP treatment

| No. | DOPC 10 mg/mL t-butanol mL | Ampholip1 1.2 mg/mL (t-but/H₂O 1/1) mL | Folate-PEG DSPE 5 mg/mL t-but µl | Tween20 10% (H₂O) µl |
|---|---|---|---|---|
| 1. miR-34a | 2.48 | 3.15 | 204.7 | 40.9 |
| 2. miR-34a-SL | 2.48 | 3.15 | — | 40.9 |
| 3. siRNA | 2.86 | 3.63 | 208 | 47.2 |
| 4. siRNA/Chol | 2.86 | 3.63 | 208 | 47.2 |
| 9. - control | 2.48 | 3.15 | 204.7 | 40.9 |

The dry mixture were hydrated with 0.47 mL miRNA (10 mg/mL) and 20 µl citrate buffer pH 4.3 and subjected to four (4) freeze-thaw cycles. PBS was added to complete a volume of 6.75 mL, and each formulation was aliquoted in three (3) vials (2.25 mL each).

TABLE 17

Formulations for IP treatment

| Group | Name |
|---|---|
| 1M | DOPC/Ampholip1/Folate/miR-34a |
| 2M | DOPC/Ampholip1/miR-34a-SL |
| 3M | Saline/miR-34a-SL |
| 9M | DOPC/Ampholip1/Folate - Negative control |
| 10M | Saline- Negative control |

Figure 7:
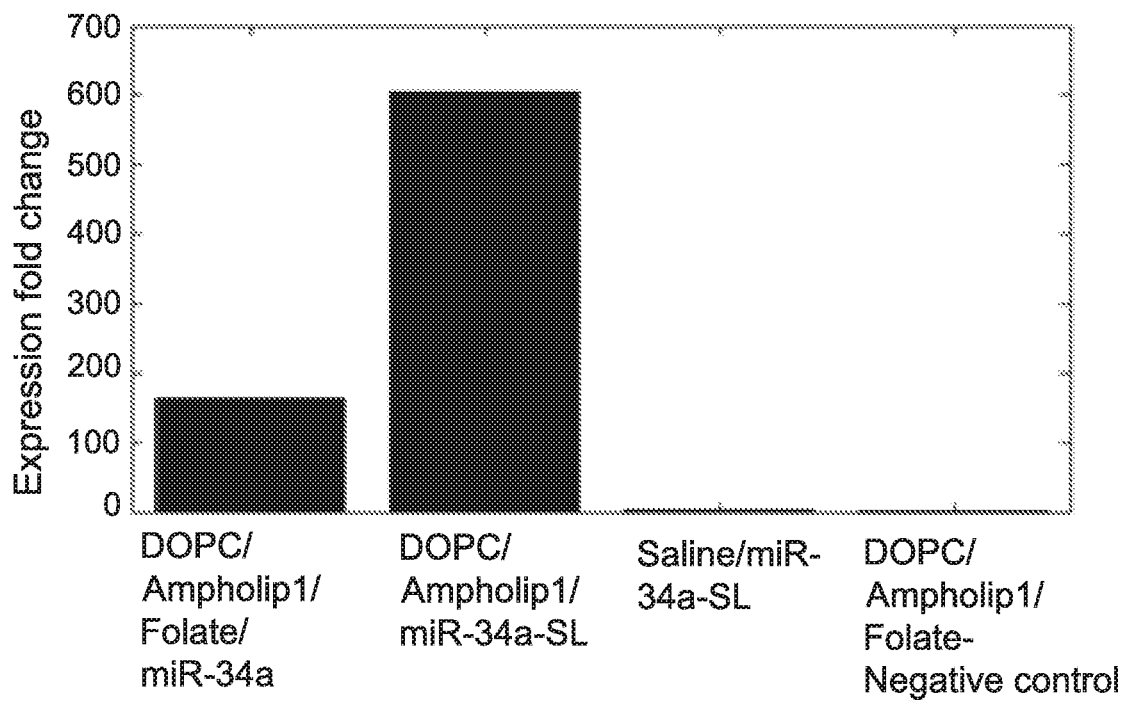
FIG. 7 shows a bar graph of the fold change of miR-34a accumulation in the tumor samples following treatment with DOPC/Ampholip1/Folate/miR-34a, DOPC/Ampholip1/miR-34a-SL, Saline/miR-34a-SL, or Saline only, relative to DOPC/Ampholip1/Folate (Ampholip Negative control), at a linear scale. X-axis shows each treatment, Y-axis shows the fold change of miR-34a expression relative to the formulation with no duplex.

Accumulation levels of miR-34a were quantified in the tumor samples and are shown in FIG. 7. The analysis revealed a 604-fold enrichment of miR-34a-SL and a 163-fold enrichment of miR-34a with folate formulation relative to the negative controls. Non-formulated miR-34a-SL was only two fold enriched, suggesting that the formulation stabilizes the miRNA and enables the penetrance of the RNA into the cells. FIG. 7 shows fold change of miR-34a accumulation relative to negative control lipids treated groups (linear scale).

IV.4.2 Knock Down for miR-34a Targets (Ampholip1)

miR-34a known targets were tested to detect gene suppression activity. For that end, RNA was extracted, and qPCR was performed for the detection of three targets: MET (proto-oncogene, receptor tyrosine kinase), E2F3 (transcription factor 3) and CDK6 (cyclin-dependent kinase 6). The expression levels of the three target genes was normalized to the house keeping gene RPS20.

Figure 8:
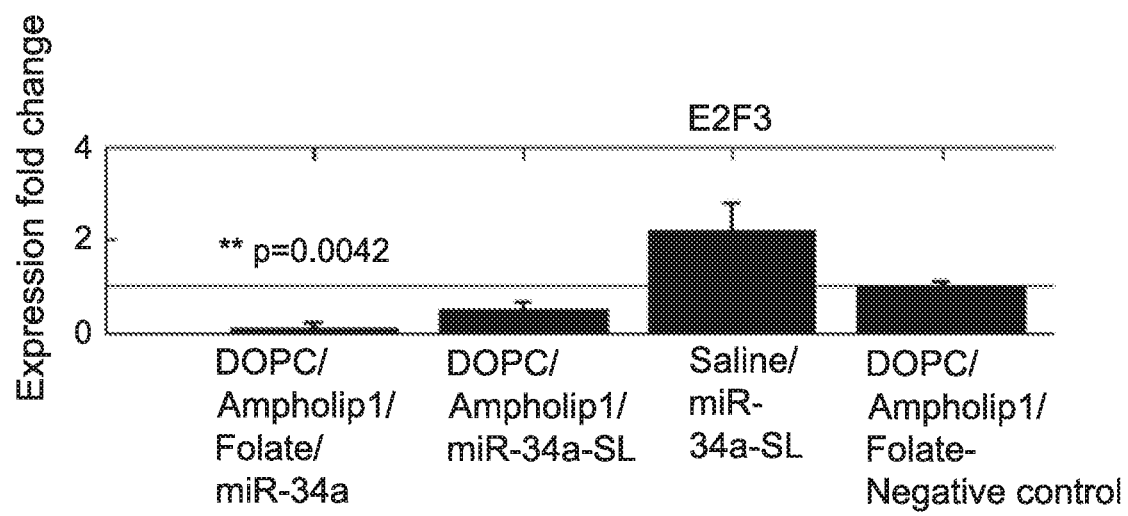
FIG. 8 shows a bar graph representing the expression fold change of miR-34a target E2F3 further to in vivo treatment with DOPC/Ampholip1/Folate/miR-34a, DOPC/Ampholip 1/miR-34a-SL, Saline/miR-34a-SL, DOPC/Ampholip 1/Folate (Ampholip Negative control). X-axis shows each treatment, Y-axis shows the fold change of miR-34a expression relative to the formulation with no duplex.

The results are presented in FIG. 8. SL-formulation treated group reached the highest max dRN with a mild decrease in the target MET and CDK6 genes upon treatment with formulated miR relative to the controls (not shown)). For E2F3 mRNA there was a statistically significantly different from the lipids control alone (p=0.0042, Bonferroni correction). It may be concluded that miR-34a and miR-34a-SL arrived to the tumors and was also active.

IV.4.3 Activity of miRNA/Ampholip 2 Formulations

In order to assess the biodistribution and activity of the miR-34a (4 mg/kg) in Ampholip2 formulation, athymic nude female mice bearing SKOV-3 human ovarian carcinoma model received two intraperitoneal (IP) treatments at days 32 and 33 with RNA concentrations of 4 mg/kg. Accumulation of the miRNA/Ampholip2 formulations was analyzed in mouse tumors and liver, 6 hours after the last injection. The results are shown in FIG. 9.

Figure 9:
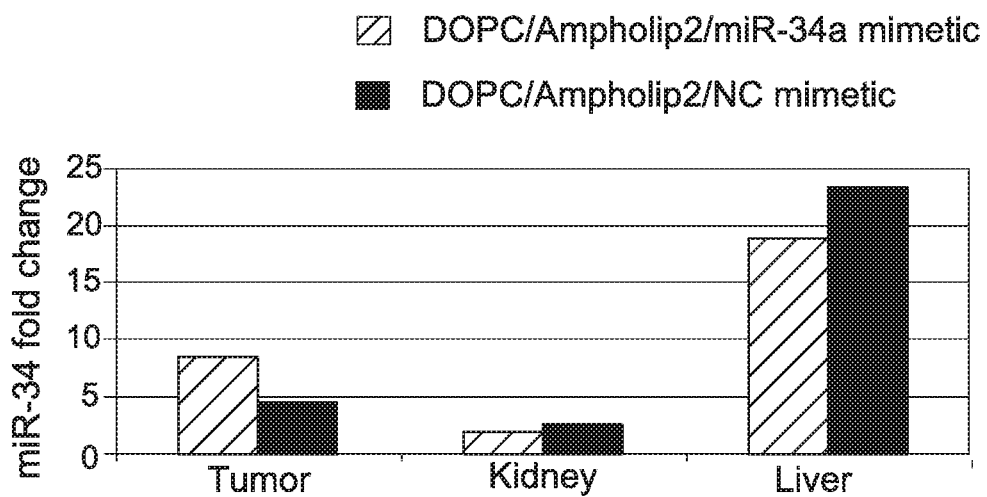
FIG. 9 shows a bar graph representing the accumulation of the miRNA/Ampholip2 formulations (shown as fold change) in vivo following intraperitoneal injection of DOPC/Ampholip2 formulations with or without miR-34a, in the tumor, in the kidneys or in the liver.

As shown in FIG. 9, quantification of the/DOPC/Ampholip2/miR-34a formulations in tumor tissue indicated that the formulations were found at about 8-fold higher amount in tumor tissue compared to control saline treated group. Accumulation was also observed in the liver of the treated animals.

IV.4.4 In Vivo Activity of PLK1 siRNA Delivered by DOPC/Ampholip on SKOV3 Tumors (Ampholip 1)

The study was aimed to assess the activity of the PLK1 siRNA encapsulated in DOPC/Ampholip1 following a single intraperitoneal (IP) injection, in the orthotopic SK-OV-3 human ovarian carcinoma model in athymic nude female mice. In this study tumor bearing mice were treated with a single intravenous (IV) administration of 2 mg/kg PLK1 or EGFP siRNA formulated with DOPC/Ampholip1. Tumors were collected at either 6-hour or 24 hours after treatment. siRNA and target mRNA in the tumors were quantified by qPCR. In addition, siRNA was extracted from the plasma using Triton X-100 extraction. For determining the PLK1 siRNA levels in the samples, cDNA was prepared using the stem loop method for siRNA detection. qPCR was carried out according to standard protocols. In a slight variation to the protocol the SYBR fast ABI prism Ready mix kit (KAPA cat no. KK-KK4605) was used with an elongation/extension time of 30 seconds. 0.4 µl of each primer and 6.2 µl of water was used per sample in the reaction mix. For quantifying target mRNA levels RNA was isolated using a commercial kit (EZ-RNA kit, Biological Industries, catalogue no. 20-410-100) according to manufacturer's instructions. RNA (1 µg of each sample) was used as a template for cDNA synthesis using a random primer mix (Invitrogen 48190-011) and SuperScriptII kit (Invitrogen, 18064-014). In order to determine siRNA activity, the amount of the target gene transcript (mRNA) in each RNA sample was quantified using qPCR and normalized to the amount of a reference gene. Each qPCR reaction mixture included: 3 µl of the appropriate dilution of the cDNA sample, 17 µl of a pre-made mixture containing: 0.4 µl forward +0.4 µl Reverse primers (at 10 µM concentration), 10 µl KAPA SYBR Mix (KAPA BIOSYSTEMS, KK4605) and DDW up to 17 µl. Reactions were run on an Applied Biosystem 7300 PCR machine.

Figure 10:
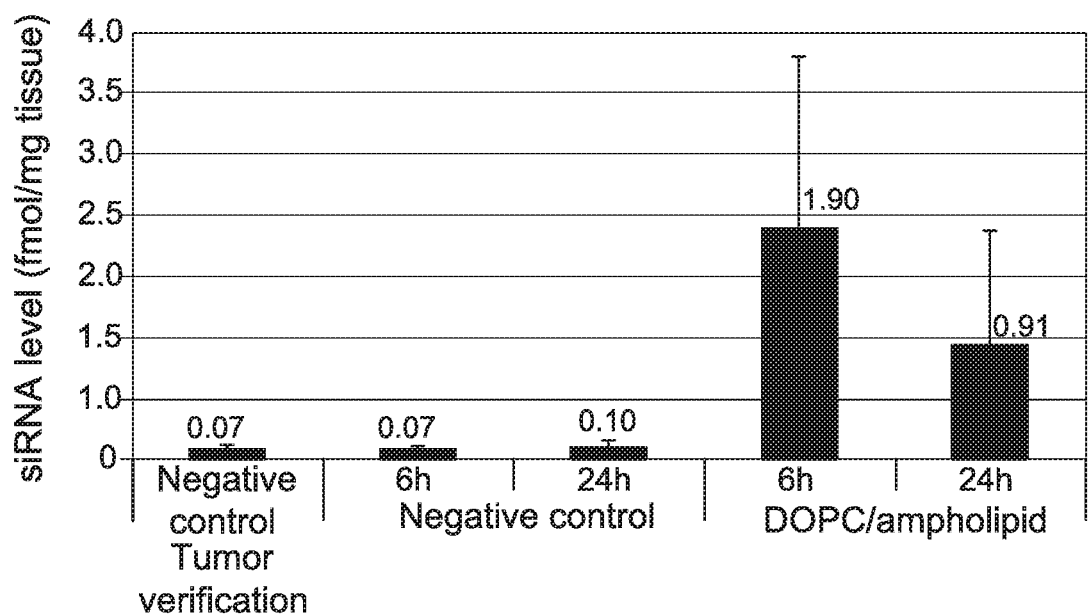
FIG. 10 shows a bar graph representing the PLK1_28 siRNA levels in tumor tissue after 6 or 24 hours post-treatment of DOPC/Ampholip1/PLK1-siRNA, compared with saline-treated group. X-axis shows the treatment groups after 6- or 24-hour treatment. Y-axis shows siRNA level as fmol/mg.

PLK1 siRNA quantification indicated that the DOPC/Ampholip1 formulated PLK1 siRNA was found in ~20 fold higher amount in tumor tissue compared to control saline treated group. Results are shown in FIGS. 10 and 11.

Figure 11:
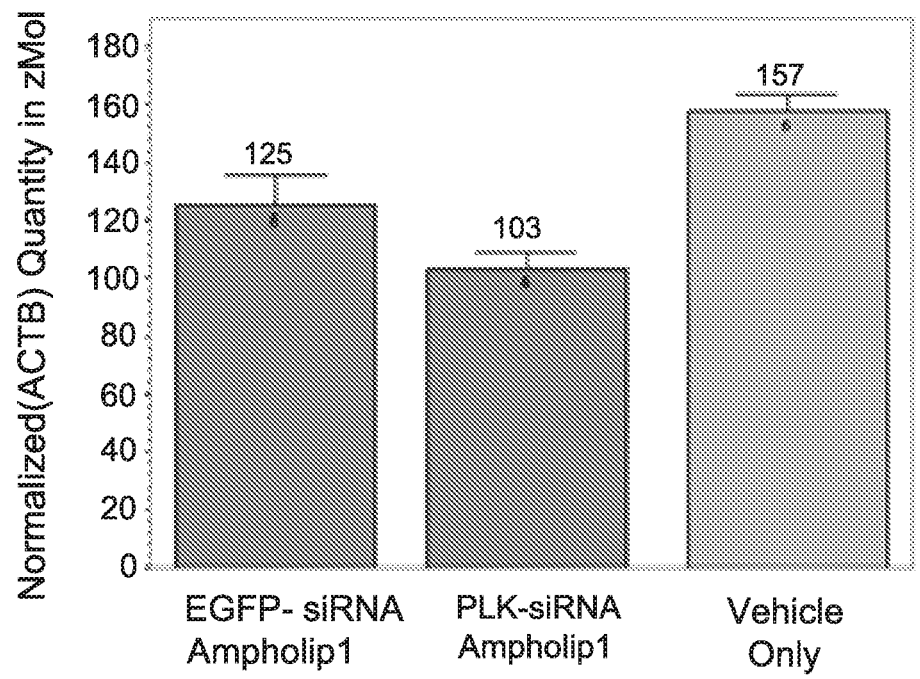
FIG. 11 shows a bar graph representing the PLK1_28 mRNA levels in tumor tissue 24 hours post-treatment of DOPC/Ampholip1/PLK1-siRNA, compared with saline-treated group. X-axis shows the treatment groups, from left to right: EGFP-siRNA+Ampholip; PLK-siRNA+Ampholip; vehicle only. Y-axis shows mRNA levels in zmol, normalized for Beta-Actin (ACTB).

Examining the PLK1 mRNA levels in tumor tissue 24 hours after treatment with DOPC/Ampholip1 formulated PLK1 indicated on 35% reduction of target mRNA compared to the control saline treated group (FIG. 11).

IV.4.5 Activity of siRNA (Ampholip2)

The study was aimed to assess the activity of the PLK1 siRNA encapsulated in DOPC/Ampholip2 following two intraperitoneal (IP) injection, in the orthotopic SK-OV-3 human ovarian carcinoma model in athymic nude female mice. In this study tumor bearing mice were treated with a single intravenous (IV) administration of 4 mg/kg PLK1 siRNA formulated with DOPC/Ampholip2. Tumor was collected at 6 hours or 24 hours after treatment and siRNA and target mRNA were quantified by qPCR, further to Triton X-100 extraction. For determining the PLK1 siRNA levels in the samples cDNA was prepared using the Stem loop method for siRNA detection. qPCR was carried out according to the commercial kit SYBR Fast ABI Prism Ready mix kit (KAPA cat no. KK-KK4605), with a slight variation to the manufacturer's protocol in which an elongation/extension time of 30 seconds, s was used. 0.4 µl of each primer and 6.2 µl of water was used per sample in the reaction mix. For quantifying target mRNA levels RNA was isolated using EZ-RNA kit (Biological Industries, 20-410-100) according to manufacturer instructions. RNA (1 μg of each sample) was used as a template for cDNA synthesis using a random primer mix (Invitrogen 48190-011) and SuperScriptII Kit® (Invitrogen, 18064-014). In order to determine siRNA activity, the amount of the target gene transcript (mRNA) in each RNA sample was quantified using qPCR and normalized to the quantity of a reference gene. Each qPCR reaction mixture included: 3 μl of the appropriate dilution of the cDNA sample, 17 μl of a pre-made mixture containing: 0.4 μl forward +0.4 μl Reverse primers (at 10 μM concentration), 10 μl KAPA SYBR Mix (KAPA BIOSYSTEMS, KK4605) and double distilled water (DDW) up to 17 μl.

Figure 12:
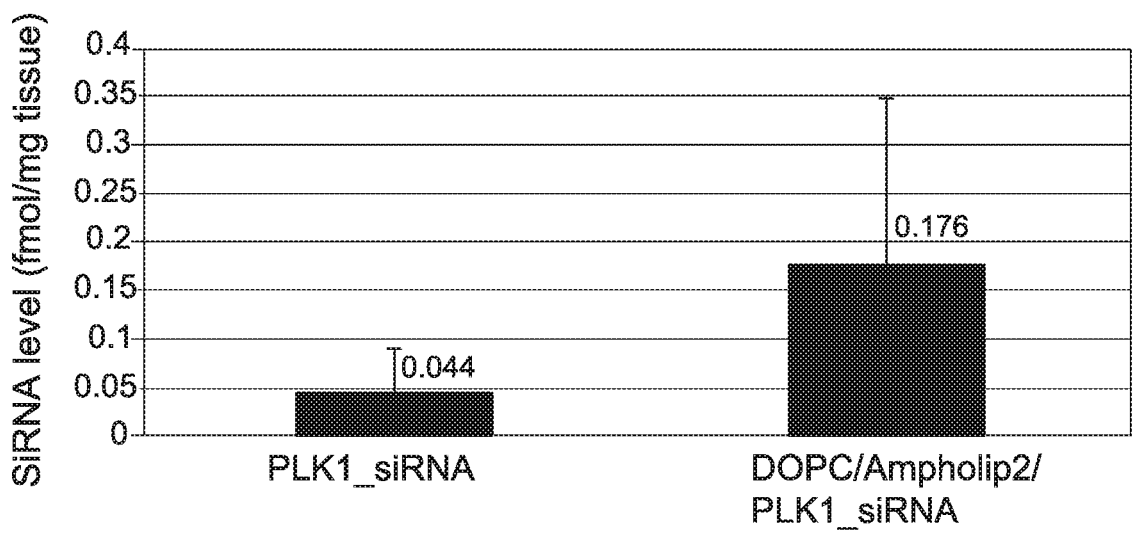
FIG. 12 shows a bar graph representing the PLK1_28 siRNA levels in tumor tissue after 24 hours post-treatment of DOPC/Ampholip2/PLK1-siRNA, compared with non-formulated PLK1 siRNA. X-axis shows non-formulated PLK1 siRNA (left) and DOPC/Ampholip2/PLK1-siRNA (right), after 24-hour treatment. Y-axis shows siRNA level as fmol/mg.
Figure 13:
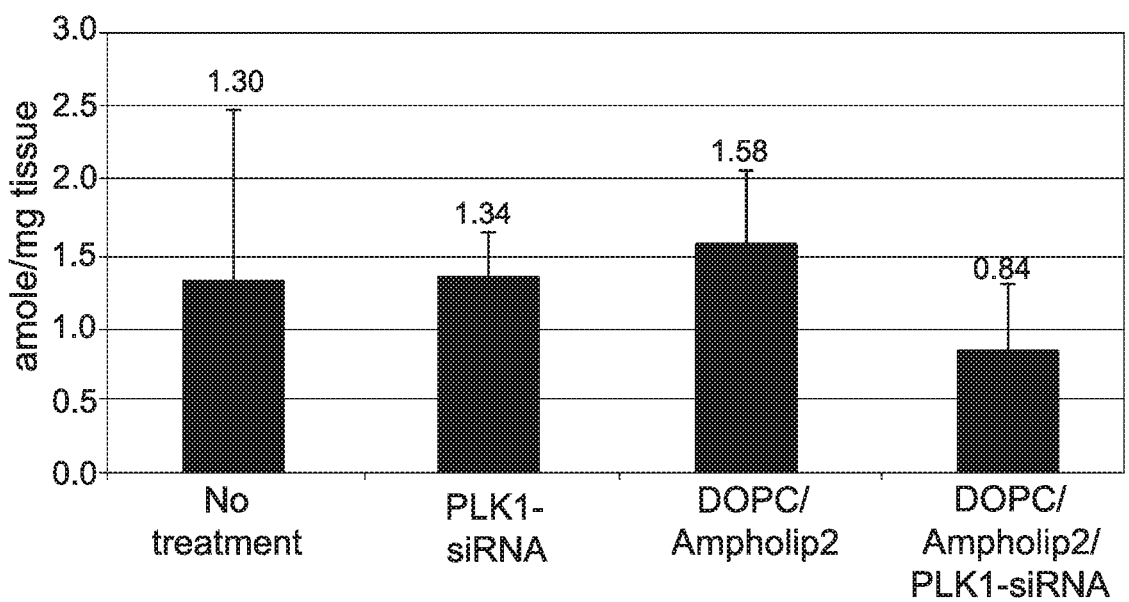
FIG. 13 shows a bar graph representing the PLK1_28 mRNA levels in tumor tissue 24 hours post-treatment. X-axis shows, from left to right, no treatment, non-formulated PLK1_28 siRNA, DOPC/Ampholip2, and DOPC/Ampholip2/PLK1-siRNA treated groups. Y-axis shows normalized mRNA levels as amole/mg tissue.

PLK1 siRNA quantification indicated that the DOPC/Ampholip2 formulated PLK1 siRNA was found in ~4-fold higher amount in tumor tissue compared to non-formulated siRNA. Results are shown in FIGS. 12 and 13.

Examining the PLK1 mRNA levels in tumor tissue 24 hours after treatment with DOPC/Ampholip2 formulated PLK1 siRNA indicated a 40% reduction of target mRNA compared to the non-formulated siRNA and more than 50% reduction compared to control DOPC/Ampholip2 group.

IV.4.6 In Vivo Evaluation of Anti-Cancer Efficacy of miRNA Encapsulated with Ampholip Formulation An orthotopic SK-OV-3 human ovarian carcinoma model in athymic nude female mice was generated for evaluation of the efficacy of treatment with Ampholip1 formulations containing miR-34a mimetic. The formulations used for the treatment are described in Table 18.

TABLE 18

Formulations used in vivo

| IN VIVO SKOV | Size | | | | Zeta (mV) |
|---|---|---|---|---|---|
| | Zav (d · nm) | PdI | PK1 Intensity | PK1 % Area | |
| 1-DOPC/Ampholip1/miR-34a__Dup149 | 1393 ± 159 | 0.82 ± 0.08 | 433 ± 57 | 96.5 ± 3 | −25.6 ± 6.6 |
| 2- DOPC/Ampholip1/Cel-miR-39 (Negative control) | 876 ± 220 | 0.7 ± 0.15 | 586.7 ± 227 | 87.4 ± 19.6 | −13.4 ± 2.1 |
| 3- DOPC/Ampholip1/miR-34-SL (conjugated) | 320 ± 66 | 0.54 ± 0.08 | 504.4 ± 116 | 63.5 ± 12.3 | −29.6 ± 1.6 |

Tumor induction was done through the injection of $10 \times 10^6$ SK-OV-3 cells per animal, via intraperitoneal (IP). Seven days following tumor induction, the animals (8 animals per treatment group) were administered nine intraperitoneal (IP) injections (three injections per week, during three weeks) of Ampholip1 formulation containing miR-34a or SL-conjugated or non-conjugated. For negative control, mice were injected with water for injection (WFI). Treatments were administered IP at a dose volume of 8 mL/kg. The first administration was performed seven days following tumor induction, followed by additional eight injections in intervals of about 48-72 hours. MRI scans for tumor volume assessment and foci detection were performed at 4-5, 10-11 and 16-17 days post last injection.

Figure 14:
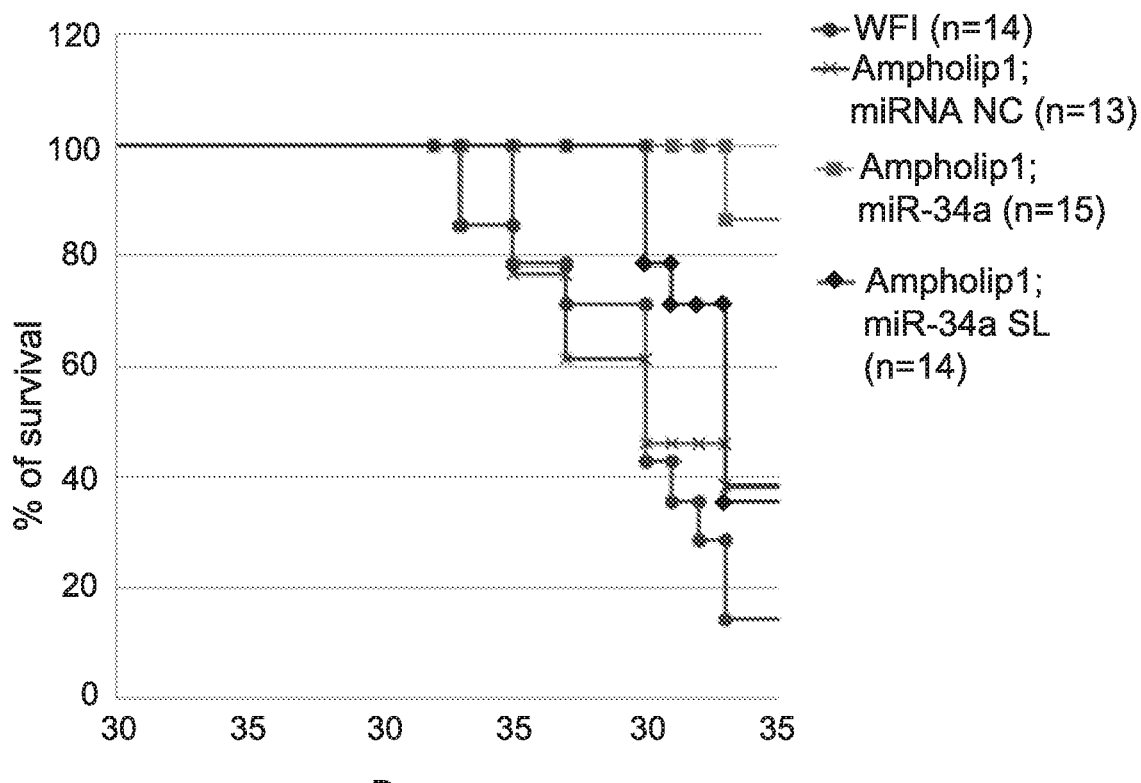
FIG. 14 shows a graph representing percentage of survival (Y-axis) in days (X-axis), for animals treated with DOPC/Ampholip1/miR-34a-SL (diamonds), DOPC/Ampholip1/miR-34a non-conjugated (squares), DOPC/Ampholip1/miR-NC (negative control; X) or with water for injection (WFI, circles).
Figure 15:
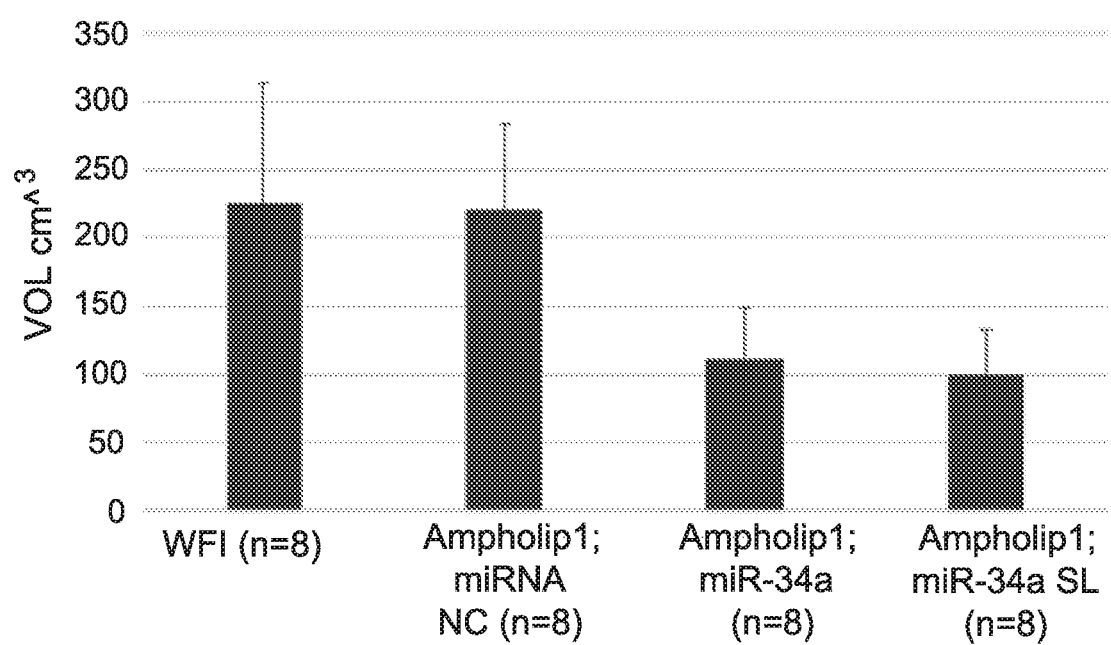
FIG. 15 shows a graph representing the size of the tumors measured by MRI at days 10-11, following each one of the indicated treatments, from left to right, WFI, Ampholip1/miR-NC, Ampholip1/miR-34a non-conjugated, and Ampholip1/miR-34a-SL.

Representative results are presented in FIGS. 14 and 15. The percentage of survival (life span) was best in animals following the treatment with Ampholip1 formulation carrying miR-34a non-conjugated, closely followed by animals treated with Ampholip1 formulation carrying miR-34a SL-conjugated FIG. 14). Similarly, the size of the tumor, as measured by MRI, was significantly decreased in animals following treated with Ampholip1 formulation carrying miR-34a non-conjugated or SL-conjugated (FIG. 15).

Table 19 presents the analysis of tumor size, evaluated by MRI, for all treatments at the three time-points, at days 4-5, 10-11 and 16-17 following the last treatment. The results show that the effect of the treatment may be observed up to two weeks after the last treatment.

TABLE 19

Tumor volume following Ampholip1 + miR treatment

| | Tumor volume (cm$^3$) | | |
|---|---|---|---|
| Treatment | Day 4-5 | Day 10-11 | Day 16-17 |
| WFI | 238.9 | 225.8 | 316.5 |
| Ampholip1 + miR-NC | 133.8 | 220.5 | 252.8 |
| Ampholip1 + miR-34a | 97.6 | 111.5 | 161.5 |
| Ampholip1 + miR-34a-SL | 90 | 99 | 152 |

IV.4.7. In Vivo Validation and Feasibility Study in the MDA-231 Human Breast Cancer Subcutaneous Model of Radiolabeled Folate-Targeted Liposomes with miR-34a Accumulation of folate-targeted liposomes (Ampholip1) with miR-34a following a single intravenous (IV) injection in the MDA-231 human breast cancer subcutaneous animal model was evaluated. The formulation used was DOPC/Ampholip1/Tween20/folate-$^{2000}$mPEG-DSPE/miR-34a in a 100/10/1/1/1 mole ratio.

For tumor induction, MDA-231 human breast cancer cells were injected at a concentration of $40 \times 10^6$ cells/ml or $50 \times 10^6$ cells/ml, at a dose volume of 0.1 ml per animal ($4 \times 10^6$ or $5 \times 10^6$ cells per animal, respectively) by a single subcutaneously (SC) injection into the right cranial trunk region, using 27G needle.

The liposomes used in this study [DOPC/Ampholip1/Tween20/folate-$^{2000}$mPEG-DSPE/miR-34a in a 100/10/1/1/1 mole ratio] were labeled with $^3$H-cholesteryl hexadecyl ether (CE) which serves as a non-transferable, non-metabolizable liposome marker. 2 mg of miR-34a non-conjugated duplex 149 was kept at a 10 mg/ml concentration, 0.2 ml. Solutions of 1.1 ml DOPC (10 mg/ml) t-But with 1.4 ml of Ampholip1 (1.2 mg/ml) t-But/H$_2$O, 0.09 ml PEG-DSPE-Folate (5 mg/ml) t-But, 20 μl of Tween 10% in H$_2$O and 7 μl $^3$H-CE (~1 μCi/ml of final preparation) were mixed. The above mix lipids component (providing the liposomal formulation) were fast frozen in liquid nitrogen then lyophilized overnight. The dry lipids were hydrated with 0.2 ml 10 mg/ml miRNA and 20 μl citrate buffer pH4.3 and subjected to six freeze-thaw cycles, followed by the addition of 2.18 ml histidine/saline buffer pH 6.5. The suspension was extruded by six cycles of filtration through 200 nm and 80 nm filters.

About 5 days after arrival, athymic nude female mice (n=16) were injected subcutaneously into the right cranial trunk region with MDA-231 cells. The mice were checked visually for tumor progression and discomfort on a daily basis, excluding weekends. Tumor size was measured on days 4, 8, 11, 15, 23, 29 and 32. At day 38 post-tumor induction, mice were injected IV with 5 mg/kg of formulated miRNA with folate-targeted radiolabeled liposomes. 20 hours post-dosing animals were subjected to bleeding followed by sacrifice and organ removal.

Figure 16:
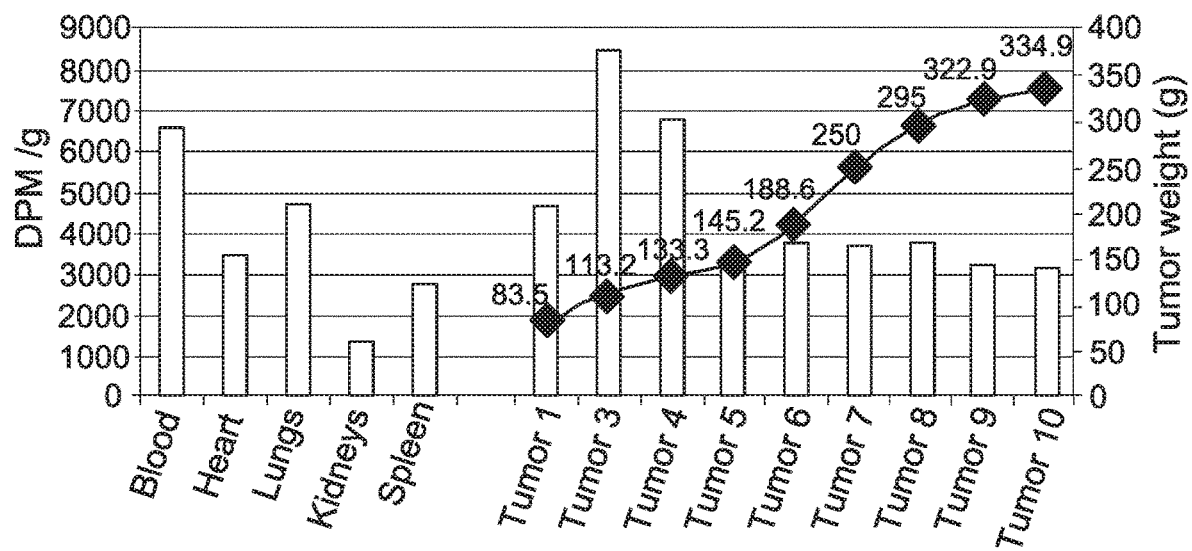
FIG. 16 is a graph showing the specific amount of liposomes (calculated based on the amount of radioactivity detected) detected in the blood, heart, lungs, kidneys, spleen and in nine (9) induced tumors, 20 hours post-IV administration. X-axis, organs or tumors; Y-axis, radioactivity measured per gram (DPM/g); Z-axis, tumor weight (g). DPM=disintegrations per minute.
Figure 17:
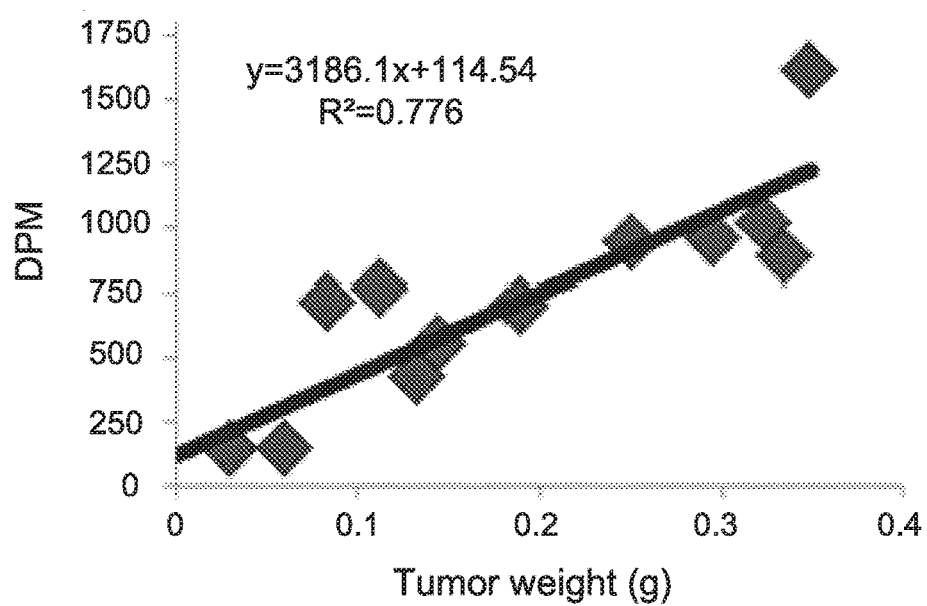
FIG. 17 is a graph showing the amount of liposomes (DPM) detected in tumors 20 hours post-IV administration. X-axis, organs or tumors; Y-axis, radioactivity measured per gram (DPM/g); Z-axis, tumor weight (g).

The results are presented in FIG. 16 and FIG. 17. Significant levels of liposomes were detected in blood and tumors 20 hours post-dosing. The specific amount of liposomes (DPM/gr) decreases slightly as the size of the tumor increases (FIG. 16). The amount of liposomes in the tumors showed a positive correlation with tumor weight (FIG. 17).

V. Further Protocols Used in this Study

V.1 Cell Growth and Maintenance

SKOV-3 ovarian cancer cell line was purchased from NCI. Cells were grown under standard growth conditions.

V.2 RNA Extraction

RNA extraction from cell lines was done using EZ-RNA II kit (Biological Industries, Israel). This method extracts total RNA from the cells including small RNAs. RNA extraction from fresh frozen tissue was carried out using "miRVana" total RNA extraction kit (Ambion). RNA extraction from plasma samples was done using Rosetta's protocol of extraction from body fluids.

RNA extraction from tumour samples was done using EZ-RNA II kit (Biological Industries, Israel), using a starting volume of 0.7 ml solution A (EZ-RNA II), a known amount of tissue powder, and a double extraction of the organic phase. Linear acrylamide (Ambion Cat. No. 9520) was added as carrier.

V.3 Triton Lysate Preparation

Tumour samples were weighed and 5× vol 0.25% pre-heated Triton X-100 added to each sample. The samples were vortexed and incubated at 95° C. for 10 min. Lysates were vortexed twice more during this incubation. After the incubation the lysates were cooled on ice for 10 min and centrifuged at 20,000 g for 20 min at 4° C. The supernatants were taken to clean tubes and frozen at −80° C. until further use.

V.4 cDNA Preparation

For gene expression analysis, cDNA was prepared using a starting amount of 1 µg RNA in a 15 µl reaction. 1.5. pg Luc in-vitro translated RNA was added to each reaction. Luc in vitro translated RNA was added in the mix together with the DNAse step.

V.5 Transfection

Transfection of cells with miRNA mimetic was done using Lipofectamine2000 reagent (Invitrogen, Cat #11668027), according to manufacturer's instructions. Alternatively, transfection was conducted with different novel delivery systems.

V.6 Dual-Luciferase Reporter Assay

Reverse compliment sequences to hsa-miR-34a were inserted into the 3' UTR of *Renilla* luciferase in psi-CHECK-2 vector (Promega). Cells were transfected in triplicates with the vector or co-transfected with a vector and miRNA mimetic. Luminescence was assayed 24-72 hours later using the Dual-Luciferase Reporter-Assay-System (Promega, Cat # E1961) according to manufacturer's instructions. Results were normalized to the constitutively expressed firefly luciferase from the same vector, and shown as the ratio between the various treatments and cells transfected with a non-modified vector.

V.7 qRT-PCR for miRNAs

RNA was subjected to a polyadenylation reaction by incubation in the presence of poly (A) polymerase (PAP; Takara-2180A), $MnCl_2$, and ATP for 1 h at 37° C. Reverse transcription was performed using an oligo dT primer harboring a consensus sequence using SuperScript II RT (Invitrogen). The cDNA was amplified by real time PCR; this reaction contained a microRNA specific forward primer, a TaqMan® probe complementary to the 3' of the specific microRNA sequence as well as to part of the polyA adaptor sequence, and a universal reverse primer complementary to the consensus 3' sequence of the oligo dT tail.

V.8 qRT-PCR for mRNAs 500 ng-1 µg of total RNA were reverse-transcribed using Superscript II (Invitrogen). Then, 0.165 ng-5 ng of cDNA were used in a qRT-PCR reaction. mRNA was quantified by Real Time qPCR SYBR Green method, using a commercial 7500 Real Time PCR system (ABI) with a default threshold of 0.2. Each test was done in triplicates. Ct values were normalized to the housekeeping genes TBP and RPS20.

VI. Sequences

Sequences referred to in the present application for miRNAs, miRNA targets and siRNAs.

| Sequence Table 20A | | |
|---|---|---|
| miR or Target Gene name | Sequence | SEQ ID NO. |
| hsa-miR-34a -Guide | 5'Ph-UGGCAGUGUCUUAGCUGGUUGU | 1 |
| hsa-miR-34a -Passenger | CAAUCAGCAAGUAUACUGCCCU | 2 |
| hsa-miR-34a-SL - Guide | 5'Ph-UGGCAGUGUCUUAGCUGGUUGU | 1 |
| hsa-miR-34a-SL - Passenger | SL-CAAUCAGCAAGUAUACUGCCCU | 3 |
| MET-F | ACTTCACTGGCAGCTTTGC | 4 |
| MET-R | TGGTCTTCAAGTAGCCAAAGG | 5 |
| CDK6-F | TCCCAGGAGAAGAAGACTGG | 6 |
| CDK6-R | TGGAAGTATGGGTGAGACAGG | 7 |
| E2F3-F | AAGGGCCCATTGAGGTTTAC | 8 |

Sequence Table 20A

| miR or Target Gene name | Sequence | SEQ ID NO. |
|---|---|---|
| E2F3-R | TTGGAAGGAATTTGGTCCTC | 9 |
| RPS20-F | AACAAGCCGCAACGTAAAAT | 10 |
| RPS20-R | GGAAACGATCCCACGTCTTA | 11 |
| hsa-miR-34b-5p | UAGGCAGUGUCAUUAGCUGAUUG | 12 |
| hsa-miR-34b-3p | CAAUCACUAACUCCACUGCCAU | 13 |
| hsa-miR-34c-5p | AGGCAGUGUAGUUAGCUGAUUGC | 14 |
| hsa-miR-34c-3p | AAUCACUAACCACACGGCCAGG | 15 |
| miR-34a - Guide (with bulges, no overhangs) | 5'Ph-UGGCAGUGUCUUAGCUGGUUGU | 1 |
| miR-34a - Passenger (with bulges, no overhangs) | ACAAUCAGCAAGUAUACUGCCCUA | 16 |
| miR-34a - Guide (no bulges, no overhangs) | 5'Ph-UGGCAGUGUCUUAGCUGGUUGU | 1 |
| miR-34a - Passenger (no bulges, no overhangs) | ACAACCAGCUAAGACACUGCCA | 17 |

U/C/A/G = 2'O-methylated nucleotide
5'Ph = phosphate added at the 5'end

Sequence Table 20B:

| Name | Strand | Strand sequence and modification pattern 5→3 | SEQ ID NO. |
|---|---|---|---|
| RAC1_28_S1908 | Sense | mC; rG; mU; rG; mC; rA; rA; rA; rG; mU; rG; rG; mU; rA; rU; mC; rC; mU; rA; pi | 18 |
| | AntiSense | mU; rA; rG; rG; rA; mU; rA; rC; mC; rA; mC; rU; mU; rU; mG; rC; mA; rC; mG; pi | 19 |
| RAC1_28_S2404 | Sense | Chol-C6p; mC; rG; mU; rG; mC; rA; rA; rA; rG; mU; rG; rG; mU; rA; rU; mC; rC; mU; rA; pi | 20 |
| | AntiSense | mU; rA; rG; rG; rA; mU; rA; rC; mC; rA; mC; rU; mU; rU; mG; rC; mA; rC; mG; pi | 21 |
| RAC1_28_S2045 | Sense | SLSp; mC; rG; mU; rG; mC; rA; rA; rA; rG; mU; rG; rG; mU; rA; rU; mC; rC; mU; rA; pi | 22 |
| | AntiSense | mU; rA; rG; rG; rA; mU; rA; rC; mC; rA; mC; rU; mU; rU; mG; rC; mA; rC; mG; pi | 23 |
| PLK1_28_S2272 | Sense | SLSp; rA; rG; rA; rA; rG; rA; mU; rG; rC; rU; rU; mC; rA; rG; rA; mC; rA; rG; rU; pi | 24 |
| | AntiSense | rA; rC; mU; rG; rU; rC; mU; rG; rA; rA; rG; rC; rA; rU; mC; rU; mU; rC; mU; pi | 25 |
| PLK1_28_S2054 | Sense | AmC6Np; rA; rG; rA; rA; rG; rA; mU; rG; rC; rU; rU; mC; rA; rG; rA; mC; rA; rG; rU; pi | 26 |
| | AntiSense | rA; rC; mU; rG; rU; rC; mU; rG; rA; rA; rG; rC; rA; rU; mC; rU; mU; rC; mU; pi | 27 |
| EGFP_1_S500 | Sense | rG; mC; rC; mA; rC; mA; rA; mC; rG; mU; rC; mU; rA; mU; rA; mU; rC; mA; rU; pi | 28 |
| | AntiSense | mA; rU; mG; rA; mU; rA; mU; rA; mG; rA; mC; rG; mU; rU; mG; rU; mG; rG; mC; pi | 29 |

| Modification Code | Modification Description |
|---|---|
| m | 2'-O-methyl ribo-nucleotide |
| AmC6Np | Amino-C6-Phosphate |
| Chol-C6p | 5' Cholesterol-C6-phosphate |
| SLSp | SphingoLipid-Spermine_phosphate |

| Sequence Table 20B: |  |
|---|---|
| r | ribo-nucleotide |
| pi | 3' end phosphate |

The invention claimed is:

1. A compound of the general formula (I):

$$D\text{-}Sp\text{-}T\text{-}L_2$$

wherein

T is a moiety comprising three functional groups, each being independently suitable for conjugation or association or coupling with another of the chemical entities in the compound, $L_2$ represents two same or different non-phosphate lipid groups, each lipid group being associated to one of said three functional moieties in T;

Sp represents a spacer group or atom which may or may not be present; and

D is a polyalkylamine group comprising at least one negatively charged moiety and at least one positively charged moiety;

wherein the compound is the structure (IIa) or (IIb):

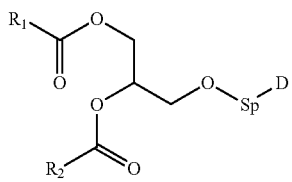

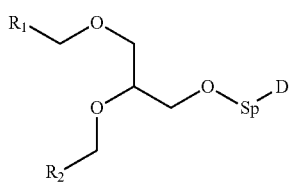

wherein in each of structure (IIa) and (IIb), independently of the other:

each of $R_1$ and $R_2$, independently of the other, represents $C_5$-$C_{24}$ carbon chain.

2. The compound of claim 1, wherein Sp is selected from a carbonyl or carbonyl containing spacer, and from any of the following:

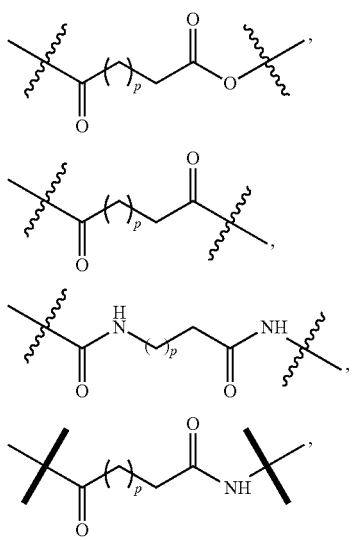

wherein each of p, independent of the structure, is an integer between 0 and 7.

3. A compound having a general structure selected from:

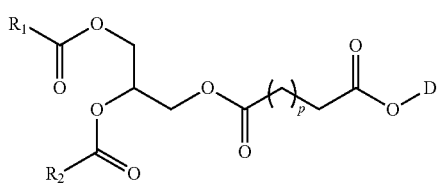

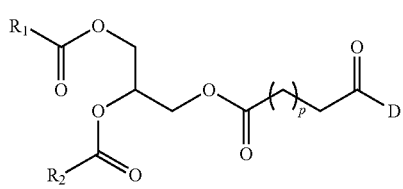

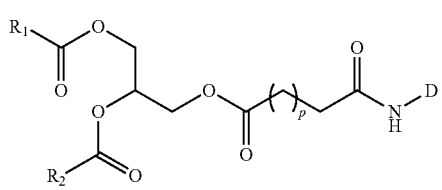

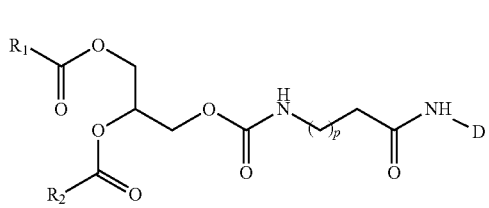

wherein each of $R_1$, $R_2$, and D are as defined in claim 1 and wherein p is an integer between 0 and 7.

4. A compound having the general structure VII:

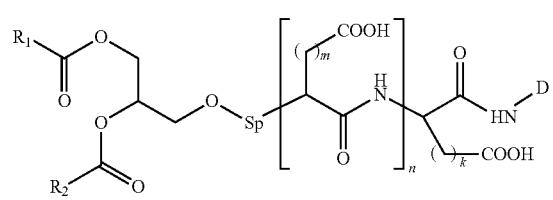

wherein Sp represents a spacer group or an atom which may or may not be present;

D is a polyalkylamine group comprising at least one negatively charged moiety and at least one positively charged moiety;

each of $R_1$ and $R_2$, independently of the other, represents $C_5$-$C_{24}$ carbon chain;

n is an integer between 0 and 3;

m is 1 or 2; and k is 1 or 2.

5. The compound of claim 4, having the formula VIII:

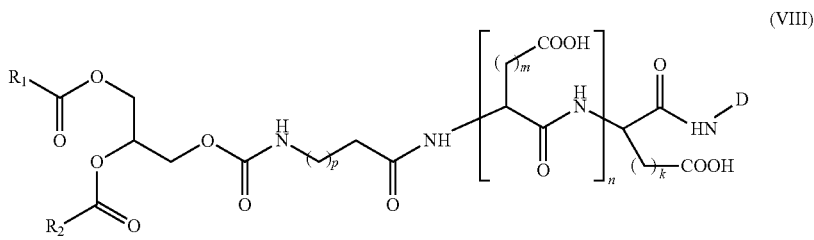

wherein each of $R_1$, $R_2$, D, m, n and k are as defined in claim 4 and wherein p is an integer between 0 and 7.

6. The compound of claim 4 and having the general structure IX:

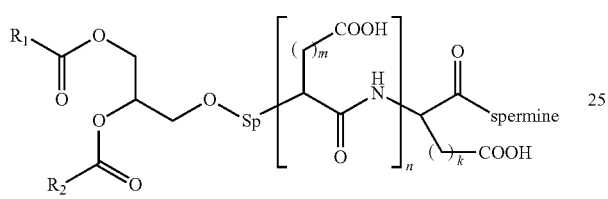

wherein $R_1$, $R_2$, n, m, k and Sp are each as defined in claim 4.

7. The compound of claim 6, wherein Sp is selected from a carbonyl comprising group or from

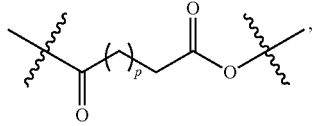

-continued

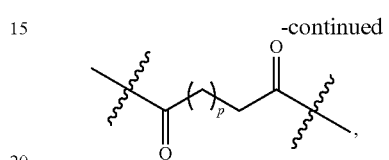

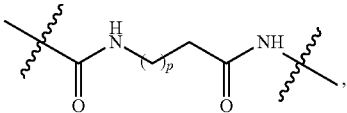

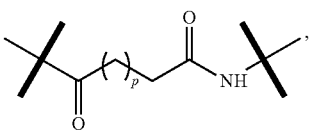

wherein each of p, independent of the structure, is an integer between 0 and 7.

8. The compound of claim 1, wherein the compound has the formula:

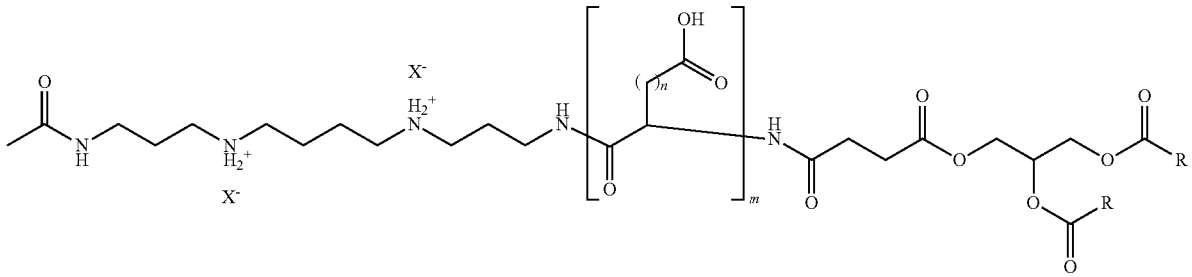

wherein
n is 1 or 2;
m is between 1 and 4, and
wherein each of the counter ions X—, independently of the other, is selected from a halide and $CF_3COO^-$, and wherein each of $R_1$ and $R_2$, independently of the other, represents $C_5$-$C_{24}$ carbon chain.

9. A di-glutamate-di-stearoyl glycerol carbamoyl spermine, or a salt thereof, having the structure:

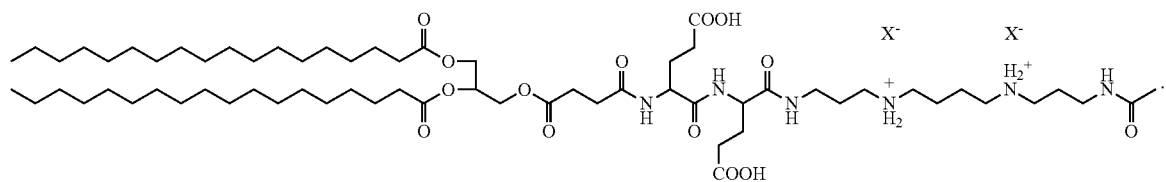
wherein X⁻ is CF₃COO⁻, CH₃COO⁻ or Cl⁻.
10. A compound selected from:
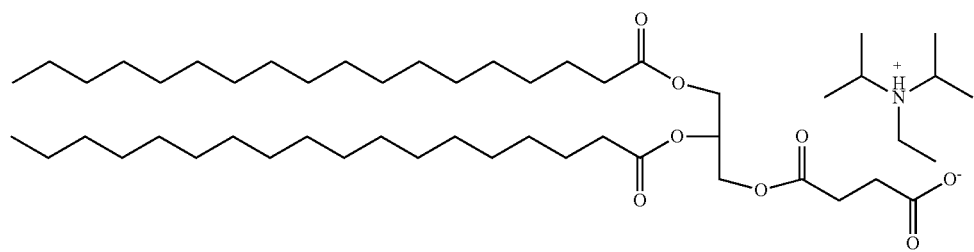
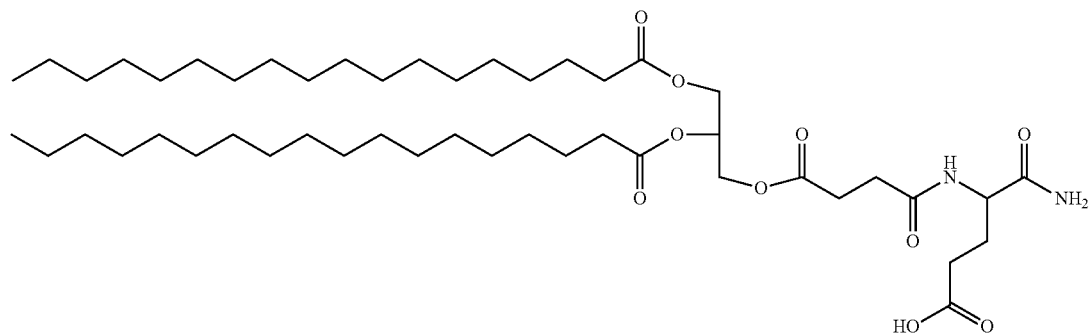
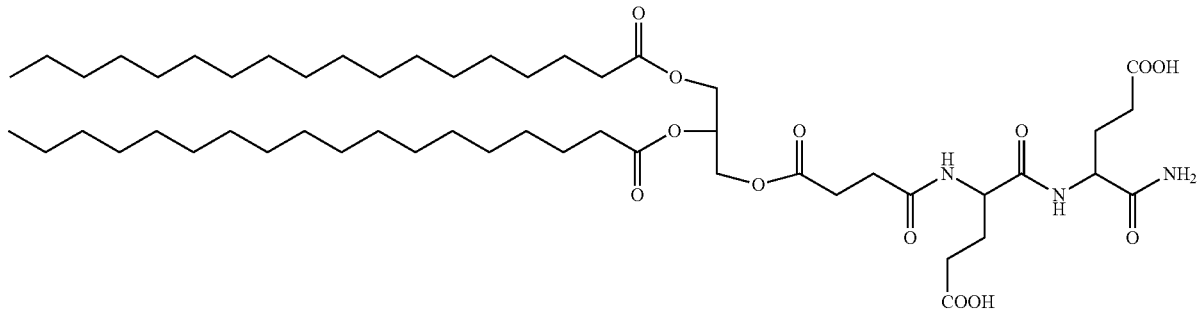
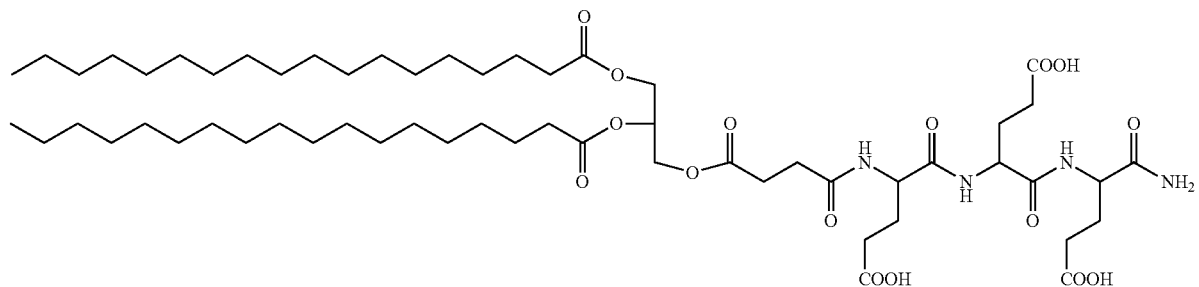

-continued
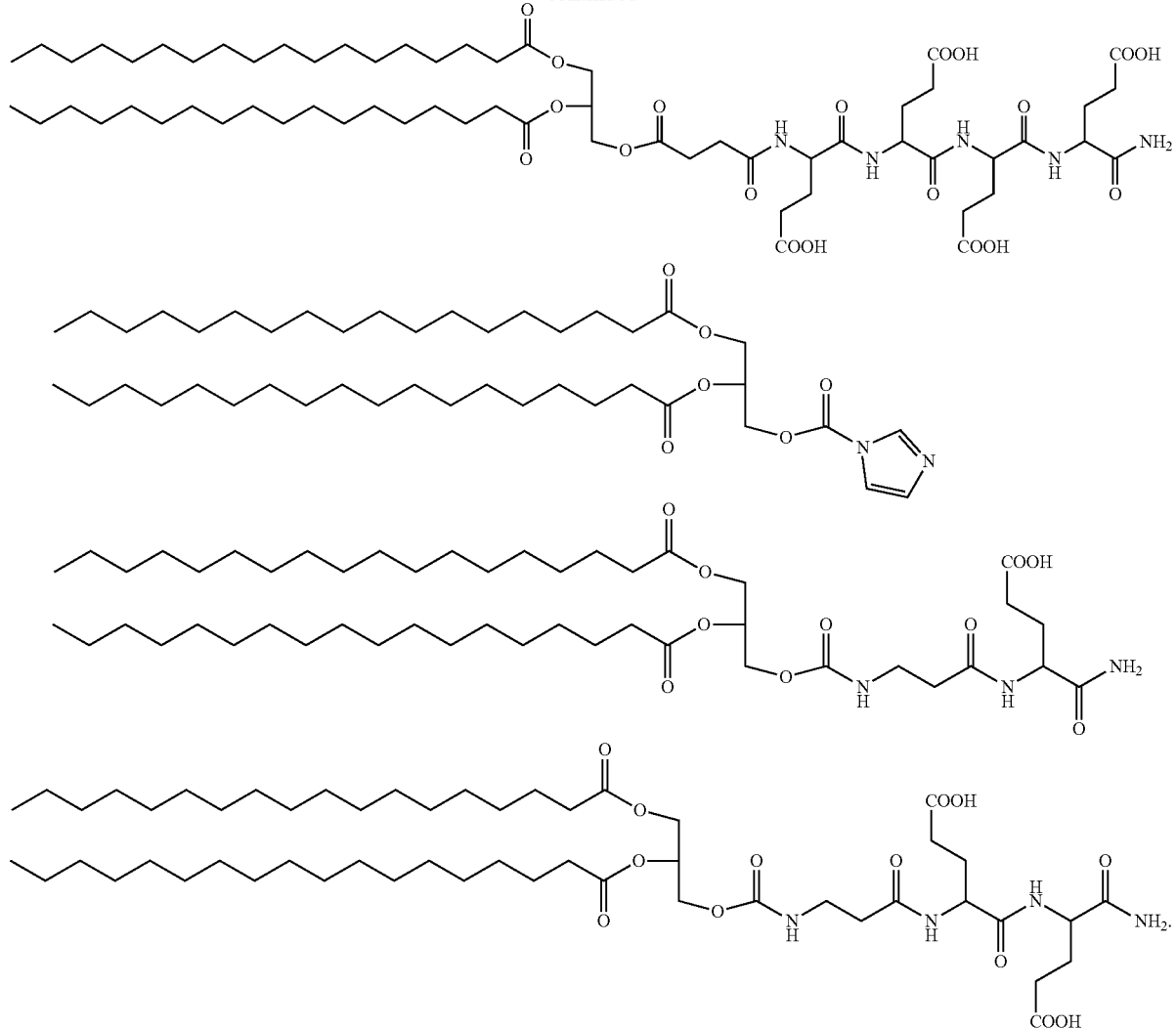

UNITED STATES PATENT AND TRADEMARK OFFICE
CERTIFICATE OF CORRECTION

PATENT NO. : 10,722,599 B2
APPLICATION NO. : 15/548601
DATED : July 28, 2020
INVENTOR(S) : Barenholz et al.

Page 1 of 4

It is certified that error appears in the above-identified patent and that said Letters Patent is hereby corrected as shown below:

In the Specification

Column 8, Lines 23-27:

"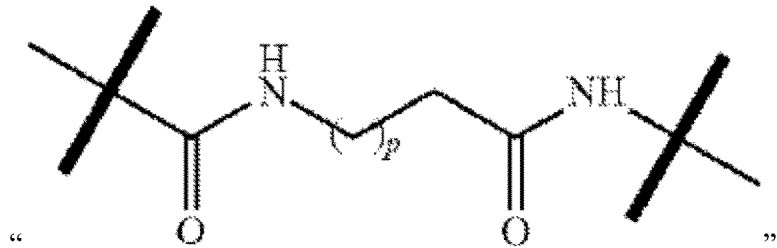"

Should be deleted and replaced with:

-- 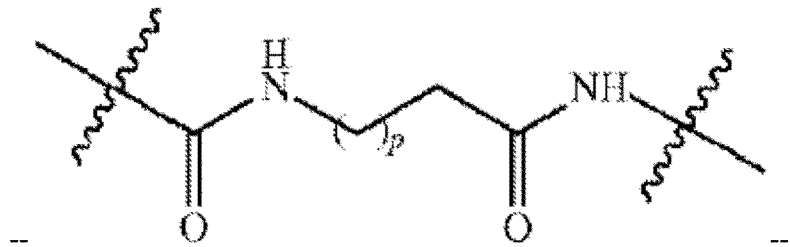 --

Column 8, Lines 28-32:

"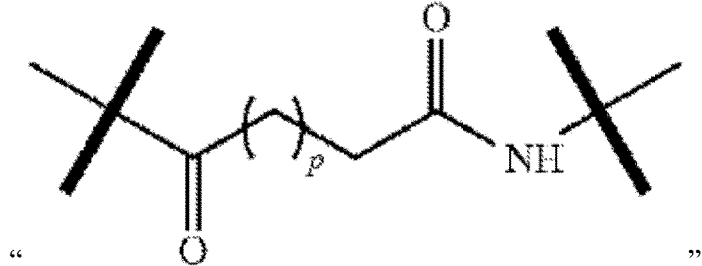"

Should be deleted and replaced with:

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,722,599 B2

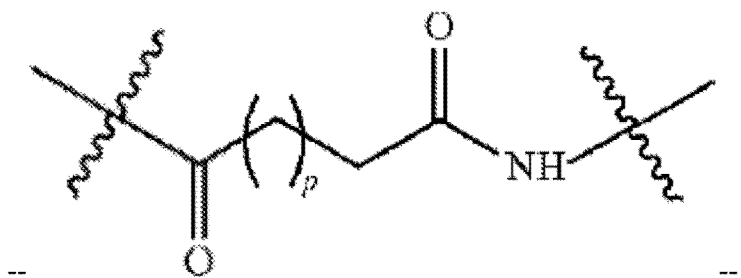

--

Column 12, Lines 7-12:

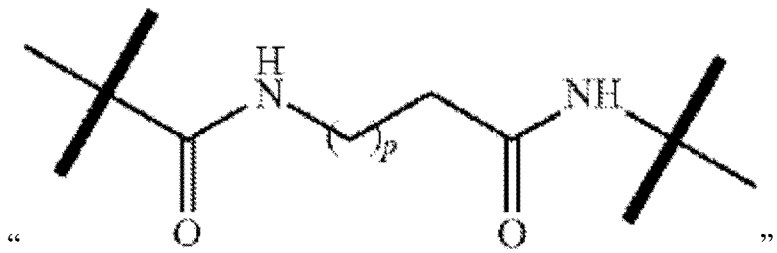

" "

Should be deleted and replaced with:

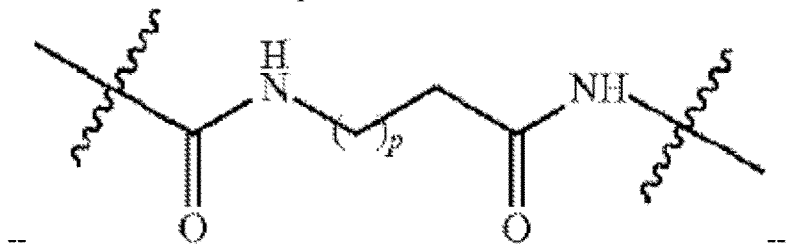

--  --

Column 12, Lines 13-18:

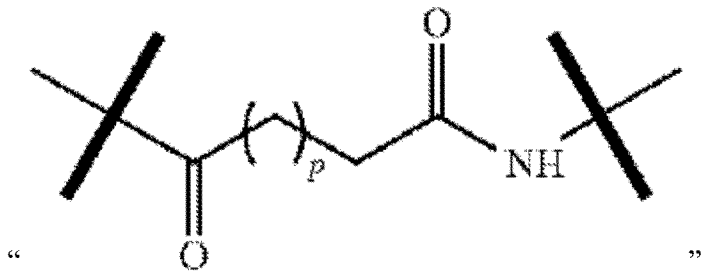

" "

Should be deleted and replaced with:

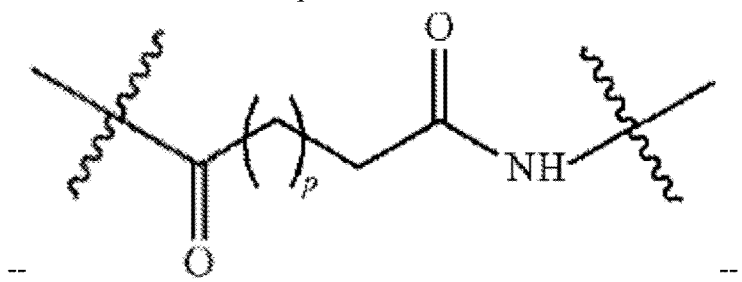

--  --

In the Claims

Claim 2, Column 93, Lines 45-50:
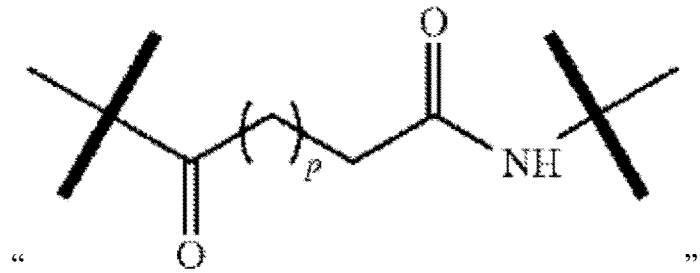
"
Should be deleted and replaced with:
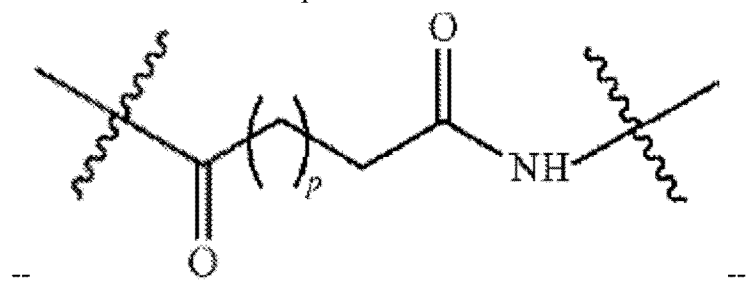
--                                                                                             --
Claim 7, Column 96, Lines 32-37:
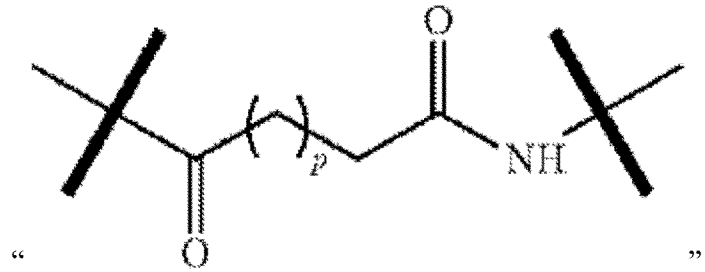
"
Should be deleted and replaced with:
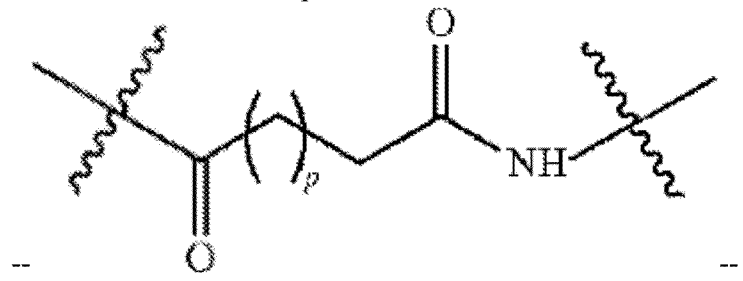
--                                                                                             --
Claim 8, Column 96, Lines 43-57:

CERTIFICATE OF CORRECTION (continued)
U.S. Pat. No. 10,722,599 B2

Page 4 of 4

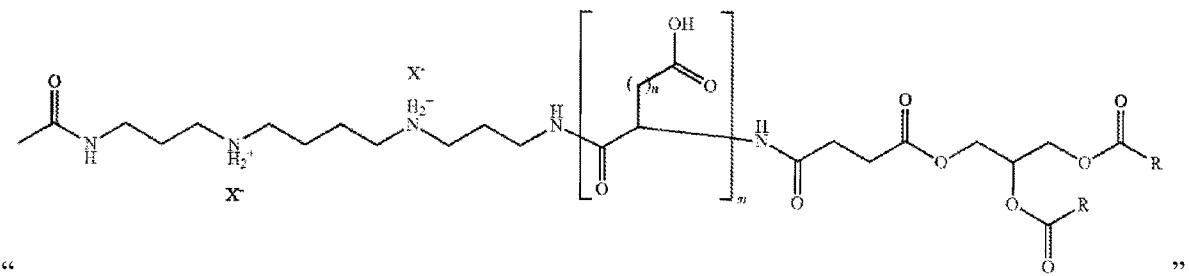

"

Should be deleted and replaced with:

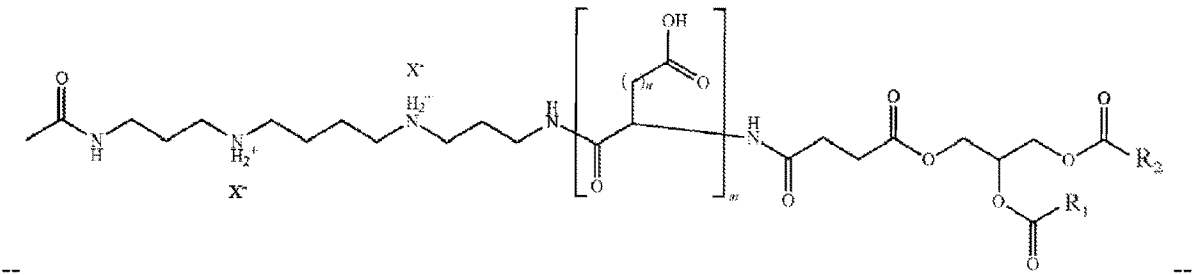

--                                                                                                   --

Claim 8, Column 96, Line 61:
"wherein each of the counter ions X—, independently of"
Should be deleted and replaced with:
-- wherein each of the counter ions X⁻, independently of --

Claim 10, Columns 99-100, second compound:

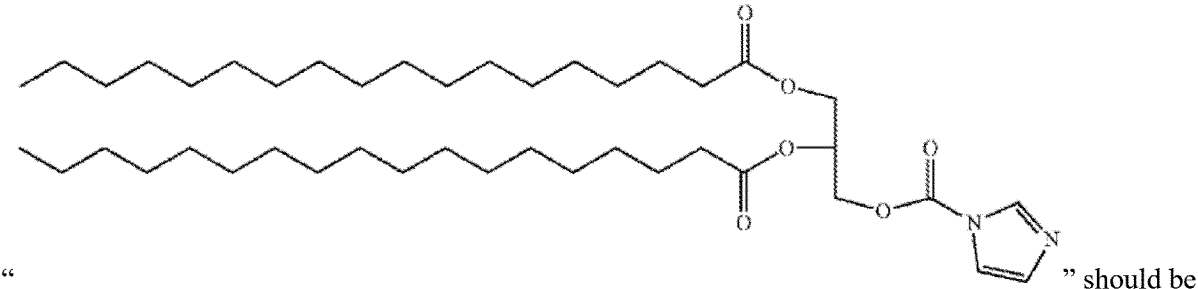

" should be deleted

SEQUENCE LISTING

<160> NUMBER OF SEQ ID NOS: 29

<210> SEQ ID NO 1
<211> LENGTH: 22
<212> TYPE: RNA
<213> ORGANISM: Homo sapiens

<400> SEQUENCE: 1
uggcaguguc uuagcugguu gu                                           22

<210> SEQ ID NO 2
<211> LENGTH: 22
<212> TYPE: RNA
<213> ORGANISM: Homo sapiens

<400> SEQUENCE: 2
acaaucagca aguauacugc cc                                           22

<210> SEQ ID NO 3
<211> LENGTH: 22
<212> TYPE: RNA
<213> ORGANISM: Homo sapiens

<400> SEQUENCE: 3
caaucagcaa guauacugcc cu                                           22

<210> SEQ ID NO 4
<211> LENGTH: 19
<212> TYPE: DNA
<213> ORGANISM: Homo sapiens

<400> SEQUENCE: 4
acttcactgg cagctttgc                                               19

<210> SEQ ID NO 5
<211> LENGTH: 21
<212> TYPE: DNA
<213> ORGANISM: Homo sapiens

<400> SEQUENCE: 5
tggtcttcaa gtagccaaag g                                            21

<210> SEQ ID NO 6
<211> LENGTH: 20
<212> TYPE: DNA
<213> ORGANISM: Homo sapiens

<400> SEQUENCE: 6
tcccaggaga agaagactgg                                              20

<210> SEQ ID NO 7
<211> LENGTH: 21
<212> TYPE: DNA
<213> ORGANISM: Homo sapiens

<400> SEQUENCE: 7

```
tggaagtatg ggtgagacag g                                          21

<210> SEQ ID NO 8
<211> LENGTH: 20
<212> TYPE: DNA
<213> ORGANISM: Homo sapiens

<400> SEQUENCE: 8
aagggcccat tgaggtttac                                            20

<210> SEQ ID NO 9
<211> LENGTH: 20
<212> TYPE: DNA
<213> ORGANISM: Homo sapiens

<400> SEQUENCE: 9
ttggaaggaa tttggtcctc                                            20

<210> SEQ ID NO 10
<211> LENGTH: 20
<212> TYPE: DNA
<213> ORGANISM: Homo sapiens

<400> SEQUENCE: 10
aacaagccgc aacgtaaaat                                            20

<210> SEQ ID NO 11
<211> LENGTH: 20
<212> TYPE: DNA
<213> ORGANISM: Homo sapiens

<400> SEQUENCE: 11
ggaaacgatc ccacgtctta                                            20

<210> SEQ ID NO 12
<211> LENGTH: 23
<212> TYPE: RNA
<213> ORGANISM: Homo sapiens

<400> SEQUENCE: 12
uaggcagugu cauuagcuga uug                                        23

<210> SEQ ID NO 13
<211> LENGTH: 22
<212> TYPE: RNA
<213> ORGANISM: Homo sapiens

<400> SEQUENCE: 13
caaucacuaa cuccacugcc au                                         22

<210> SEQ ID NO 14
<211> LENGTH: 23
<212> TYPE: RNA
<213> ORGANISM: Homo sapiens

<400> SEQUENCE: 14
aggcagugua guuagcugau ugc                                        23

<210> SEQ ID NO 15
<211> LENGTH: 22
<212> TYPE: RNA
<213> ORGANISM: Homo sapiens
```

<400> SEQUENCE: 15
aaucacuaac cacacggcca gg                                    22

<210> SEQ ID NO 16
<211> LENGTH: 24
<212> TYPE: RNA
<213> ORGANISM: Artificial Sequence
<220> FEATURE:
<223> OTHER INFORMATION: Artificial changes to the human sequence

<400> SEQUENCE: 16
acaaucagca aguauacugc ccua                                  24

<210> SEQ ID NO 17
<211> LENGTH: 22
<212> TYPE: RNA
<213> ORGANISM: Artificial Sequence
<220> FEATURE:
<223> OTHER INFORMATION: Artificial changes to the human sequence

<400> SEQUENCE: 17
acaaccagcu aagacacugc ca                                    22

<210> SEQ ID NO 18
<211> LENGTH: 19
<212> TYPE: RNA
<213> ORGANISM: Homo sapiens

<400> SEQUENCE: 18
cgugcaaagu gguauccua                                        19

<210> SEQ ID NO 19
<211> LENGTH: 19
<212> TYPE: RNA
<213> ORGANISM: Homo sapiens

<400> SEQUENCE: 19
guaggauacc acuuugcac                                        19

<210> SEQ ID NO 20
<211> LENGTH: 20
<212> TYPE: RNA
<213> ORGANISM: Homo sapiens

<400> SEQUENCE: 20
ccgugcaaag ugguauccua                                       20

<210> SEQ ID NO 21
<211> LENGTH: 19
<212> TYPE: RNA
<213> ORGANISM: Homo sapiens

<400> SEQUENCE: 21
uaggauacca cuuugcacg                                        19

<210> SEQ ID NO 22
<211> LENGTH: 19
<212> TYPE: RNA
<213> ORGANISM: Homo sapiens

<400> SEQUENCE: 22
cgugcaaagu gguauccua                                        19

```
<210> SEQ ID NO 23
<211> LENGTH: 19
<212> TYPE: RNA
<213> ORGANISM: Homo sapiens

<400> SEQUENCE: 23
uaggauacca cuuugcacg                                                    19

<210> SEQ ID NO 24
<211> LENGTH: 19
<212> TYPE: RNA
<213> ORGANISM: Homo sapiens

<400> SEQUENCE: 24
agaagaugcu ucagacagu                                                    19

<210> SEQ ID NO 25
<211> LENGTH: 19
<212> TYPE: RNA
<213> ORGANISM: Homo sapiens

<400> SEQUENCE: 25
acugucugaa gcaucuucu                                                    19

<210> SEQ ID NO 26
<211> LENGTH: 19
<212> TYPE: RNA
<213> ORGANISM: Homo sapiens

<400> SEQUENCE: 26
agaagaugcu ucagacagu                                                    19

<210> SEQ ID NO 27
<211> LENGTH: 19
<212> TYPE: RNA
<213> ORGANISM: Homo sapiens

<400> SEQUENCE: 27
acugucugaa gcaucuucu                                                    19

<210> SEQ ID NO 28
<211> LENGTH: 19
<212> TYPE: RNA
<213> ORGANISM: Homo sapiens

<400> SEQUENCE: 28
gccacaacgu cuauaucau                                                    19

<210> SEQ ID NO 29
<211> LENGTH: 19
<212> TYPE: RNA
<213> ORGANISM: Homo sapiens

<400> SEQUENCE: 29
augauauaga cguuguggc                                                    19
```